US011197979B2

(12) United States Patent
Crisco et al.

(10) Patent No.: US 11,197,979 B2
(45) Date of Patent: Dec. 14, 2021

(54) VASCULAR ACCESS DEVICES AND METHODS

(71) Applicant: Access Flow Systems, LLC, Atlanta, GA (US)

(72) Inventors: L. Van Thomas Crisco, Jacksonville, FL (US); Ashley B. Hancock, Atlanta, GA (US); Charles Bruce Moomey, Suwanee, GA (US); Brian Patrick Walsh, Charlotte, NC (US); Paul John Grata, Miramar, FL (US); Donald A. Richardson, Fort Mill, SC (US)

(73) Assignee: Access Flow Systems, LLC, Atlanta, GA (US)

( * ) Notice: Subject to any disclaimer, the term of this patent is extended or adjusted under 35 U.S.C. 154(b) by 33 days.

(21) Appl. No.: 16/098,807

(22) PCT Filed: May 3, 2017

(86) PCT No.: PCT/US2017/030819
§ 371 (c)(1),
(2) Date: Nov. 2, 2018

(87) PCT Pub. No.: WO2017/192706
PCT Pub. Date: Nov. 9, 2017

(65) Prior Publication Data
US 2019/0134350 A1   May 9, 2019

Related U.S. Application Data

(60) Provisional application No. 62/331,254, filed on May 3, 2016.

(51) Int. Cl.
*A61M 25/01* (2006.01)
*A61B 17/34* (2006.01)
(Continued)

(52) U.S. Cl.
CPC . *A61M 25/0194* (2013.01); *A61B 17/320016* (2013.01); *A61B 17/3478* (2013.01);
(Continued)

(58) Field of Classification Search
CPC .... A61B 17/320016; A61B 2017/3409; A61B 17/3403; A61B 2017/3405;
(Continued)

(56) References Cited

U.S. PATENT DOCUMENTS 4,813,930 A    3/1989   Elliott
6,645,160 B1 * 11/2003  Heesch ............ A61M 25/0133
                                                128/207.14
(Continued)

OTHER PUBLICATIONS

International Search Report for International Application No. PCT/US2017/030819, dated Jul. 12, 2017.
(Continued)

*Primary Examiner* — Thomas McEvoy
(74) *Attorney, Agent, or Firm* — Eversheds Sutherland (US) LLP

(57) ABSTRACT

Vascular access devices and methods of their use are provided. In one embodiment, a vascular access device includes a catheter (112) and at least one deployable wire (134). The catheter includes a primary lumen extending from a proximal end to a distal end of the catheter. The at least one deployable wire is secured to the catheter and configured to move relative to the catheter between a delivery configuration and a deployed configuration.

12 Claims, 25 Drawing Sheets

(51) Int. Cl.
  *A61B 17/32* (2006.01)
  *A61M 25/00* (2006.01)
  *A61M 25/09* (2006.01)
  *A61M 29/00* (2006.01)
  *A61B 17/00* (2006.01)
  *A61B 17/22* (2006.01)

(52) U.S. Cl.
  CPC ........ *A61M 25/0074* (2013.01); *A61M 25/09* (2013.01); *A61M 29/00* (2013.01); *A61B 17/3415* (2013.01); *A61B 2017/00243* (2013.01); *A61B 2017/00252* (2013.01); *A61B 2017/00278* (2013.01); *A61B 2017/00323* (2013.01); *A61B 2017/00331* (2013.01); *A61B 2017/00867* (2013.01); *A61B 2017/00871* (2013.01); *A61B 2017/22071* (2013.01); *A61B 2017/22095* (2013.01); *A61B 2017/3405* (2013.01); *A61M 2025/0197* (2013.01)

(58) Field of Classification Search
  CPC ............ A61B 17/3415; A61B 17/3478; A61B 2017/22071; A61B 2017/22094; A61B 2017/22095; A61B 17/320783; A61B 2017/00247; A61B 2017/00252; A61M 2025/0197; A61M 2025/0096; A61M 2025/009
  See application file for complete search history.

(56) References Cited

U.S. PATENT DOCUMENTS

| | | | |
|---|---|---|---|
| 8,920,449 B2* | 12/2014 | Wilkinson | A61B 17/22 606/159 |
| 2003/0171714 A1 | 9/2003 | Katoh et al. | |
| 2009/0182360 A1 | 7/2009 | Makower | |
| 2009/0198153 A1 | 8/2009 | Shriver | |
| 2009/0230167 A1 | 9/2009 | Xiao et al. | |
| 2013/0006282 A1 | 1/2013 | Wilkinson | |
| 2015/0173592 A1* | 6/2015 | Leeflang | A61B 1/313 600/106 |
| 2015/0250991 A1* | 9/2015 | Silvestro | A61M 25/0194 606/194 |
| 2018/0078117 A1* | 3/2018 | Voncken | A61M 25/005 |

OTHER PUBLICATIONS

Written Opinion of the International Searching Authority for International Application No. PCT/US2017/030819, dated Jul. 12, 2017.

* cited by examiner

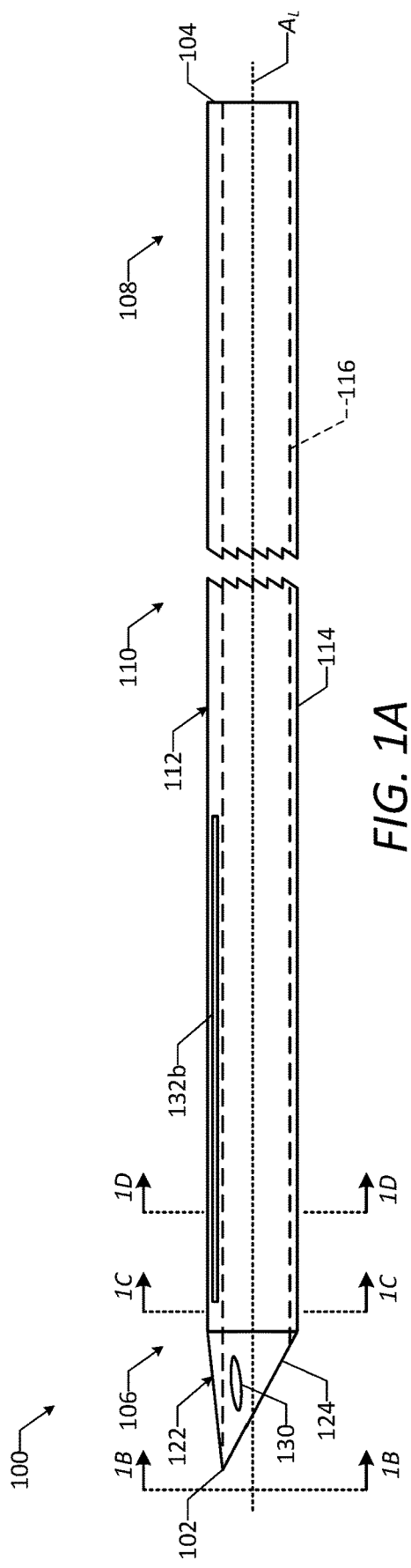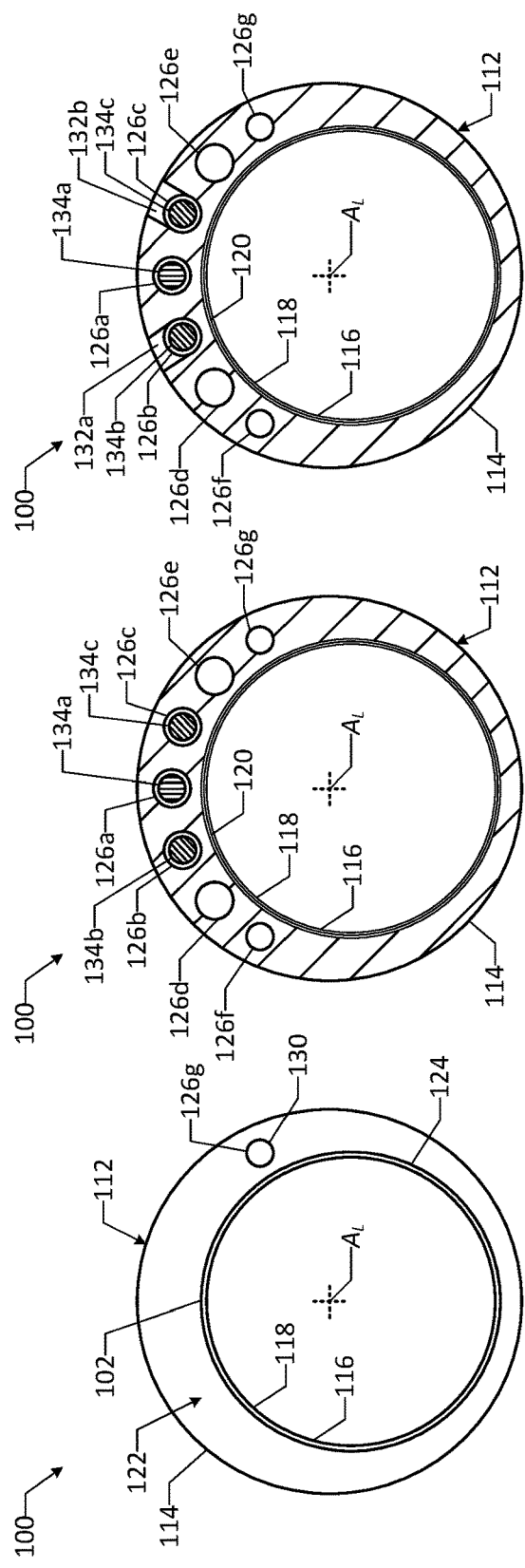

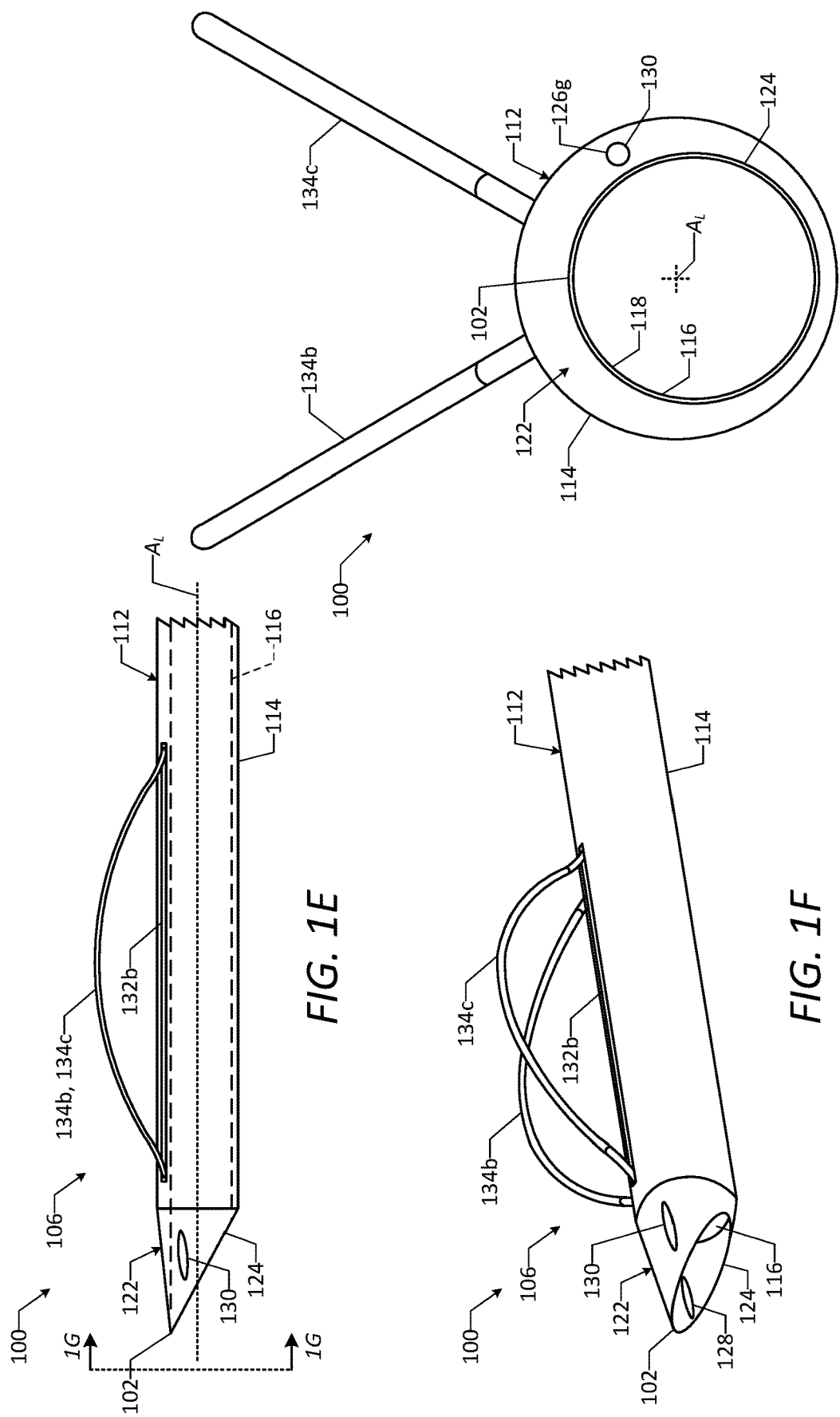

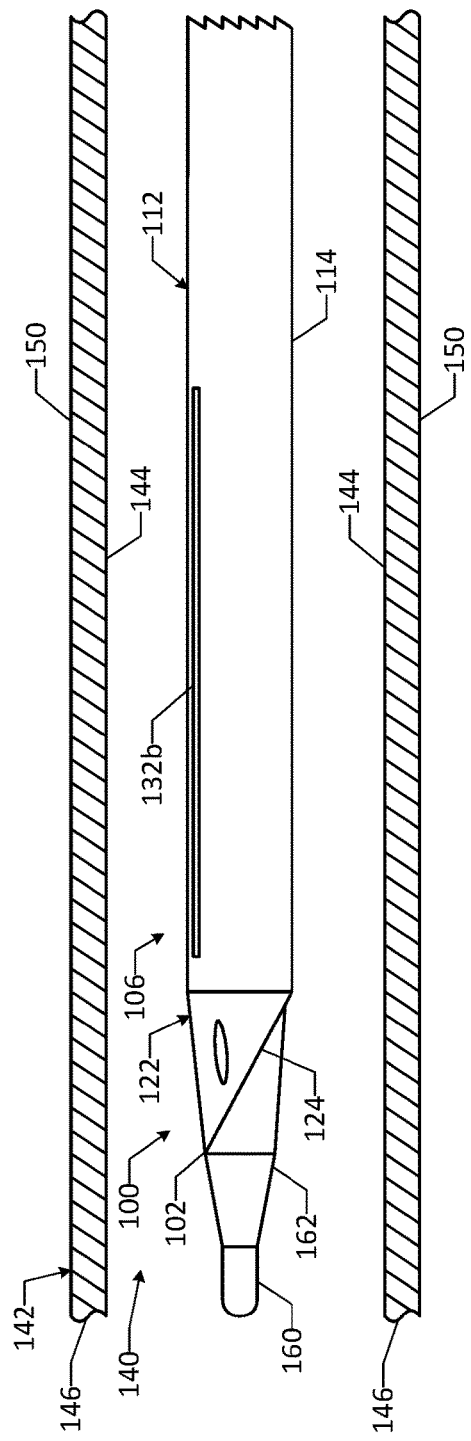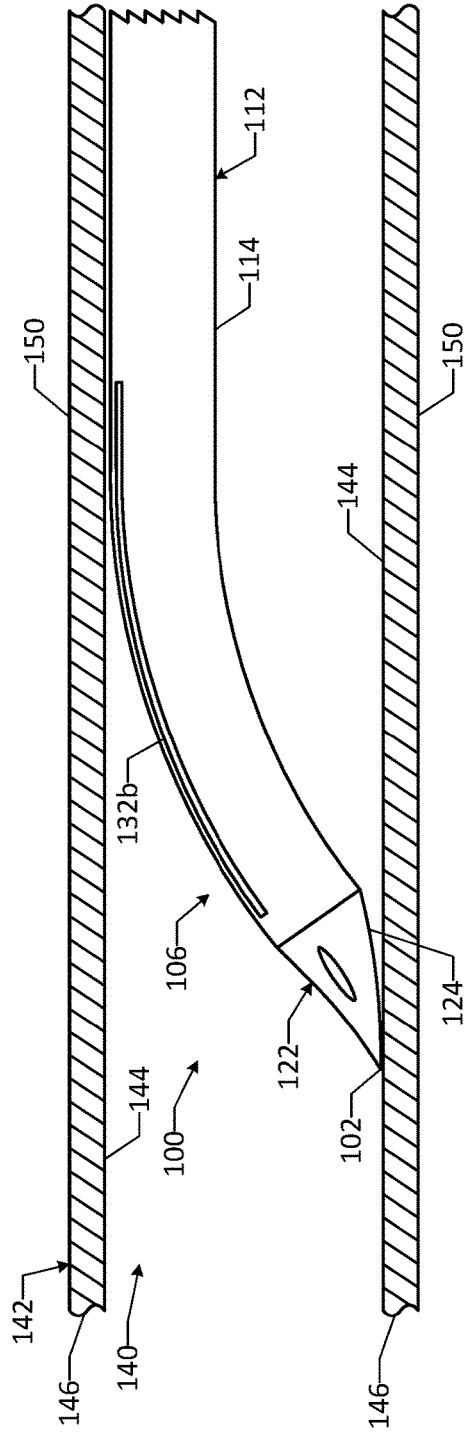

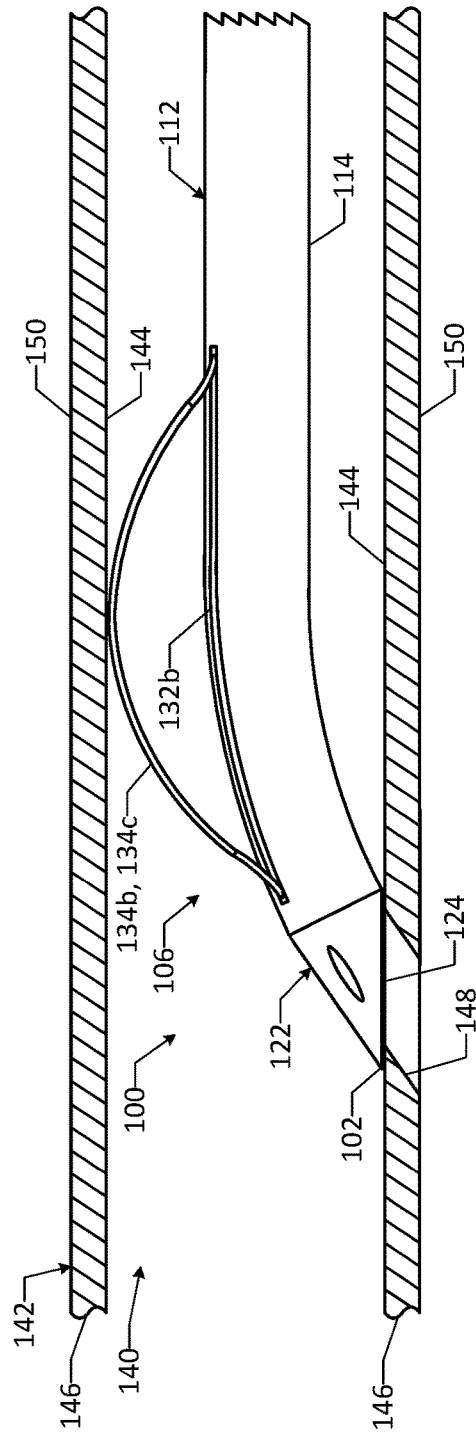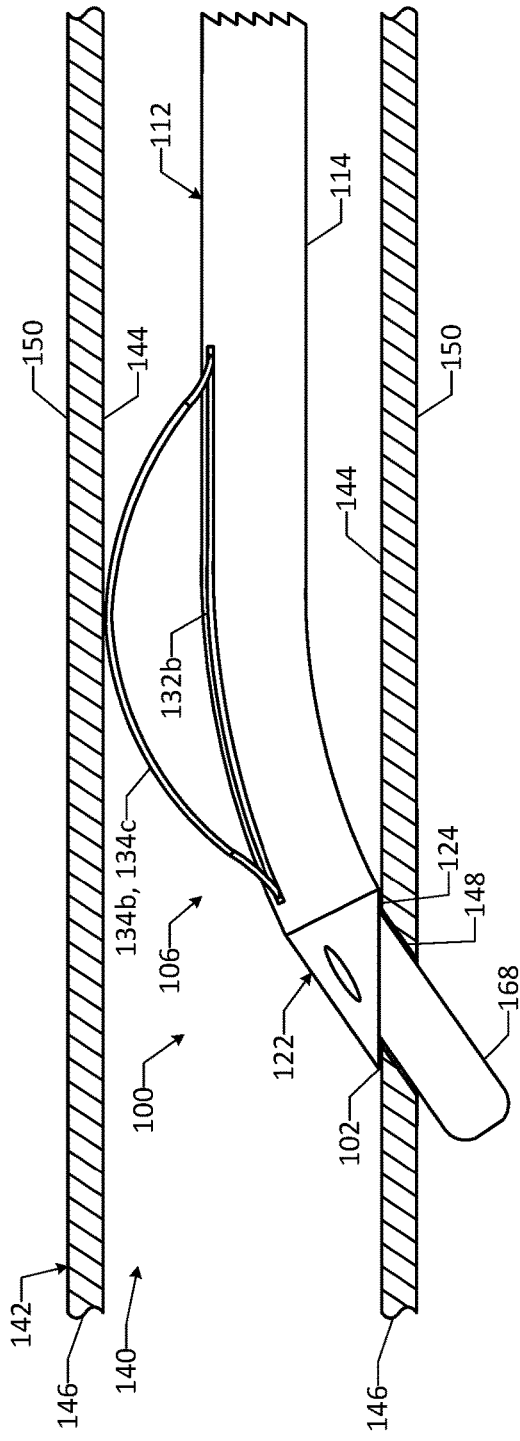

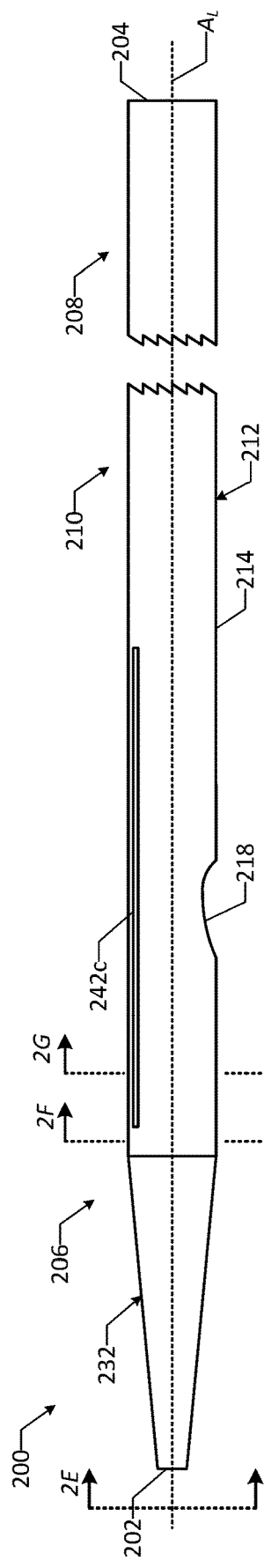
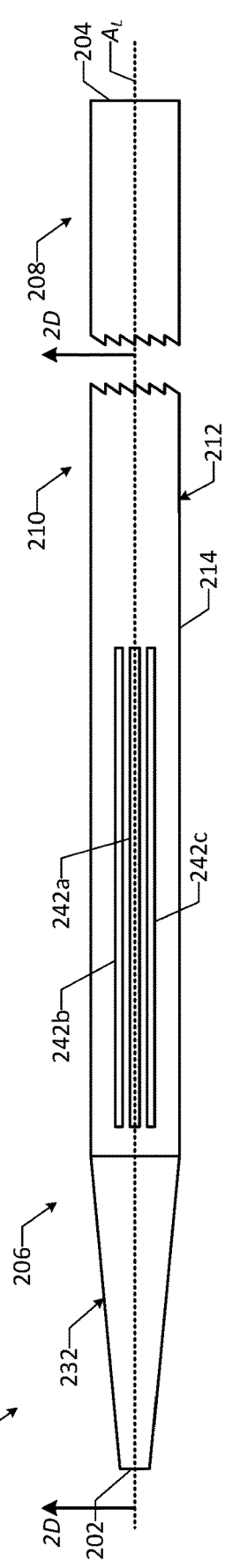
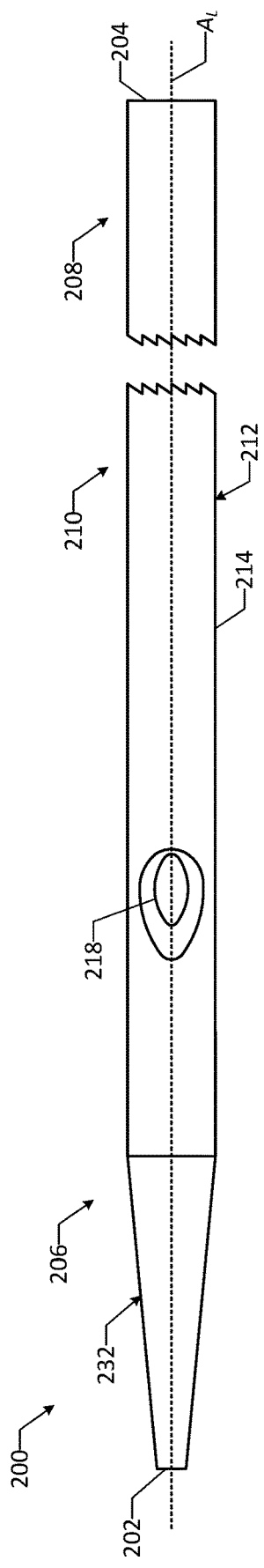
FIG. 2A
FIG. 2B
FIG. 2C

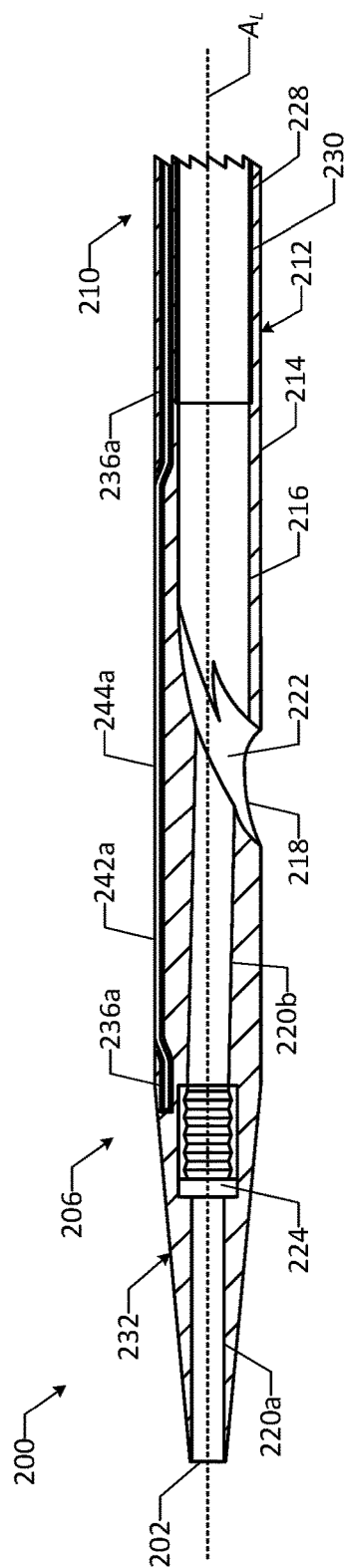
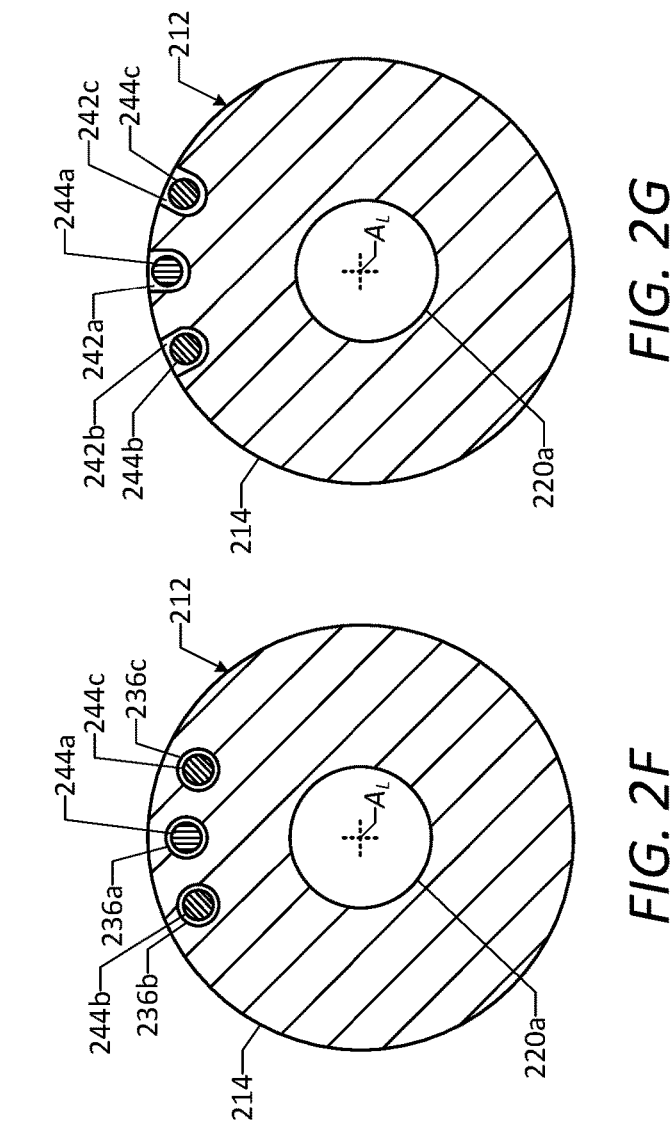
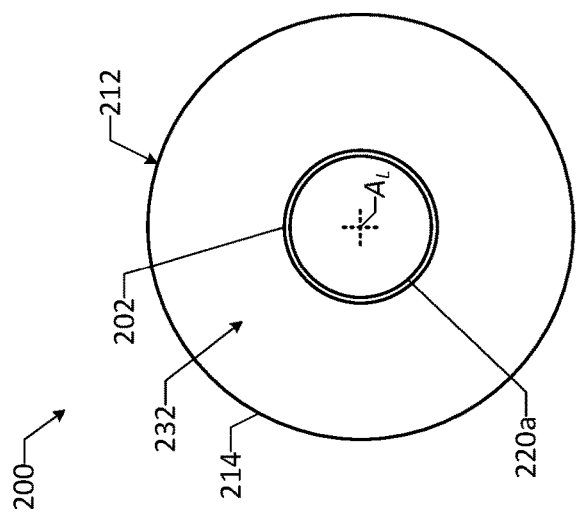
FIG. 2D
FIG. 2E
FIG. 2F
FIG. 2G

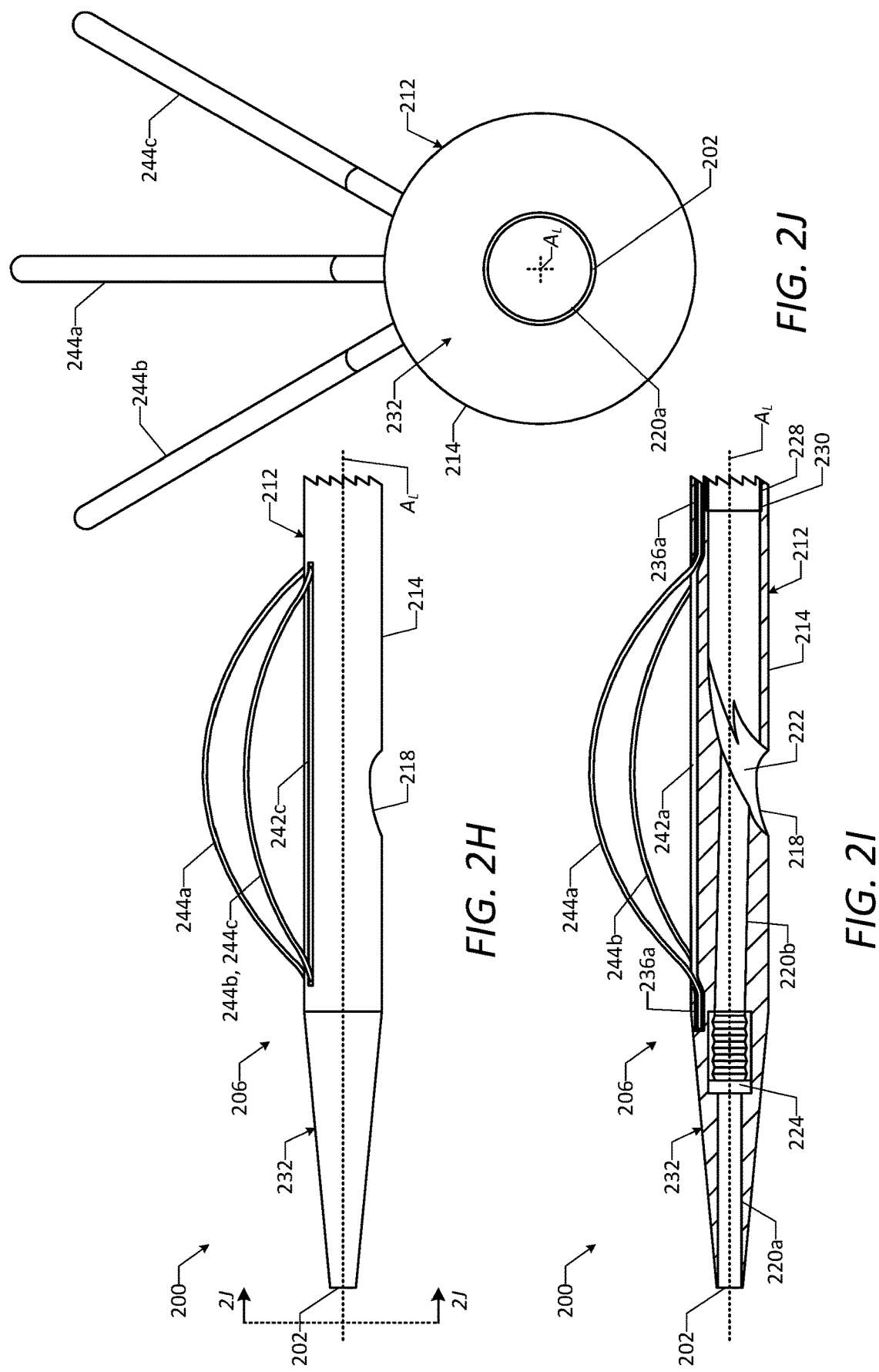

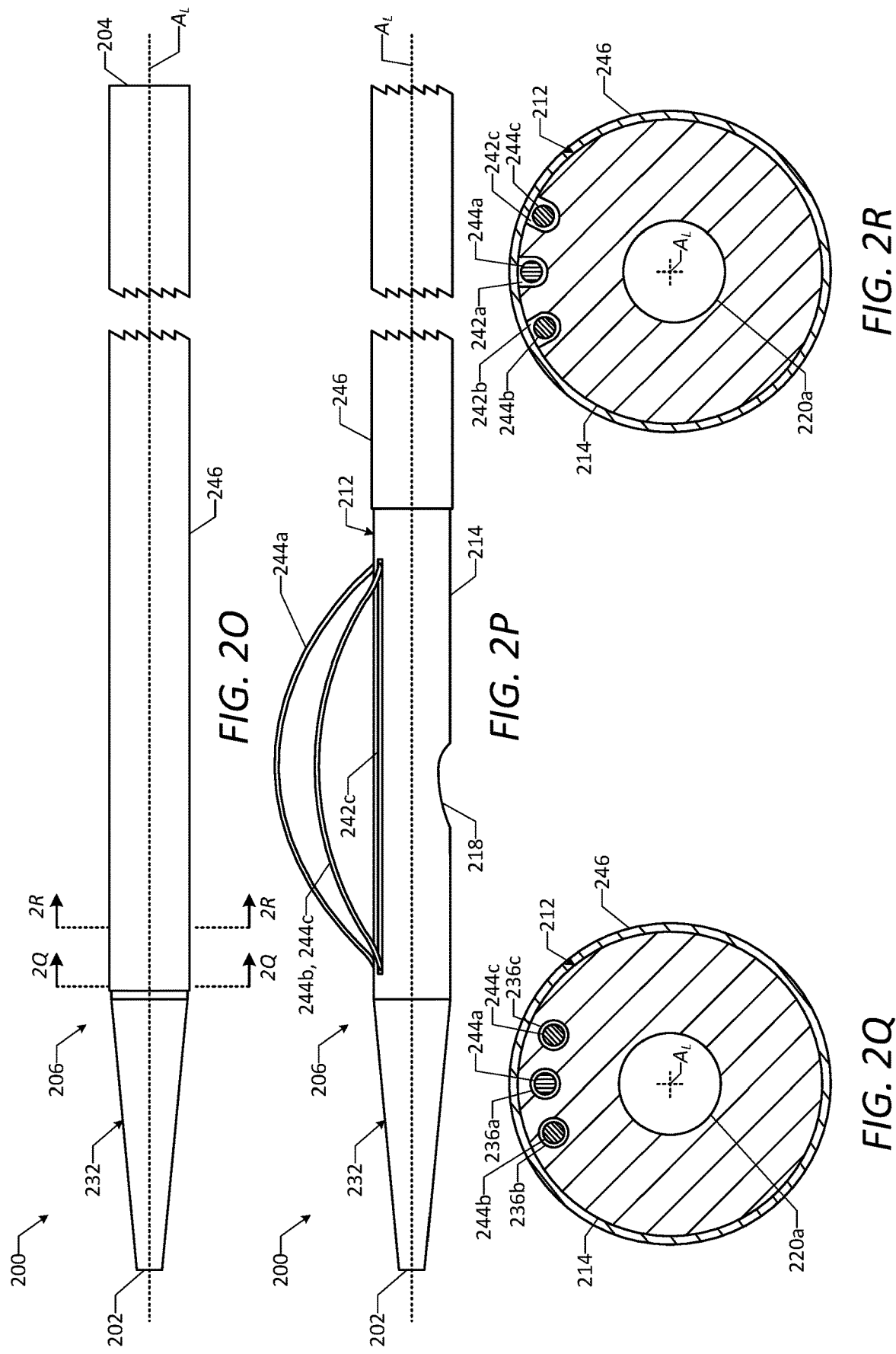

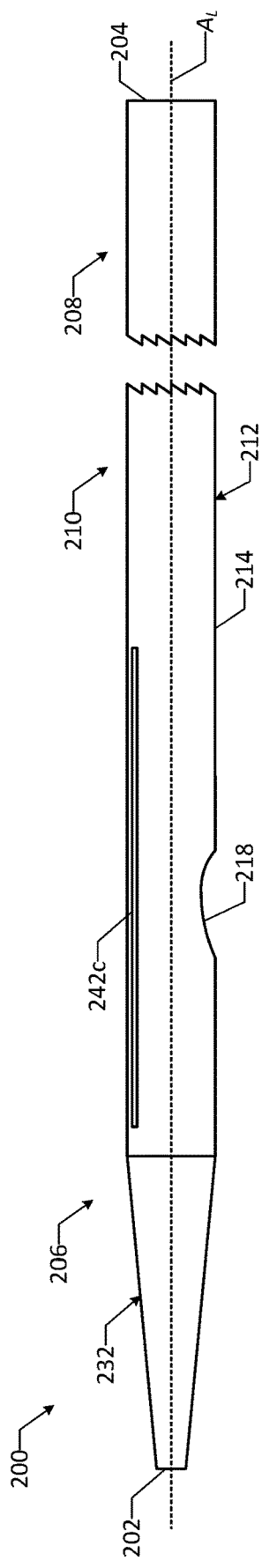
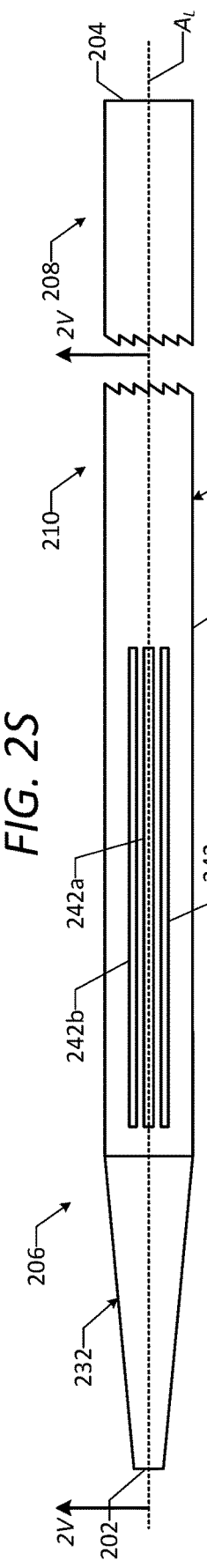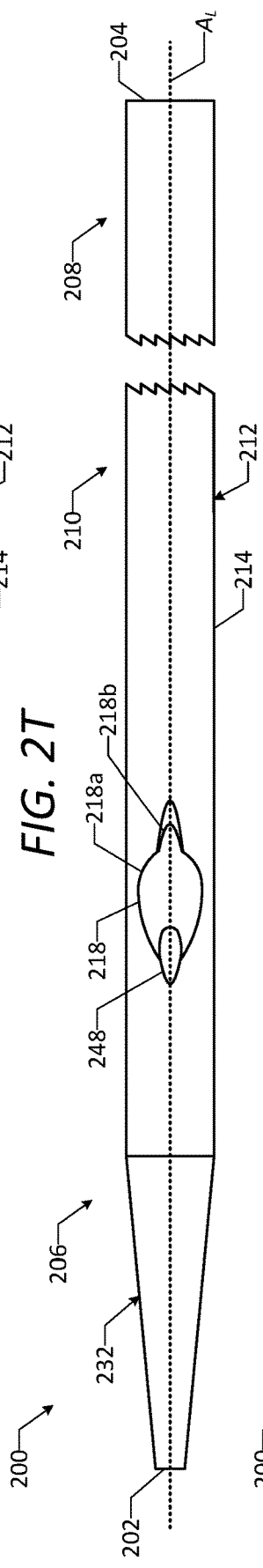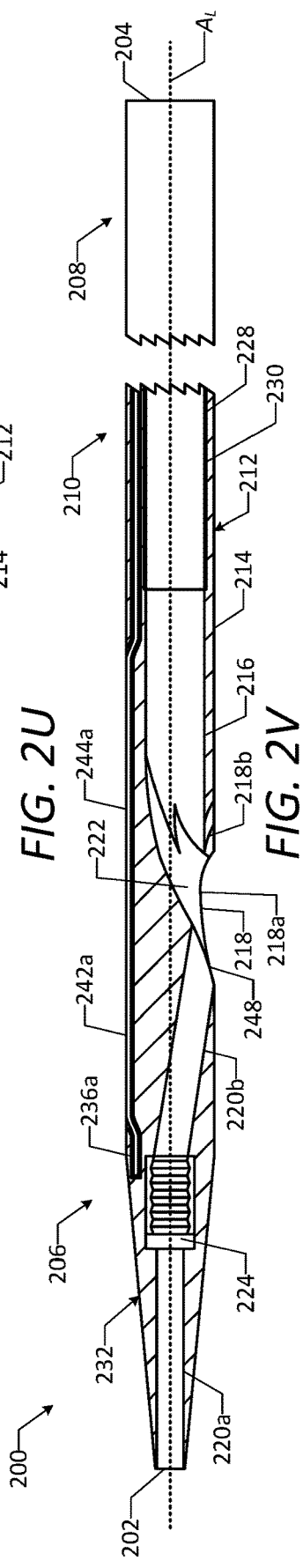
FIG. 2S
FIG. 2T
FIG. 2U
FIG. 2V

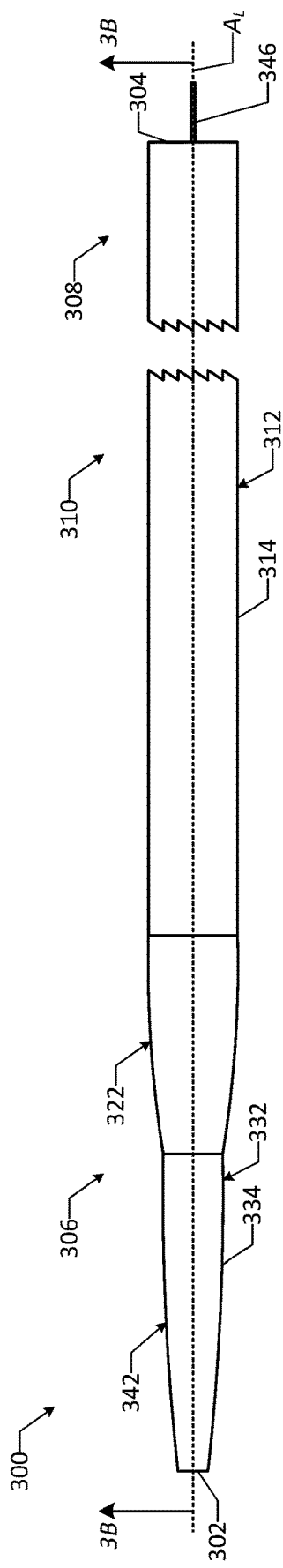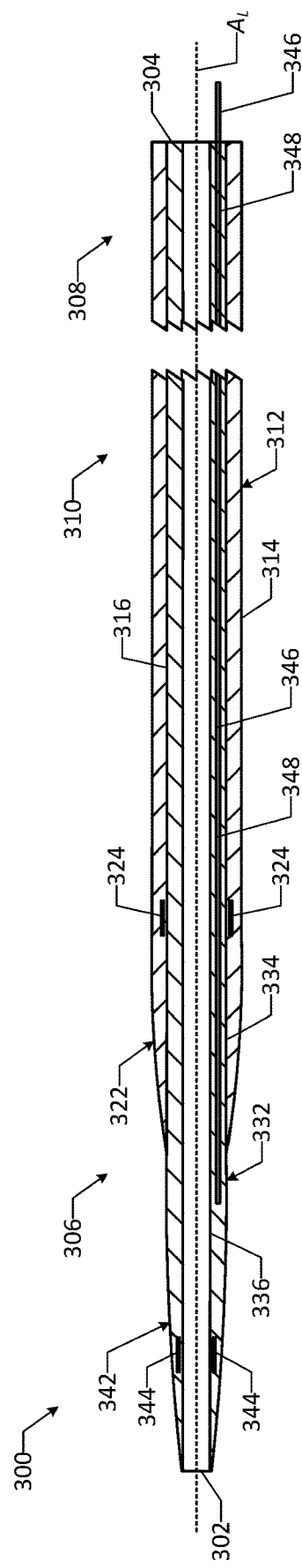
FIG. 3A
FIG. 3B

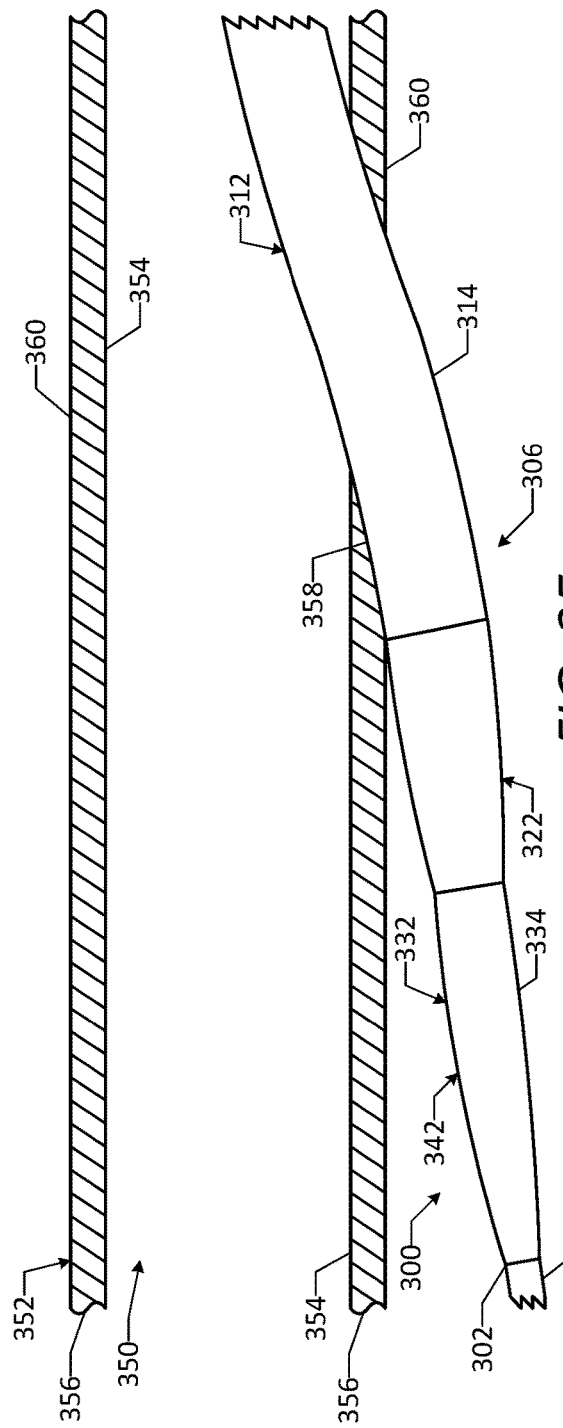
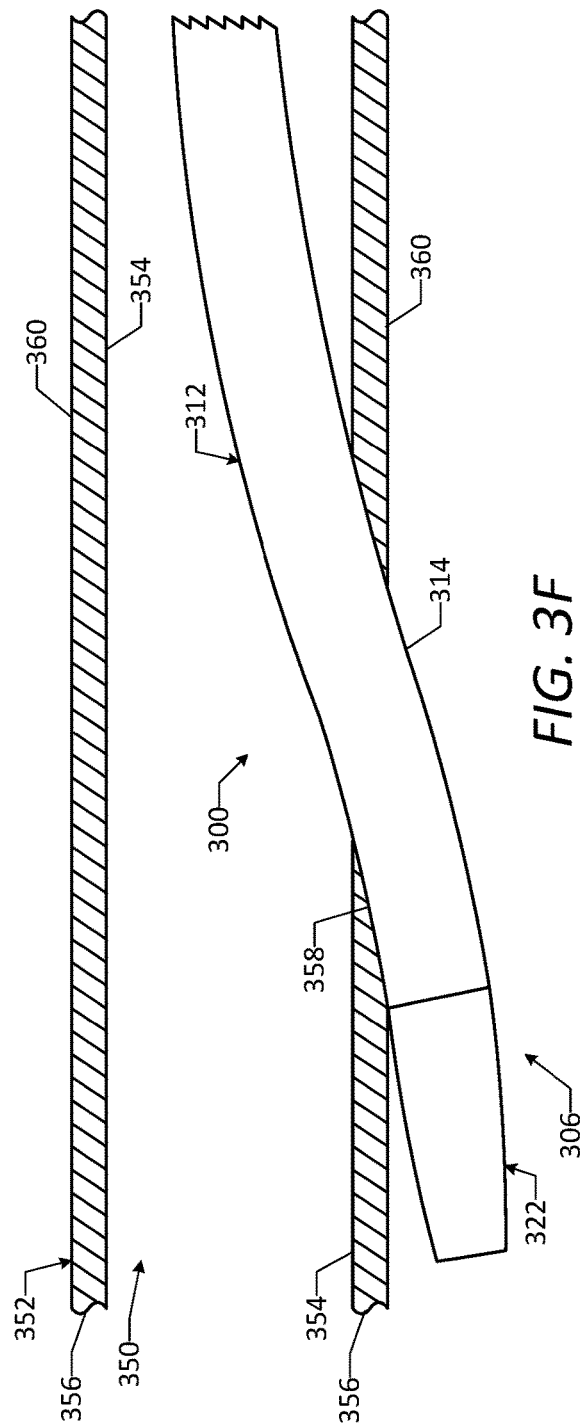

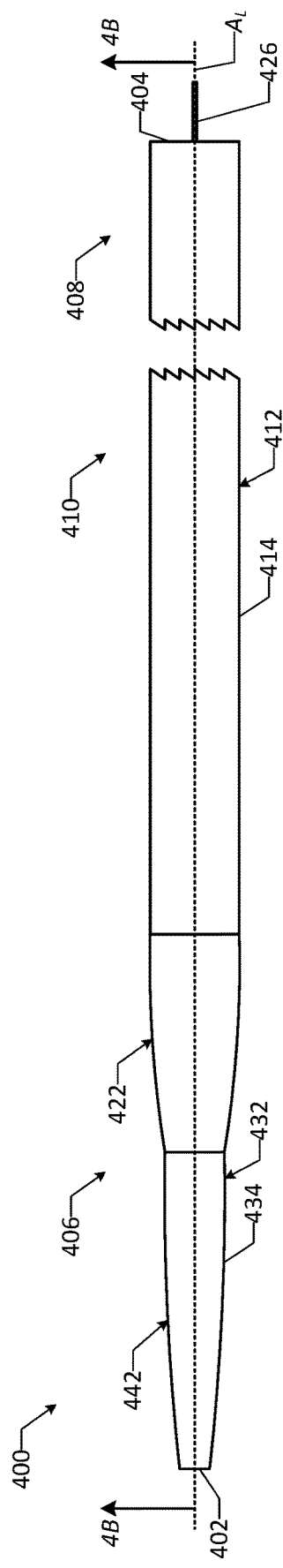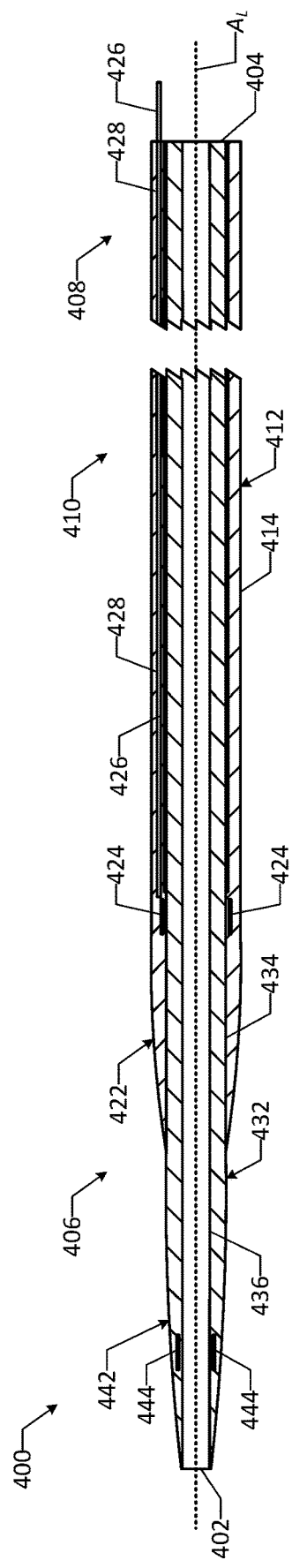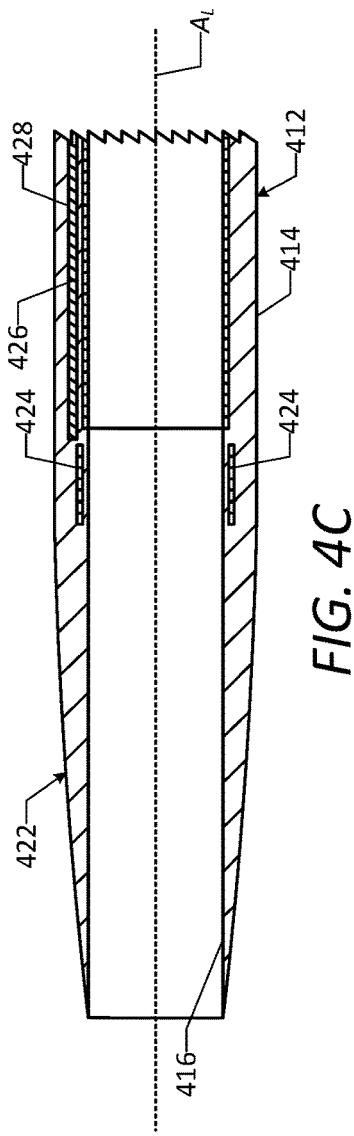

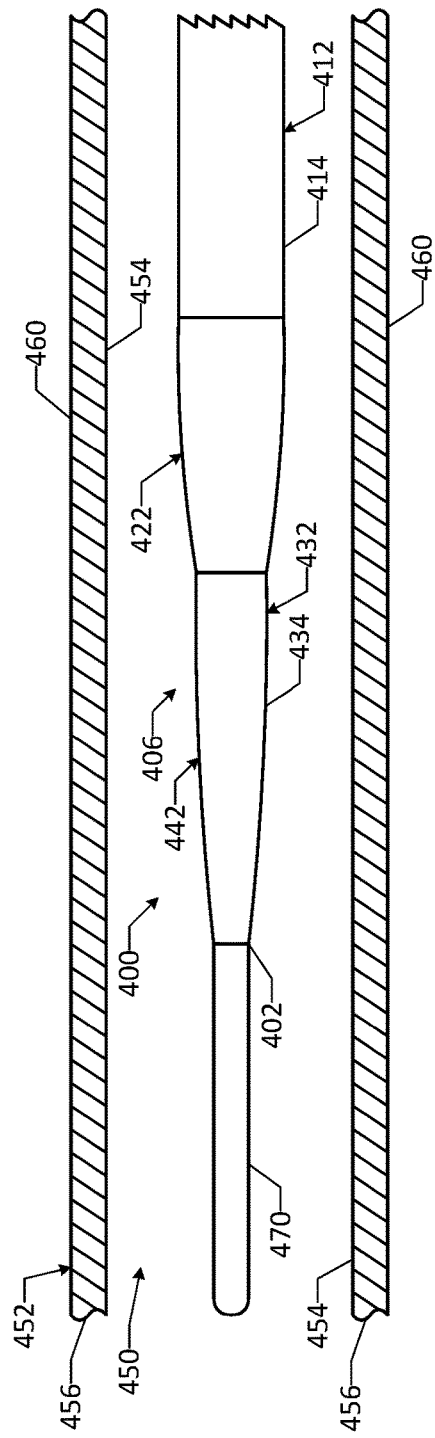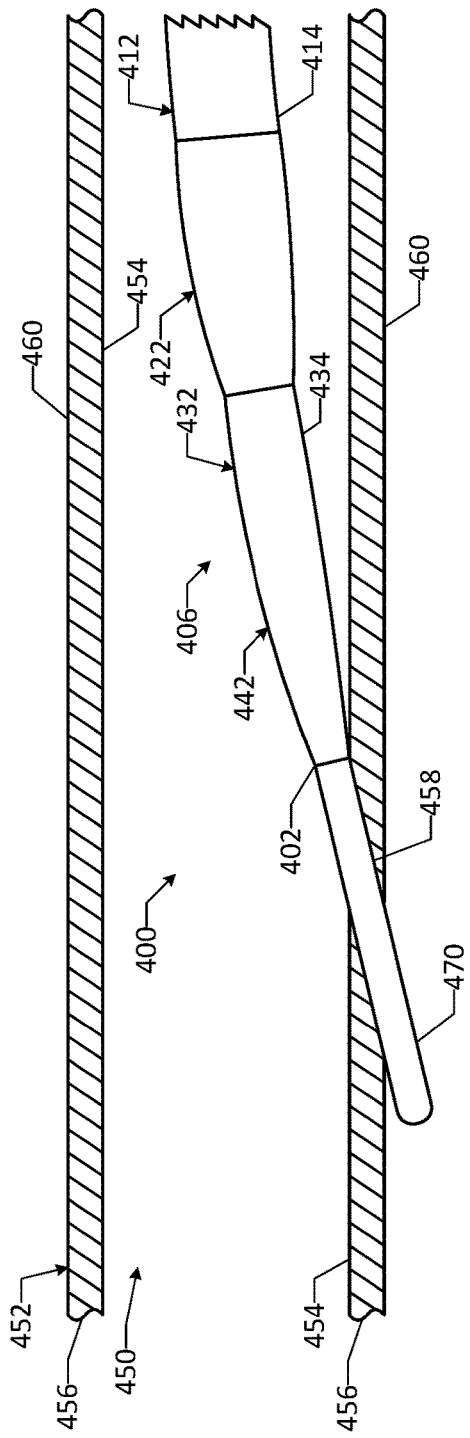
FIG. 4D
FIG. 4E

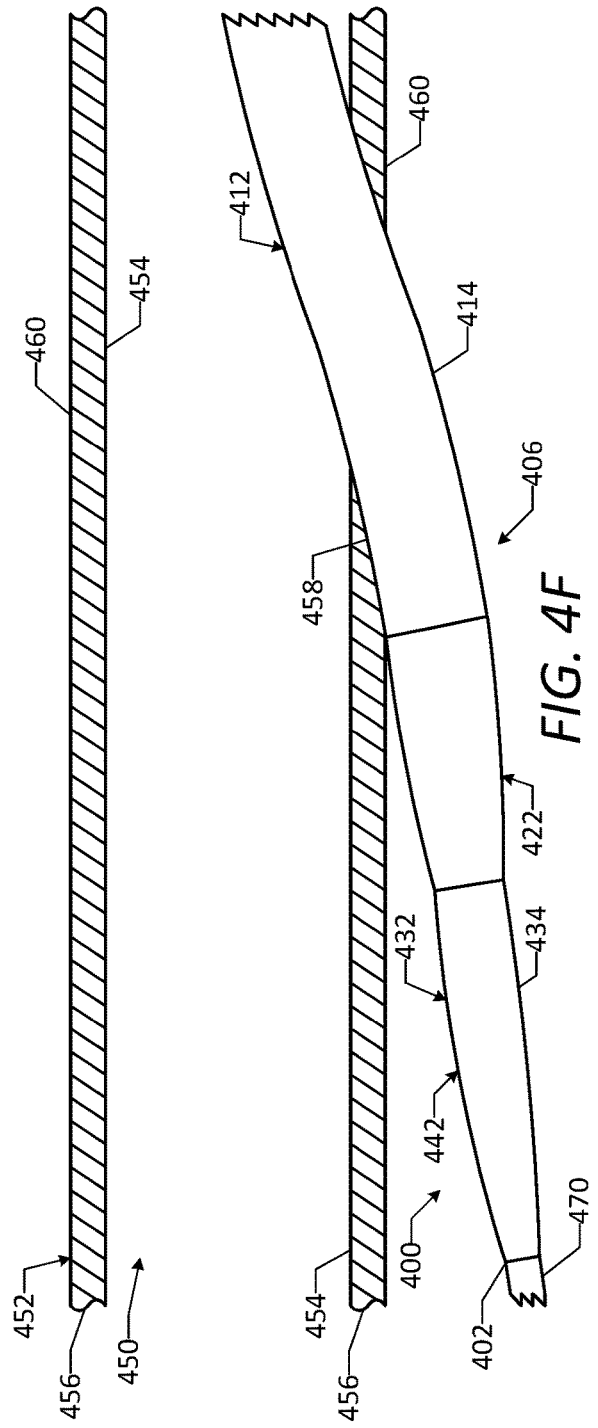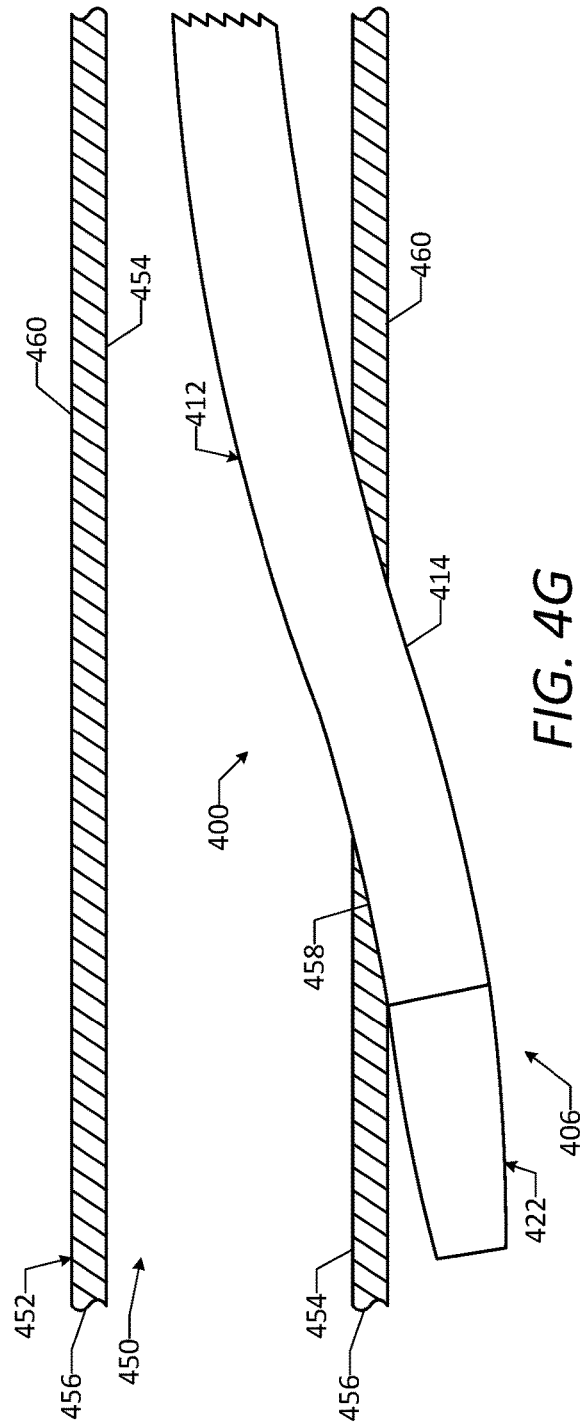

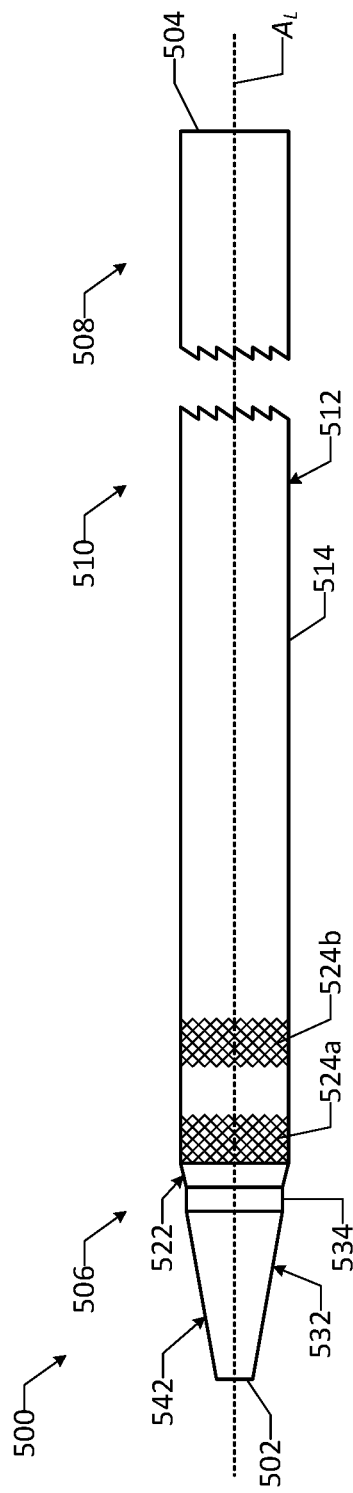
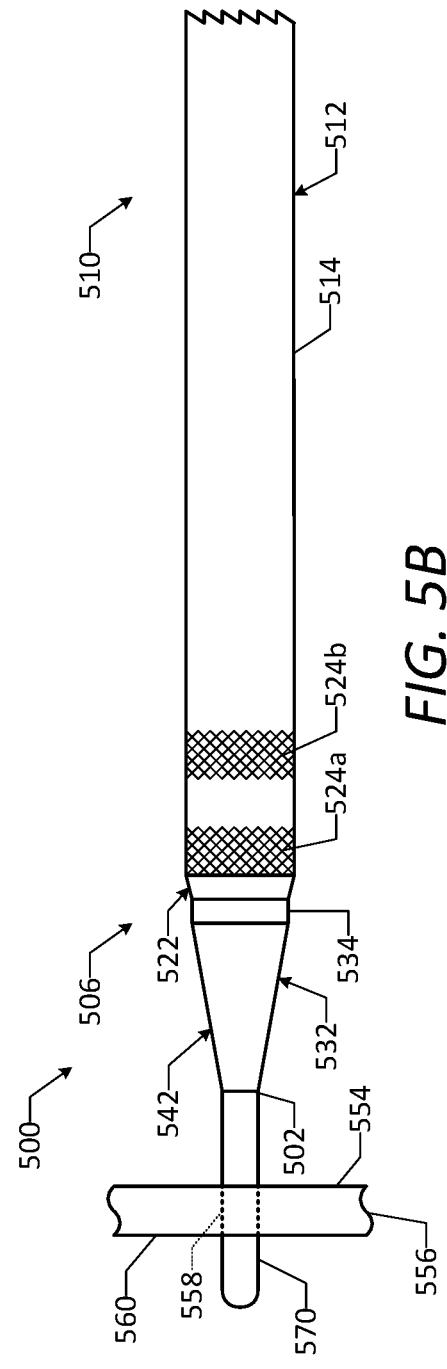
FIG. 5A
FIG. 5B

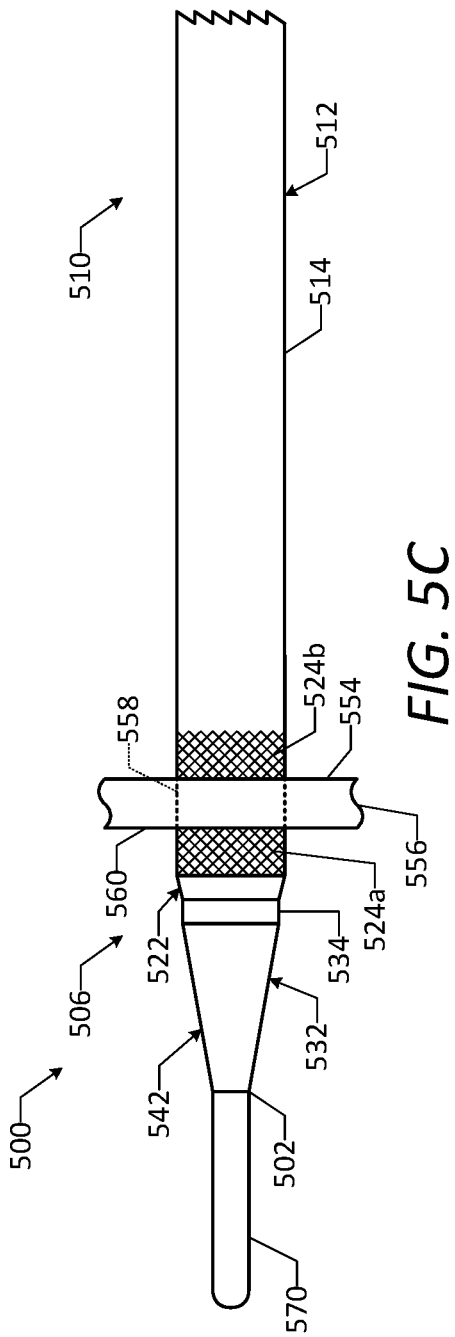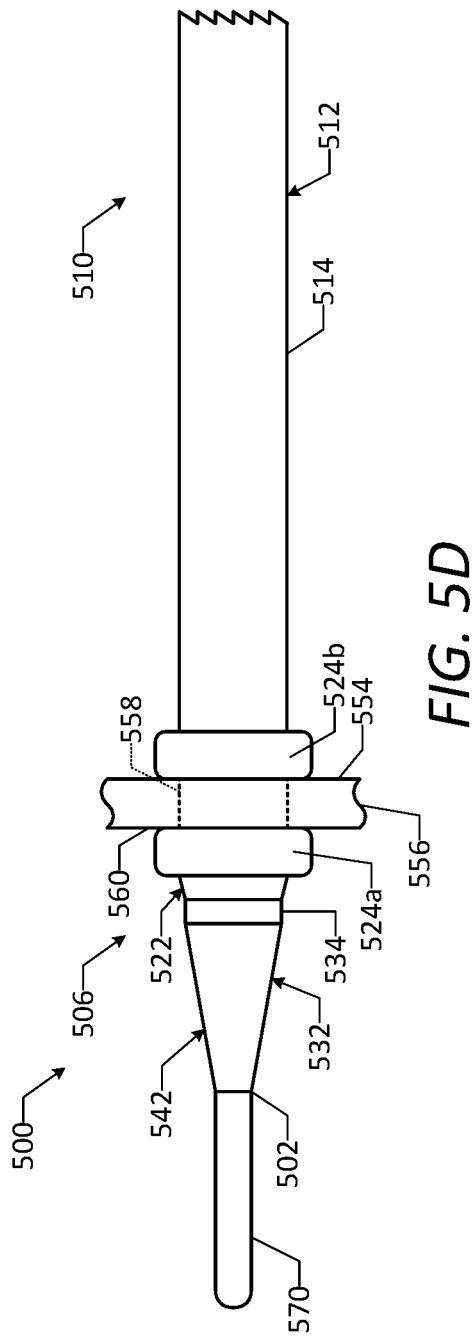

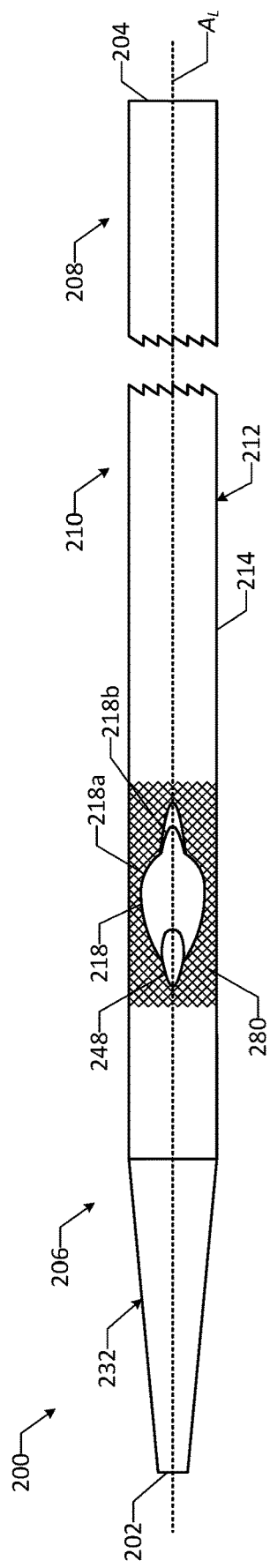
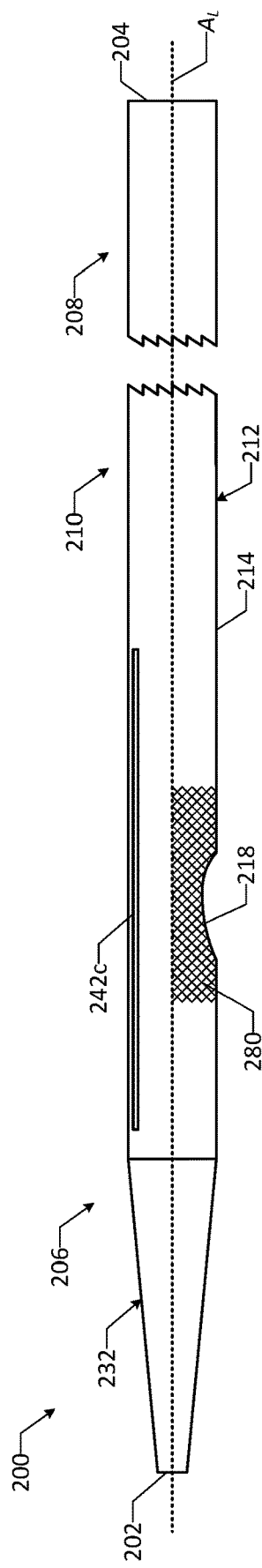
FIG. 5G
FIG. 5H

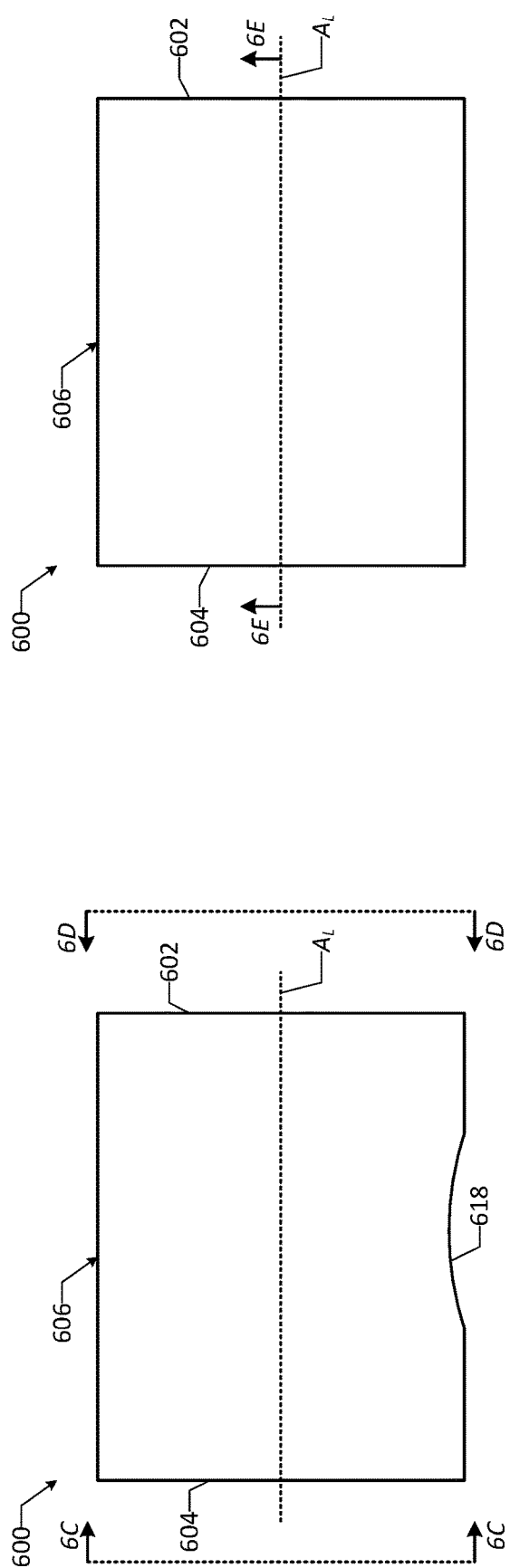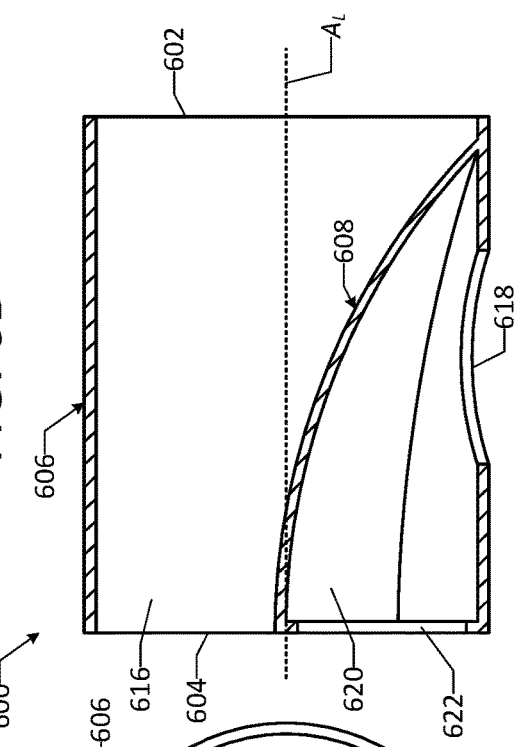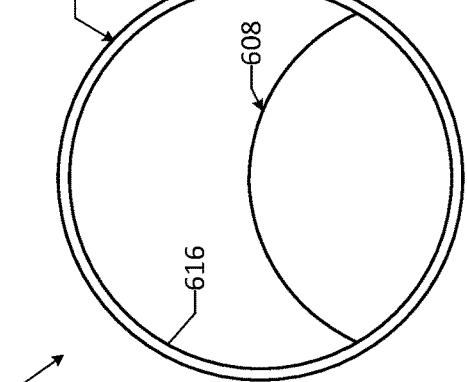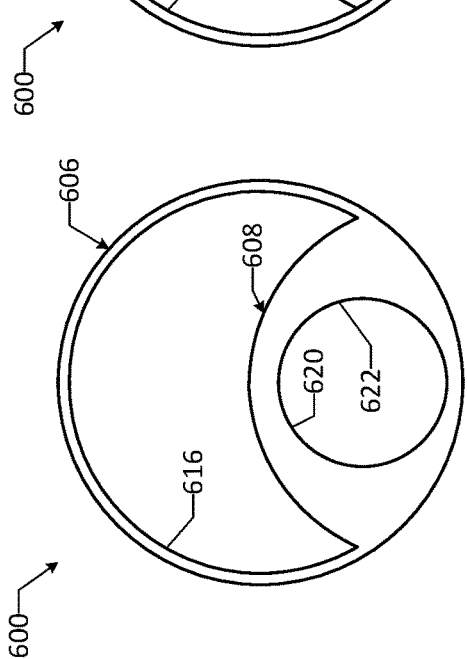

VASCULAR ACCESS DEVICES AND METHODS

CROSS-REFERENCE TO RELATED APPLICATIONS

This application is a U.S. national stage application of International Application No. PCT/US2017/030819, filed on May 3, 2017, which claims the benefit of U.S. Provisional Application No. 62/331,254, filed on May 3, 2016, both of which are incorporated herein by reference in their entirety.

TECHNICAL FIELD

The present disclosure relates generally to medical devices and methods, and more particularly to endovascular access devices and related methods of using such devices to provide access for performing a medical procedure on a patient in need thereof.

BACKGROUND

Many types of surgical and interventional procedures have previously been developed for use in organs, tissues, or body cavities of the body. Traditionally, access to such organs, tissues, or body cavities is attained through the formation of one or more open surgical incisions in the body, whereby the affected organs, tissues, or body cavities are surgically exposed. In recent years, "minimally invasive" surgical/interventional techniques have been developed in which endoscopes are utilized to view the affected organ, tissue, or body cavity, and operative instruments or other devices are inserted into the body through relatively small access incisions to accomplish the desired interventional procedure. These minimally invasive techniques have replaced many traditional open surgical techniques in various areas of medicine, such as cardiology.

In performing certain cardiac interventional procedures, such as a coronary bypass procedure, access to desired vasculature may be achieved by percutaneously inserting an access device through the natural lumen of a vessel, forming a hemostatic connection between the access device and an inner surface of a wall of the vessel, and forming an aperture through the vessel wall to access a thoracic region of the patient. Operative instruments or other devices then may be passed through the access device and the aperture in the vessel wall and into the thoracic region to perform a cardiac procedure on the desired vasculature. Example devices and methods for providing this type of endovascular access for various cardiac procedures, such as a coronary bypass procedure, are described in U.S. Pat. No. 8,663,321 to Crisco, which is incorporated by reference herein.

There remains a need for improved vascular access devices and methods of using such devices to provide access for performing cardiac interventional procedures on patients in need thereof. In particular, it would be advantageous to provide a vascular access device that easily passes through the natural lumen of a vessel, quickly and effectively forms a hemostatic connection between the access device and an inner surface of a wall of the vessel, and provides a working lumen of sufficient size to allow operative instruments or other devices to be passed therethrough to perform a desired cardiac procedure on the patient. Desirably, the vascular access device should allow a physician to assess the integrity of the hemostatic connection and an aperture formed through the vessel wall. The vascular access device also should allow sufficient blood flow to pass through the natural lumen of the vessel while the access device is positioned therein.

BRIEF SUMMARY

Vascular access devices and methods of using such devices to provide access for performing cardiac interventional procedures are provided. According to one aspect, a vascular access device is provided. In one embodiment, the vascular access device includes a catheter and at least one deployable wire. The catheter includes a primary lumen extending from a proximal end to a distal end of the catheter. The at least one deployable wire is secured to the catheter and configured to move relative to the catheter between a delivery configuration and a deployed configuration.

In another aspect, a method of using a vascular access device to provide access for performing a cardiac procedure on a patient is provided. In one embodiment, the method includes the steps of percutaneously inserting a distal end portion of the vascular access device into a natural lumen of a vessel of the patient, deploying at least one deployable wire from a catheter of the vascular access device such that the deployable wire engages an inner surface of a wall of the vessel and biases the catheter to engage the inner surface such that a hemostatic connection is formed between the catheter and the inner surface, and advancing at least one instrument through the catheter and through the wall to form an aperture in the wall, while maintaining the hemostatic connection between the catheter and the inner surface.

These and other aspects and embodiments of the present disclosure will be apparent or will become apparent to one of ordinary skill in the art upon review of the following detailed description when taken in conjunction with the drawings and the appended claims.

BRIEF DESCRIPTION OF THE DRAWINGS

FIG. 1A is a side view of a vascular access device in accordance with one or more embodiments of the disclosure.

FIG. 1B is a detailed end view of the vascular access device of FIG. 1A, taken along line 1B-1B in FIG. 1A.

FIG. 1C is a detailed cross-sectional end view of the vascular access device of FIG. 1A, taken along line 1C-1C in FIG. 1A.

FIG. 1D is a detailed cross-sectional end view of the vascular access device of FIG. 1A, taken along line 1D-1D in FIG. 1A.

FIG. 1E is a side view of a distal end portion of the vascular access device of FIG. 1A, showing a number of deployable wires of the vascular access device in a deployed configuration.

FIG. 1F is a perspective view of the distal end portion of the vascular access device of FIG. 1A, showing the deployable wires of the vascular access device in the deployed configuration.

FIG. 1G is a detailed end view of the distal end portion of the vascular access device of FIG. 1A, taken along line 1G-1G in FIG. 1E, showing the deployable wires of the vascular access device in the deployed configuration.

FIG. 1H is a side view of a portion of the vascular access device of FIG. 1A positioned within a natural lumen of a vessel, showing a distal end portion of the vascular access device in a straight configuration and the deployable wires in a delivery configuration.

FIG. 1I is a side view of a portion of the vascular access device of FIG. 1A positioned within the natural lumen of the vessel, showing the distal end portion in a curved configuration.

FIG. 1L is a side view of a portion of the vascular access device of FIG. 1A positioned within the natural lumen of the vessel, showing the aperture in the vessel wall and a hemostatic connection formed between the distal end portion and the vessel wall.

FIG. 1M is a side view of a portion of the vascular access device of FIG. 1A positioned within the natural lumen of the vessel, showing an operative instrument or device passed through the vascular access device and the aperture in the vessel wall.

FIG. 2A is a side view of a vascular access device in accordance with one or more embodiments of the disclosure.

FIG. 2B is a top view of the vascular access device of FIG. 2A.

FIG. 2C is a bottom view of the vascular access device of FIG. 2A.

FIG. 2D is a cross-sectional side view of the vascular access device of FIG. 2A, taken along line 2D-2D in FIG. 2B.

FIG. 2E is a detailed end view of the vascular access device of FIG. 2A, taken along line 2E-2E in FIG. 2A.

FIG. 2F is a detailed cross-sectional end view of the vascular access device of FIG. 2A, taken along line 2F-2F in FIG. 2A.

FIG. 2G is a detailed cross-sectional end view of the vascular access device of FIG. 2A, taken along line 2G-2G in FIG. 2A.

FIG. 2H is a side view of a distal end portion of the vascular access device of FIG. 2A, showing a number of deployable wires of the vascular access device in a deployed configuration.

FIG. 2I is a cross-sectional side view of the distal end portion of the vascular access device of FIG. 2A, showing the deployable wires of the vascular access device in the deployed configuration.

FIG. 2J is a detailed end view of the distal end portion of the vascular access device of FIG. 2A, taken along line 2J-2J in FIG. 2H, showing the deployable wires of the vascular access device in the deployed configuration.

FIG. 2O is a side view of the vascular access device of FIG. 2A and a sheath, showing the sheath in an advanced position.

FIG. 2P is a side view of the vascular access device of FIG. 2A and the sheath, showing the sheath in a retracted position and the deployable wires in the deployed configuration.

FIG. 2Q is a detailed cross-sectional end view of the vascular access device of FIG. 2A and the sheath, taken along line 2Q-2Q in FIG. 2O.

FIG. 2R is a detailed cross-sectional end view of the vascular access device of FIG. 2A and the sheath, taken along line 2R-2R in FIG. 2O.

FIG. 2S is a side view of a vascular access device in accordance with one or more embodiments of the disclosure.

FIG. 2T is a top view of the vascular access device of FIG. 2S.

FIG. 2U is a bottom view of the vascular access device of FIG. 2S.

FIG. 2V is a cross-sectional side view of the vascular access device of FIG. 2S, taken along line 2V-2V in FIG. 2T.

FIG. 3A is a top view of a vascular access device in accordance with one or more embodiments of the disclosure.

FIG. 3B is a cross-sectional side view of the vascular access device of FIG. 3A, taken along line 3B-3B in FIG. 3A.

FIG. 3E is a side view of a portion of the vascular access device of FIG. 3A positioned within the natural lumen of the vessel, showing a catheter of the vascular access device passed through the aperture in the vessel wall.

FIG. 3F is a side view of a portion of the vascular access device of FIG. 3A positioned within the natural lumen of the vessel, showing the catheter passed through the aperture in the vessel wall and a hemostatic connection formed between the catheter and the vessel wall.

FIG. 4A is a top view of a vascular access device in accordance with one or more embodiments of the disclosure.

FIG. 4B is a cross-sectional side view of the vascular access device of FIG. 4A, taken along line 4B-4B in FIG. 4A.

FIG. 4C is a detailed cross-sectional side view of a portion of a catheter of the vascular access device of FIG. 4A.

FIG. 4D is a side view of a portion of the vascular access device of FIG. 4A positioned within a natural lumen of a vessel, showing a distal end portion of the vascular access device in a straight configuration.

FIG. 4E is a side view of a portion of the vascular access device of FIG. 4A positioned within the natural lumen of the vessel, showing the distal end portion in a curved configuration and a guidewire of the vascular access device passed through a wall of the vessel to form an aperture in the vessel wall.

FIG. 4F is a side view of a portion of the vascular access device of FIG. 4A positioned within the natural lumen of the vessel, showing a catheter of the vascular access device passed through the aperture in the vessel wall.

FIG. 4G is a side view of a portion of the vascular access device of FIG. 4A positioned within the natural lumen of the vessel, showing the catheter passed through the aperture in the vessel wall and a hemostatic connection formed between the catheter and the vessel wall.

FIG. 5A is a side view of a vascular access device in accordance with one or more embodiments of the disclosure.

FIG. 5B is a side view of the vascular access device of FIG. 5A and a guidewire, showing the guidewire passed through a vessel wall.

FIG. 5C is a side view of the vascular access device of FIG. 5A and the guidewire, showing a dilator and a catheter of the vascular access device passed through the vessel wall.

FIG. 5D is a side view of the vascular access device of FIG. 5A and the guidewire, showing coated regions of the catheter in an expanded state.

FIG. 5G is a bottom view of the vascular access device of FIG. 2S, showing a coated region of a catheter of the vascular access device.

FIG. 5H is a side view of the vascular access device of FIG. 2S, showing the coated region of the catheter.

FIG. 6A is a side view of a vascular access device in accordance with one or more embodiments of the disclosure.

FIG. 6B is a top view of the vascular access device of FIG. 6A.

FIG. 6C is an end view of the vascular access device of FIG. 6A, taken along line 6C-6C in FIG. 6A.

FIG. 6D is an end view of the vascular access device of FIG. 6A, taken along line 6D-6D in FIG. 6A.

FIG. 6E is a cross-sectional side view of the vascular access device of FIG. 6A, taken along line 6E-6E in FIG. 6B.

DETAILED DESCRIPTION

Figure 1J:
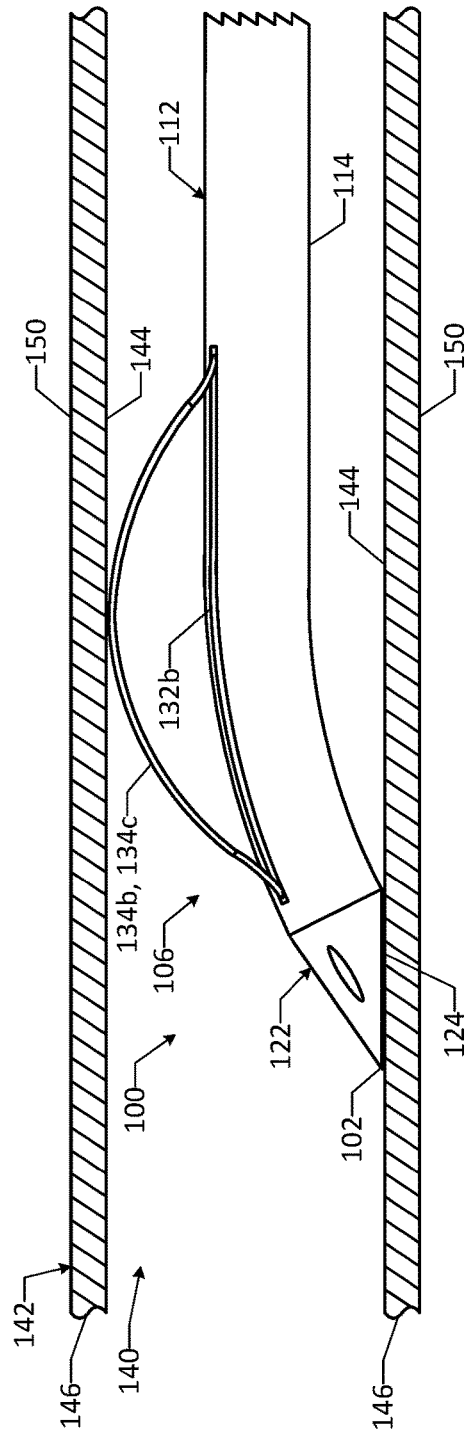
FIG. 1J is a side view of a portion of the vascular access device of FIG. 1A positioned within the natural lumen of the vessel, showing the distal end portion in the curved configuration and the deployable wires in the deployed configuration.

Improved vascular access devices and methods have been developed to provide access for performing cardiac interventional procedures on patients in need thereof. In particular, such access may be achieved by percutaneously inserting the vascular access device through the natural lumen of a vessel, forming a hemostatic connection between the vascular access device and an inner surface of a wall of the vessel, and forming an aperture through the vessel wall to access desired vasculature in a thoracic region of the patient. Operative instruments or other devices then may be passed through the vascular access device and the aperture in the vessel wall and into the thoracic region to perform a cardiac procedure on the desired vasculature. The vascular access devices disclosed herein advantageously may easily pass through the natural lumen of the vessel, may quickly and effectively form the hemostatic connection between the vascular access device and the inner surface of the vessel wall, and may provide a working lumen of sufficient size to allow operative instruments or other devices to be passed therethrough to perform a desired cardiac procedure on the patient. The vascular access devices also may allow a physician to easily assess the integrity of the hemostatic connection and the aperture formed through the vessel wall before, during, or after performing the desired cardiac procedure. Furthermore, the vascular access devices may allow sufficient blood flow to pass through the natural lumen of the vessel while the vascular access device is positioned therein. As a result, the vascular access devices and methods disclosed herein may allow physicians to easily and confidently perform various cardiac interventional procedures in a minimally invasive manner which does not require use of cardiopulmonary bypass.

As used herein, the term "patient" refers primarily to a human adult or child, but also may include other suitable mammalian animals, for example in a pre-clinical trial or in veterinary care.

The vascular access devices and methods disclosed herein build upon the devices and methods described in U.S. Pat. No. 8,663,321 to Crisco, which is incorporated by reference herein. Additionally, the vascular access devices and methods disclosed herein may be used in conjunction with or as a part of one or more of the devices, systems, and methods described in U.S. Provisional Patent Application Ser. No. 62/331,229 to Crisco, titled "Vascular Access Devices, Systems, and Methods," which is incorporated by reference herein.

Vascular Access Devices and Methods

FIGS. 1A-1M illustrate a vascular access device 100 (which also may be referred to as an "endovascular access device") configured to provide access for performing cardiac interventional procedures on patients in need thereof, in accordance with one or more embodiments of the disclosure. As described in detail below, the vascular access device 100 is configured to be percutaneously inserted through the natural lumen of a vessel of a patient, to form a hemostatic connection between the device 100 and an inner surface of a wall of the vessel, and to facilitate formation of an aperture through the vessel wall to provide access to desired vasculature in a thoracic region of the patient. The vascular access device 100 also may be configured to allow operative instruments or other devices to be passed through the device 100 to perform a desired cardiac procedure on the patient, to allow a physician to assess the integrity of the hemostatic connection and the aperture formed through the vessel wall before, during, or after performing the desired cardiac procedure, and to allow sufficient blood flow to pass through the natural lumen of the vessel while the device 100 is positioned therein.

As shown in FIG. 1A, the vascular access device 100 has an elongated shape including a distal end 102 (which also may be referred to as a "leading end") and a proximal end 104 (which also may be referred to as a "trailing end") positioned along a longitudinal axis $A_L$ of the device 100. The vascular access device 100 includes a distal end portion 106 extending from the distal end 102 toward the proximal end 104 along the longitudinal axis $A_L$, a proximal end portion 108 extending from the proximal end 104 toward the distal end 102 along the longitudinal axis $A_L$, and an intermediate portion 110 extending axially from the distal end portion 106 to the proximal end portion 108. It will be appreciated that part of the intermediate portion 110 of the vascular access device 100 is removed from view in FIG. 1A for purposes of illustrating the device 100. When the vascular access device 100 is used to provide access for performing a cardiac procedure on a patient, the distal end portion 106 and at least part of the intermediate portion 110 may be percutaneously inserted through the natural lumen of a vessel, while the proximal end portion 108 remains at least partially outside of the patient's body. In this manner, the proximal end portion 108 may be manipulated by a physician outside of the patient's body in order to position the distal end portion 106 at a desired location within the vessel lumen and form a hemostatic connection between the distal end portion 106 and the vessel wall, as described below.

The vascular access device 100 includes a catheter 112, which may extend axially from the distal end 102 to the proximal end 104 of the device 100. The catheter 112 may include a flexible shaft 114 (which also may be referred to as a "tube") configured to traverse the vessel lumen in which the vascular access device 100 is inserted. As shown, the shaft 114 may have an elongated tubular shape and a circular axial cross-sectional shape, although other shapes of the shaft 114 may be used. In some embodiments, as shown, a longitudinal axis of the catheter 112 is coaxial with the longitudinal axis $A_L$ of the device 100. The catheter 112 may include a primary lumen 116 (which also may be referred to as a "working lumen" or an "access lumen") extending therethrough from the distal end 102 to the proximal end 104 of the device 100. As described below, the primary lumen 116 may be used to facilitate insertion and positioning of the vascular access device 100 within the vessel lumen via a guidewire and/or a dilator, to facilitate formation of an aperture through the vessel wall, and to pass operative instruments or other devices through the device 100 and the aperture to perform a desired cardiac procedure on the patient. As shown, the primary lumen 116 may have a cylindrical shape and a circular axial cross-sectional shape, although other shapes of the primary lumen 116 may be used. In some embodiments, as shown, a longitudinal axis of the primary lumen 116 is radially offset from the longitudinal axis of the catheter 112 and the longitudinal axis $A_L$ of the device 100. In this manner, a wall thickness of the catheter 112 may vary along the circumference of the catheter 112, as shown. In some embodiments, the catheter 112 is formed of a biocompatible polymer, although other suitable materials may be used in other embodiments. For example, the catheter 112 may be formed of a polyether block amide (PEBA), such as PEBAX®, a thermoplastic urethane (TPU), such as PELLETHANE®, or a nylon.

In some embodiments, as shown, the catheter 112 includes a liner 118 positioned within the lumen of the shaft 114. The liner 118 may have an elongated tubular shape and a circular axial cross-sectional shape, and the liner 118 may define the primary lumen 116 of the catheter 112 (i.e., the lumen of the liner 118 may be the primary lumen 116 of the catheter 112). In other embodiments, the shaft 114 may define the primary lumen 116 of the catheter 112 (i.e., the lumen of the shaft 114 may be the primary lumen 116 of the catheter 112). In some embodiments, as shown, the catheter 112 also includes a reinforcement structure 120 positioned within the lumen of the shaft 114 and radially between the shaft 114 and the liner 118. The reinforcement structure 120 may have an elongated tubular shape and a circular axial cross-sectional shape, and the reinforcement structure 120 may include one or more wires arranged in a braided or coiled manner and configured to enhance the integrity of the catheter 112. In some embodiments, the reinforcement structure 120 extends along the entire length of the catheter 112. In other embodiments, the reinforcement structure 120 extends along only a portion of the length of the catheter 112. In some embodiments, the liner 118 is formed of a biocompatible polymer, although other suitable materials may be used in other embodiments. For example, the liner 118 may be formed of a polytetrafluoroethylene (PTFE), a perfluoroalkoxy alkane (PFA), a fluorinated ethylene propylene (FEP), another fluoropolymer, a polyimide (PI), or a polyethylene (PE), such as a high-density polyethylene (HDPE), a low-density polyethylene (LDPE), or a medium-density polyethylene (MDPE). In some embodiments, the reinforcement structure 120 is formed of a biocompatible metal or a biocompatible polymer, although other suitable materials may be used in other embodiments. For example, the reinforcement structure 120 may be formed of a stainless steel, a polyether ether ketone (PEEK), a nylon, or KEVLAR®.

The shaft 114 of the catheter 112 may include a distal tip portion 122 positioned about the distal end 102 of the vascular access device 100. As shown, the external surface of the distal tip portion 122 may be tapered such that the external surface tapers radially inward in a direction from the proximal end to the distal end of the distal tip portion 122. The distal tip portion 122 also may be beveled, as shown, such that a distal edge 124 of the distal tip portion 122 is angled at an acute angle relative to the longitudinal axis $A_L$ of the device 100. In some embodiments, the acute angle between the distal edge 124 and the longitudinal axis $A_L$ of the device 100 is between about 15 degrees and about 45 degrees.

As shown in FIGS. 1A-1D, the catheter 112 may include a number of secondary lumens 126 extending therethrough, in addition to the primary lumen 116. In particular, the catheter 112 may include a first secondary lumen 126a (which also may be referred to as a "fixed wire lumen"), a second secondary lumen 126b (which also may be referred to as a "deployable wire lumen"), a third secondary lumen 126c (which also may be referred to as a "deployable wire lumen"), a fourth secondary lumen 126d, a fifth secondary lumen 126e, a sixth secondary lumen 126f (which also may be referred to as an "internal thru lumen"), and a seventh secondary lumen 126g (which also may be referred to as a "external thru lumen"). The secondary lumens 126 may be defined in the shaft 114 of the catheter 112 and arranged in a circumferential array, as shown in FIG. 1C, such that the secondary lumens 126 are circumferentially spaced apart from one another and radially spaced apart from the primary lumen 116 and the external surface of the shaft 114. As shown, the secondary lumens 126 each may have a cylindrical shape and a circular axial cross-sectional shape, although other shapes of the secondary lumens 126 may be used. Although the illustrated embodiment includes seven secondary lumens 126, it will be understood that any number of the secondary lumens 126 may be used in other embodiments. In some embodiments, one or more of the secondary lumens 126 has a liner positioned therein. In some embodiments, the secondary lumen liners are formed of a biocompatible polymer, although other suitable materials may be used in other embodiments. For example, the secondary lumen liners may be formed of a polyimide (PI), a polytetrafluoroethylene (PTFE), a perfluoroalkoxy alkane (PFA), a fluorinated ethylene propylene (FEP), another fluoropolymer, or a polyethylene (PE), such as a high-density polyethylene (HDPE), a low-density polyethylene (LDPE), or a medium-density polyethylene (MDPE).

The secondary lumens 126 each may extend axially through the catheter 112 and parallel to the longitudinal axis $A_L$ of the device 100, as shown. In some embodiments, the respective distal ends of the first secondary lumen 126a, the second secondary lumen 126b, the third secondary lumen 126c, the fourth secondary lumen 126d, and the fifth secondary lumen 126e are closed and positioned within the wall of the shaft 114. In some such embodiments, the closed distal ends of the first secondary lumen 126a, the second secondary lumen 126b, the third secondary lumen 126c, the fourth secondary lumen 126d, and the fifth secondary lumen 126e are positioned at or near the proximal end of the distal tip portion 122 of the shaft 114, although other positions of the closed distal ends may be used in other embodiments. In some embodiments, the respective proximal ends of the first secondary lumen 126a, the second secondary lumen 126b, the third secondary lumen 126c, the fourth secondary lumen 126d, and the fifth secondary lumen 126e are open at respective openings defined in the proximal end of the shaft 114. In other embodiments, the respective proximal ends of the first secondary lumen 126a, the second secondary lumen 126b, the third secondary lumen 126c, the fourth secondary lumen 126d, and the fifth secondary lumen 126e may be closed and positioned within the wall of the shaft 114.

As shown, the respective distal ends of the sixth secondary lumen 126f and the seventh secondary lumen 126g may be open at respective openings defined in the distal tip portion 122 of the shaft 114. In particular, the sixth secondary lumen 126f may be in fluid communication with an opening 128 (which also may be referred to as an "exit opening" or an "internal exit opening") that is defined in the internal surface of the distal tip portion 122 and in fluid communication with the primary lumen 116 of the catheter 112. The seventh secondary lumen 126g may be in fluid communication with an opening 130 (which also may be referred to as an "exit opening" or an "external exit opening") that is defined in the external surface of the distal tip portion 122. In some embodiments, the respective proximal ends of the sixth secondary lumen 126f and the seventh secondary lumen 126g are open at respective openings (which also may be referred to an "entry openings") that are defined in the proximal end of the shaft 114. In other embodiments, the respective proximal ends of the sixth secondary lumen 126f and the seventh secondary lumen 126g are open at respective openings defined the wall of the shaft 114 near the proximal end of the shaft 114. As described below, the sixth secondary lumen 126f and the seventh secondary lumen 126g may be used to deliver materials through the catheter 112 and out of the respective openings 128, 130.

As shown in FIGS. 1A and 1D, the catheter 112 may include a number of deployment openings 132 each defined in the external surface of the shaft 114 and in fluid communication with one of the secondary lumens 126. In particular, the catheter 112 may include a first deployment opening 132a defined in the external surface of the shaft 114 and in fluid communication with the second secondary lumen 126b, and a second deployment opening 132b defined in the external surface of the shaft 114 and in fluid communication with the third secondary lumen 126c. The deployment openings 132 may be circumferentially spaced apart from one another and arranged in a circumferential array, as shown in FIG. 1D, and may extend inwardly from the external surface of the shaft 114 to the second secondary lumen 126b and the third secondary lumen 126c, respectively. As shown, the deployment openings 132 may extend axially along the shaft 114 and parallel to the longitudinal axis $A_L$ of the device 100, and each deployment opening 132 may have an axial length that is less than the axial length of the shaft 114. The deployment openings 132 each may have an elongated slot shape, as shown, although other shapes of the deployment openings 132 may be used. Although the illustrated embodiment includes two deployment openings 132, it will be understood that any number of the deployment openings 132 may be used in other embodiments.

As shown in FIGS. 1C-1G, the vascular access device 100 includes a number of wires 134 secured to the catheter 112 and configured to facilitate positioning of the distal end portion 106 of the device 100 relative to the vessel in order to form a hemostatic connection between the device 100 and an inner surface of the vessel wall. In particular, the vascular access device 100 includes a first wire 134a (which also may be referred to as a "fixed wire" or a "non-deployable wire"), a second wire 134b (which also may be referred to as a "deployable wire"), and a third wire 134c (which also may be referred to as a "deployable wire"). As shown in FIGS. 1C and 1D, the first wire 134a may be positioned within the first secondary lumen 126a. In particular, the first wire 134a may be fixedly secured within the first secondary lumen 126a, such that the first wire 134a is retained within the wall of the shaft 114 during use of the vascular access device 100. In some embodiments, the first wire 134a is formed of a shape memory material, such as a shape memory metal or a shape memory polymer. For example, the first wire 134a may be formed of nitinol. In this manner, the first wire 134a may have a natural undeformed shape, but may be deformed to a different shape, after which the first wire 134a may return to its natural undeformed shape absent opposing forces prohibitively restraining the first wire 134a from doing so. In some embodiments, the first wire 134a has a natural undeformed shape that is curved in accordance with the curved shape of the distal end portion 106 of the vascular access device 100 shown in FIG. 1I, but may be deformed to have a straight shape in accordance with the straight shape of the distal end portion 106 of the vascular access device 100 shown in FIG. 1A. In this manner, the first wire 134a may be configured to cause the distal end portion 106 of the vascular access device 100 to assume the curved shape shown in FIG. 1I absent opposing forces prohibitively restraining the distal end portion 106 from assuming the curved shape.

As shown in FIGS. 1C and 1D, the second wire 134b may be positioned at least partially within the second secondary lumen 126b, and the third wire 134c may be positioned at least partially within the third secondary lumen 126c. The second wire 134b and the third wire 134c each may be configured to move between a first configuration (which also may be referred to as a "delivery configuration"), as shown in FIGS. 1A-1D, and a second configuration (which also may be referred to as a "deployed configuration"), as shown in FIGS. 1E-1G. When the second wire 134b and the third wire 134c are in the first configuration, the second wire 134b may be received within the second secondary lumen 126b and/or the first deployment opening 132a without extending outward beyond the external surface of the shaft 114, and the third wire 134c may be received within the third secondary lumen 126c and/or the second deployment opening 132b without extending outward beyond the external surface of the shaft 114, as shown. When the second wire 134b and the third wire 134c are in the second configuration, the second wire 134b may be received partially within the second secondary lumen 126b and/or the first deployment opening 132a and may extend partially outward beyond the external surface of the shaft 114, and the third wire 134c may be received partially within the third secondary lumen 126c and/or the second deployment opening 132b and may extend partially outward beyond the external surface of the shaft 114. In this manner, the extended portions of the second wire 134b and the third wire 134c may be configured to engage the inner surface of the vessel wall when the second wire 134b and the third wire 134c are in the second configuration. In some embodiments, the second wire 134b and the third wire 134c each are formed of a shape memory material, such as a shape memory metal or a shape memory polymer. For example, the second wire 134b and the third wire 134c each may be formed of nitinol. In this manner, the second wire 134b and the third wire 134c each may have a natural undeformed shape, but may be deformed to a different shape, after which the wires 134b, 134c may return to their respective natural undeformed shapes absent opposing forces prohibitively restraining the wires 134b, 134c from doing so. In some embodiments, the second wire 134b and the third wire 134c each have a natural undeformed shape that is curved, as shown in FIGS. 1E-1G, but may be deformed to have a straight shape in accordance with the straight shape of the distal end portion 106 of the vascular access device 100 shown in FIG. 1A. In this manner, the second wire 134b and the third wire 134c each may be configured to assume the curved second configuration absent opposing forces prohibitively restraining the wires 134b, 134c from doing so.

FIGS. 1H-1M illustrate an example method of using the vascular access device 100 to provide access for performing a cardiac interventional procedure on a patient. Initially, the vascular access device 100 may be percutaneously inserted into the patient through a vascular access site formed in an artery, such as a femoral artery. With the proximal end portion 108 of the device 100 outside of the patient, the physician may manipulate the proximal end portion 108 in order to advance the distal end portion 106 of the device 100 through the vasculature and position the distal end portion 106 at a desired location within a natural lumen 140 of a desired vessel 142, as shown in FIG. 1I1. In some embodiments, as shown, the vascular access device 100 is advanced over a guidewire 160 to facilitate guiding the distal end portion 106 of the device 100 through the vasculature and positioning the distal end portion 106 at the desired location within vessel 142. Additionally, in some embodiments, as shown, a dilator 162 is positioned within the primary lumen 116 of the catheter 112 and advanced along with the distal end portion 106 of the device 100 through the vasculature. When the dilator 162 is positioned within the primary lumen 116 of the catheter 112, the dilator 162 may maintain the first wire 134a in its deformed, straight shape (i.e., the dilator 162 may restrain the first wire 134a from assuming its natural undeformed, curved shape), such that the distal end portion 106 of the device 100 is maintained in its straight configuration, as shown in FIG. 1I1.

After the distal end portion 106 of the device 100 is positioned at the desired location within the natural lumen 140 of the vessel 142, the guidewire 160 and the dilator 162 may be removed from the primary lumen 116 of the catheter 112 or at least partially retracted (i.e., moved proximally with respect to the catheter 112) within the primary lumen 116 such that the guidewire 160 and the dilator 162 are not positioned within the distal end portion 106. Upon such removal or retraction of the guidewire 160 and the dilator 162, the first wire 134a may assume its natural undeformed, curved shape, thereby causing the distal end portion 106 to assume its curved configuration, as shown in FIG. 1I. When the distal end portion 106 assumes its curved configuration, a first part of the distal end portion 106 may engage a first part of an inner surface 144 of a wall 146 of the vessel 140, and a second part of the distal end portion 106 may engage a circumferentially opposite second part of the inner surface 144 of the wall 146 of the vessel 140. In particular, the distal edge 124 of the distal tip portion 122 may at least partially engage the first part of the inner surface 144 of the vessel wall 146, and the external surface of the shaft 114 may at least partially engage the second part of the inner surface 144 of the vessel wall 146, as shown in FIG. 1I.

After the distal end portion 106 assumes its curved configuration, the second wire 134b and the third wire 134c may be deployed from the catheter 112, as shown in FIG. 1J. In other words, the second wire 134b and the third wire 134c may be moved or allowed to move from their straight first configuration to their curved second configuration, as shown. In some embodiments, the second wire 134b and the third wire 134c are moved from their straight first configuration to their curved second configuration by manipulating respective proximal ends of the wires 134b, 134c, or intermediate components attached to the wires 134b, 134c, positioned about the proximal end 104 of the vascular access device 100. In other embodiments, the second wire 134b and the third wire 134c are allowed to move from their straight first configuration to their curved second configuration by removing or retracting a sheath positioned over the deployment openings 132 of the catheter 112. Still other components or mechanisms may be used to move the second wire 134b and the third wire 134c or allow the wires 134b, 134c to move from their straight first configuration to their curved second configuration in other embodiments. When the second wire 134b and the third wire 134c are in their curved second configuration, the wires 134b, 134c may at least partially engage the first part of the inner surface 144 of the vessel wall 146 and may bias the distal end portion 106 of the device 100 toward the second part of the inner surface 144 of the vessel wall 146. As shown in FIG. 1J, the biasing force provided by the second wire 134b and the third wire 134c may cause the external surface of the shaft 114 to disengage the first part of the inner surface 144 of the vessel wall 146 and the curvature of the distal end portion 106 to decrease. Additionally, the biasing force provided by the second wire 134b and the third wire 134c may cause the entire distal edge 124 of the distal tip portion 122 to fully engage the first part of the inner surface 144 of the vessel wall 146, such that a hemostatic connection is formed between the distal edge 124 and the inner surface 144 of the vessel wall 146, as shown. Furthermore, the biasing force provided by the second wire 134b and the third wire 134c and the resulting engagement between the wires 134b, 134c and the first part of the inner surface 144 of the vessel wall 146 and between the distal edge 124 and the second part of the inner surface 144 of the vessel wall 146 may secure the position of the distal end portion 106 of the device 100 within the vessel lumen 140.

Figure 1K:
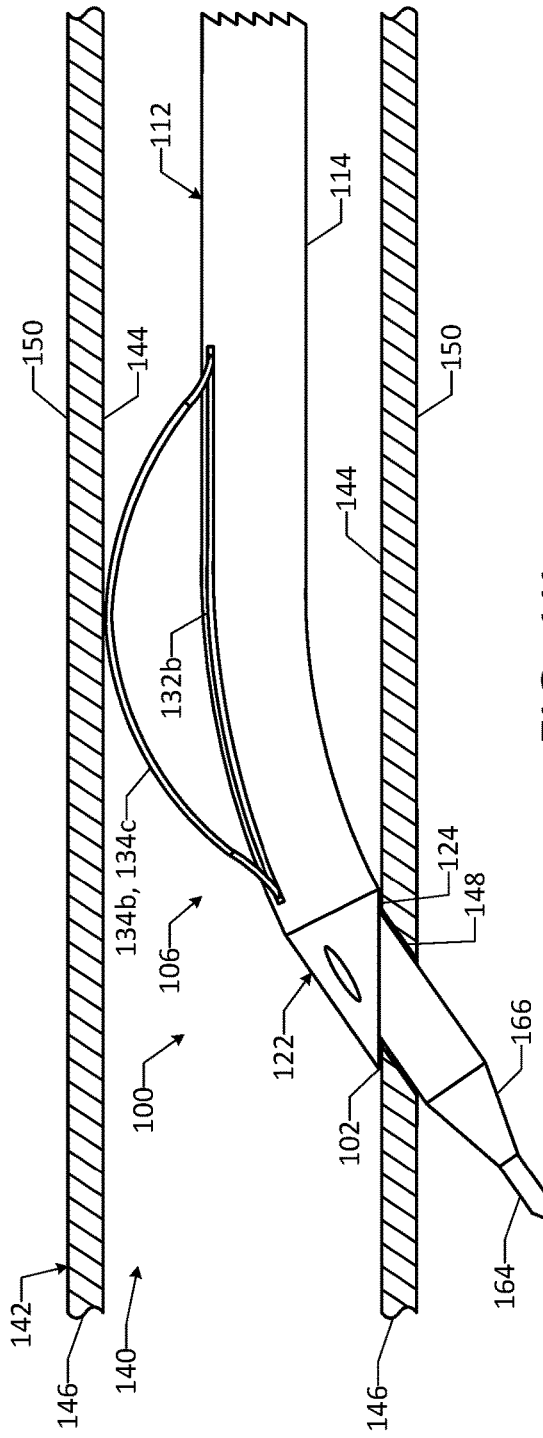
FIG. 1K is a side view of a portion of the vascular access device of FIG. 1A positioned within the natural lumen of the vessel, showing a guidewire and a dilator passed through the vascular access device and a wall of the vessel to form an aperture in the vessel wall.

After the hemostatic connection is formed between the distal edge 124 of the distal tip portion 122 and the inner surface 144 of the vessel wall 146, a guidewire 164 and/or a dilator 166 may be advanced through the primary lumen 116 of the catheter 112 and through the vessel wall 146, as shown in FIG. 1K. The guidewire 164 and/or the dilator 166 may form an aperture 148 in the vessel wall 146 extending from the inner surface 144 to an outer surface 150 of the vessel wall 146, while the hemostatic connection is maintained between the distal edge 124 of the distal tip portion 122 and the inner surface 144 of the vessel wall 146. In this manner, the hemostatic connection may surround the aperture 148, thereby preventing or at least inhibiting blood from flowing out of the vessel lumen 140 through the aperture 148 and preventing or at least inhibiting body fluids or other materials from entering the vessel lumen 140 through the aperture 148. In some embodiments, the guidewire 164 is different than the guidewire 160. For example, the guidewire 164 may have a sharp distal tip, and the guidewire 160 may have a blunt or rounded distal tip. In other embodiments, the guidewire 164 may be the same as the guidewire 160 (i.e., the guidewire 160 may be used to guide the distal end portion 106 of the device 100 to the desired location in the vessel lumen 140 and to puncture the vessel wall 146 to form the aperture 148). In some embodiments, the dilator 166 is different than the dilator 160. For example, the distal end portion of the dilator 166 may have a different taper angle or length as compared to the taper angle or length of the distal end portion of the dilator 162. In other embodiments, the dilator 166 may be the same as the dilator 162 (i.e., the dilator 162 may be used to guide the distal end portion 106 of the device 100 to the desired location in the vessel lumen 140 and to dilate the vessel wall 146 to form the aperture 148).

After the aperture 148 is formed in the vessel wall 146, the guidewire 164 and the dilator 166 may be retracted and removed from the primary lumen 116 of the catheter 112, while the hemostatic connection is maintained between the distal edge 124 of the distal tip portion 122 and the inner surface 144 of the vessel wall 146, as shown in FIG. 1L. After removal of the guidewire 164 and the dilator 166 from the primary lumen 116, the physician may assess the integrity of the hemostatic connection and the aperture 148 in the vessel wall 146. In particular, a first fluid may be injected through the sixth secondary lumen 126f of the catheter 112 and out of the opening 128. The first fluid may include a first contrast medium that is visible under medical imaging, and thus the physician may observe the flow of the first fluid to assess the integrity of the hemostatic connection and/or the aperture 148. In a similar manner, a second fluid may be injected through the seventh secondary lumen 126g of the catheter 112 and out of the opening 130. The second fluid may include a second contrast medium that is visible under medical imaging, and thus the physician may observe the flow of the second fluid to assess the integrity of the hemostatic connection and/or the aperture 148. It will be appreciated that this technique of assessing the integrity of the hemostatic connection and/or the aperture 148 may be carried out at any point during the method of using the vascular access device 100 to provide access. For example, this technique may be carried out before, during, or after the aperture 148 is formed in the vessel wall 146.

After the aperture 148 is formed in the vessel wall 146, a cardiac interventional procedure may be performed through the vascular access device 100 and through the aperture 148, while the hemostatic connection is maintained between the distal edge 124 of the distal tip portion 122 and the inner surface 144 of the vessel wall 146. In particular, as shown in FIG. 1M, one or more operative instruments or devices 168 may be passed through the primary lumen 116 of the catheter 112 and the aperture 148 in the vessel wall 146 and into the thoracic cavity of the patient to perform a desired cardiac procedure on the desired vasculature. Upon completion of the cardiac procedure, the aperture 148 in the vessel wall 146 may be closed, and the vascular access device 100 may be removed from the patient.

In some embodiments, the vascular access device 100 may be used in combination with other devices to perform a desired cardiac procedure. For example, the vascular access device 100 may be used in combination with one of the puncturable balloon catheter devices described in U.S. Provisional Patent Application Ser. No. 62/331,229 to Crisco to perform a desired cardiac procedure, such as a coronary bypass procedure, as described therein. In such uses, the vascular access device 100 may be used inside of the vessel 142 in the manner described above, and the puncturable balloon catheter device may be used outside of the vessel 142 in the extravascular space, in the soft tissue of a limb of other anatomical locations including the chest and the pericardium, for the purpose of creating space for delivery of catheters, wires, delivery systems, and bypass conduits for the purposes of revascularization. Moreover, the vascular access device 100 may be used instead of the vascular access devices described in U.S. Provisional Patent Application Ser. No. 62/331,229 to Crisco to perform any of the cardiac procedures described therein.

FIGS. 2A-2V illustrate a vascular access device 200 (which also may be referred to as an "endovascular access device") configured to provide access for performing cardiac interventional procedures on patients in need thereof, in accordance with one or more embodiments of the disclosure. As described in detail below, the vascular access device 200 is configured to be percutaneously inserted through the natural lumen of a vessel of a patient, to form a hemostatic connection between the device 200 and an inner surface of a wall of the vessel, and to facilitate formation of an aperture through the vessel wall to provide access to desired vasculature in a thoracic region of the patient. The vascular access device 200 also may be configured to allow operative instruments or other devices to be passed through the device 200 to perform a desired cardiac procedure on the patient, to allow a physician to assess the integrity of the hemostatic connection and the aperture formed through the vessel wall before, during, or after performing the desired cardiac procedure, and to allow sufficient blood flow to pass through the natural lumen of the vessel while the device 200 is positioned therein.

As shown in FIGS. 2A-2C, the vascular access device 200 has an elongated shape including a distal end 202 (which also may be referred to as a "leading end") and a proximal end 204 (which also may be referred to as a "trailing end") positioned along a longitudinal axis $A_L$ of the device 200. The vascular access device 200 includes a distal end portion 206 extending from the distal end 202 toward the proximal end 204 along the longitudinal axis $A_L$, a proximal end portion 208 extending from the proximal end 204 toward the distal end 202 along the longitudinal axis $A_L$, and an intermediate portion 210 extending axially from the distal end portion 206 to the proximal end portion 208. It will be appreciated that part of the intermediate portion 210 of the vascular access device 200 is removed from view in FIGS. 2A-2C for purposes of illustrating the device 200. When the vascular access device 200 is used to provide access for performing a cardiac procedure on a patient, the distal end portion 206 and at least part of the intermediate portion 210 may be percutaneously inserted through the natural lumen of a vessel, while the proximal end portion 208 remains at least partially outside of the patient's body. In this manner, the proximal end portion 208 may be manipulated by a physician outside of the patient's body in order to position the distal end portion 206 at a desired location within the vessel lumen and form a hemostatic connection between the distal end portion 206 and the vessel wall, as described below.

The vascular access device 200 includes a catheter 212, which may extend axially from the distal end 202 to the proximal end 204 of the device 200. The catheter 212 may include a flexible shaft 214 (which also may be referred to as a "tube") configured to traverse the vessel lumen in which the vascular access device 200 is inserted. As shown, the shaft 214 may have an elongated tubular shape and a circular axial cross-sectional shape, although other shapes of the shaft 214 may be used. In some embodiments, as shown, a longitudinal axis of the catheter 212 is coaxial with the longitudinal axis $A_L$ of the device 200. The catheter 212 may include a primary lumen 216 (which also may be referred to as a "working lumen" or an "access lumen") extending therethrough from the proximal end 204 of the device 200 to an access opening 218 defined in a side wall of the shaft 214, as shown. As described below, the primary lumen 216 may be used to facilitate insertion and positioning of the vascular access device 200 within the vessel lumen via a guidewire and/or a dilator, to facilitate formation of an aperture through the vessel wall, and to pass operative instruments or other devices through the device 200 and the aperture to perform a desired cardiac procedure on the patient. As shown, the primary lumen 216 may have a cylindrical shape and a circular axial cross-sectional shape, although other shapes of the primary lumen 216 may be used. In some embodiments, as shown, a longitudinal axis of the primary lumen 216 is radially offset from the longitudinal axis of the catheter 212 and the longitudinal axis $A_L$ of the device 200. In this manner, a wall thickness of the catheter 212 may vary along the circumference of the catheter 212, as shown. The catheter 212 also may include a guidewire lumen 220 (which also may be referred to as a "guiding lumen" or a "distal lumen") extending therethrough from the distal end 202 of the device 200 to a lumen transition portion 222 positioned axially between the guidewire lumen 220 and the primary lumen 216, as shown in FIG. 2D. The lumen transition portion 222 may be contoured to provide a smooth transition from the larger-diameter primary lumen 216 to the smaller-diameter guidewire lumen 220, as shown. The guidewire lumen 220 may include a first portion 220a and a second portion 220b, and a seal 224 (which also may be referred to as a "guidewire seal") may be positioned axially between the first portion 220a and the second portion 220b. As shown, the longitudinal axis of the first portion 220a of the guidewire lumen 220 may be coaxial with the longitudinal axis of the catheter 212 and the longitudinal axis $A_L$ of the device 200 and radially offset from the longitudinal axis of the primary lumen 216, and the longitudinal axis of the second portion 220b of the guidewire lumen 220 may be angled at an acute angle relative to the longitudinal axis $A_L$ of the device 200. As shown, the first portion 220a and the second portion 220b of the guidewire lumen 220 each may have a cylindrical shape and a circular axial cross-sectional shape, although other shapes of the portions 220a, 220b may be used. The seal 224 may be configured to form a hemostatic seal around a guidewire when the guidewire is positioned within the guidewire lumen 220, and to close to form a hemostatic seal itself when no guidewire is positioned within the guidewire lumen 220. In some embodiments, the catheter 212 is formed of a biocompatible polymer, although other suitable materials may be used in other embodiments. For example, the catheter 212 may be formed of a polyether block amide (PEBA), such as PEBAX®, a thermoplastic urethane (TPU), such as PELLETHANE®, or a nylon. In some embodiments, the seal 224 is formed of a biocompatible polymer, although other suitable materials may be used in other embodiments. For example, the seal 224 may be formed of a polyether block amide (PEBA), such as PEBAX®, a thermoplastic urethane (TPU), such as PELLETHANE®, or a nylon.

In some embodiments, as shown, the catheter 212 includes a liner 228 positioned within the lumen of the shaft 214. The liner 228 may have an elongated tubular shape and a circular axial cross-sectional shape, and the liner 228 may define the primary lumen 216 of the catheter 212 (i.e., the lumen of the liner 228 may be the primary lumen 216 of the catheter 212) along at least a portion of the axial length of the primary lumen 216. In some embodiments, the shaft 214 may define the primary lumen 216 of the catheter 212 (i.e., the lumen of the shaft 214 may be the primary lumen 216 of the catheter 212) along at least a portion of the axial length of the primary lumen 216. In some embodiments, as shown, the catheter 212 also includes a reinforcement structure 230 positioned within the lumen of the shaft 214 and radially between the shaft 214 and the liner 228. The reinforcement structure 230 may have an elongated tubular shape and a circular axial cross-sectional shape, and the reinforcement structure 230 may include one or more wires arranged in a braided or coiled manner and configured to enhance the integrity of the catheter 212. In some embodiments, as shown, the reinforcement structure 230 extends along only a portion of the axial length of the primary lumen 216. In other embodiments, the reinforcement structure 230 extends along the entire length of the primary lumen 216. In some embodiments, the liner 228 is formed of a biocompatible polymer, although other suitable materials may be used in other embodiments. For example, the liner 228 may be formed of a polytetrafluoroethylene (PTFE), a perfluoroalkoxy alkane (PFA), a fluorinated ethylene propylene (FEP), another fluoropolymer, a polyimide (PI), or a polyethylene (PE), such as a high-density polyethylene (HDPE), a low-density polyethylene (LDPE), or a medium-density polyethylene (HDPE). In some embodiments, the reinforcement structure 230 is formed of a biocompatible metal or a biocompatible polymer, although other suitable materials may be used in other embodiments. For example, the reinforcement structure 230 may be formed of a stainless steel, a polyether ether ketone (PEEK), a nylon, or KEVLAR®.

The shaft 214 of the catheter 212 may include a distal tip portion 232 (which also may be referred to as a "dilator tip portion") positioned about the distal end 202 of the vascular access device 200. As shown, the external surface of the distal tip portion 232 may be tapered such that the external surface tapers radially inward in a direction from the proximal end to the distal end of the distal tip portion 232. In this manner, the distal tip portion 232 may facilitate guiding of the distal end portion 206 of the vascular access device 200 through the natural lumen of a vessel in which the device 200 is inserted. As shown in FIG. 2D, the first portion 220a of the guidewire lumen 220 and the seal 224 each may be positioned at least partially within the distal tip portion 232 of the shaft 214.

As shown in FIGS. 2D and 2F, the catheter 212 may include a number of secondary lumens 236 extending therethrough, in addition to the primary lumen 216 and the guidewire lumen 220. In particular, the catheter 212 may include a first secondary lumen 236a (which also may be referred to as a "deployable wire lumen"), a second secondary lumen 236b (which also may be referred to as a "deployable wire lumen"), and a third secondary lumen 236c (which also may be referred to as a "deployable wire lumen"). The secondary lumens 236 may be defined in the shaft 214 of the catheter 212 and arranged in a circumferential array, as shown in FIG. 2F, such that the secondary lumens 236 are circumferentially spaced apart from one another and radially spaced apart from the primary lumen 216, the guidewire lumen 220, and the external surface of the shaft 214. As shown, the secondary lumens 236 each may have a cylindrical shape and a circular axial cross-sectional shape, although other shapes of the secondary lumens 236 may be used. Although the illustrated embodiment includes three secondary lumens 236, it will be understood that any number of the secondary lumens 236 may be used in other embodiments.

The secondary lumens 236 each may extend axially through the catheter 212 and parallel to the longitudinal axis $A_L$ of the device 200, as shown. In some embodiments, the respective distal ends of the first secondary lumen 236a, the second secondary lumen 236b, and the third secondary lumen 236c are closed and positioned within the wall of the shaft 214. In some such embodiments, the closed distal ends of the first secondary lumen 236a, the second secondary lumen 236b, and the third secondary lumen 236c are positioned at or near the proximal end of the distal tip portion 232 of the shaft 214, although other positions of the closed distal ends may be used in other embodiments. In some embodiments, the respective proximal ends of the first secondary lumen 236a, the second secondary lumen 236b, and the third secondary lumen 236c are open at respective openings defined in the proximal end of the shaft 214. In other embodiments, the respective proximal ends of the first secondary lumen 236a, the second secondary lumen 236b, and the third secondary lumen 236c are closed and positioned within the wall of the shaft 214. In some embodiments, one or more of the secondary lumens 236 has a liner positioned therein. In some embodiments, the secondary lumen liners are formed of a biocompatible polymer, although other suitable materials may be used in other embodiments. For example, the secondary lumen liners may be formed of a polyimide (PI), a polytetrafluoroethylene (PTFE), a perfluoroalkoxy alkane (PFA), a fluorinated ethylene propylene (FEP), another fluoropolymer, or a polyethylene (PE), such as a high-density polyethylene (HDPE), a low-density polyethylene (LDPE), or a medium-density polyethylene (MDPE).

As shown in FIGS. 2A, 2B, 2D, and 2G, the catheter 212 may include a number of deployment openings 242 each defined in the external surface of the shaft 214 and in fluid communication with one of the secondary lumens 236. In particular, the catheter 212 may include a first deployment opening 242a defined in the external surface of the shaft 214 and in fluid communication with the first secondary lumen 236a, a second deployment opening 242b defined in the external surface of the shaft 214 and in fluid communication with the second secondary lumen 236b, and a third deployment opening 242c defined in the external surface of the shaft 214 and in fluid communication with the third secondary lumen 236c. The deployment openings 242 may be circumferentially spaced apart from one another and arranged in a circumferential array, as shown in FIGS. 2B and 2G, and may extend inwardly from the external surface of the shaft 214 to the respective secondary lumens 236. As shown, the deployment openings 242 may extend axially along the shaft 214 and parallel to the longitudinal axis $A_L$ of the device 200, and each deployment opening 242 may have an axial length that is less than the axial length of the shaft 214. The deployment openings 242 each may have an elongated slot shape, as shown, although other shapes of the deployment openings 242 may be used. Although the illustrated embodiment includes three deployment openings 242, it will be understood that any number of the deployment openings 242 may be used in other embodiments.

As shown in FIGS. 2D and 2F-2J, the vascular access device 200 includes a number of wires 244 secured to the catheter 212 and configured to facilitate positioning of the distal end portion 206 of the device 200 relative to the vessel in order to form a hemostatic connection between the device 200 and an inner surface of the vessel wall. In particular, the vascular access device 200 includes a first wire 244a (which also may be referred to as a "deployable wire"), a second wire 244b (which also may be referred to as a "deployable wire"), and a third wire 244c (which also may be referred to as a "deployable wire"). As shown in FIGS. 2D, 2F, and 2G, the first wire 244a may be positioned at least partially within the first secondary lumen 236a and at least partially within the first deployment opening 242a, the second wire 244b may be positioned at least partially within the second secondary lumen 236b and at least partially within the second deployment opening 242b, and the third wire 244c may be positioned at least partially within the third secondary lumen 236c at least partially within the third deployment opening 242c. The wires 244 each may be configured to move between a first configuration (which also may be referred to as a "delivery configuration"), as shown in FIGS. 2D, 2F, and 2G, and a second configuration (which also may be referred to as a "deployed configuration"), as shown in FIGS. 2H-2J. When the wires 244 are in the first configuration, the first wire 244a may be received partially within the first secondary lumen 236a and partially within the first deployment opening 242a without extending outward beyond the external surface of the shaft 214, the second wire 244b may be received partially within the second secondary lumen 236b and partially within the second deployment opening 242b without extending outward beyond the external surface of the shaft 214, and the third wire 244c may be received partially within the third secondary lumen 236c and partially within the third deployment opening 242c without extending outward beyond the external surface of the shaft 214. When the wires 244 are in the second configuration, the first wire 244a may be received partially within the first secondary lumen 236a and partially within the first deployment opening 242a and may extend partially outward beyond the external surface of the shaft 214, the second wire 244b may be received partially within the second secondary lumen 236b and partially within the second deployment opening 242b and may extend partially outward beyond the external surface of the shaft 214, and the third wire 244c may be received partially within the third secondary lumen 236c and partially within the third deployment opening 242c and may extend partially outward beyond the external surface of the shaft 214. In this manner, the extended portions of the wires 244 may be configured to engage the inner surface of the vessel wall when the wires 244 are in the second configuration. In some embodiments, the wires 244 each are formed of a shape memory material, such as a shape memory metal or a shape memory polymer. For example, the wires 244 each may be formed of nitinol. In this manner, the wires 244 each may have a natural undeformed shape, but may be deformed to a different shape, after which the wires 244 may return to their respective natural undeformed shapes absent opposing forces prohibitively restraining the wires 244 from doing so. In some embodiments, the wires 244 each have a natural undeformed shape that is curved, as shown in FIGS. 2H-2J, but may be deformed to have a substantially straight shape, as shown in FIG. 2D. In this manner, the wires 244 each may be configured to assume the curved second configuration absent opposing forces prohibitively restraining the wires 244 from doing so.

Figure 2K:
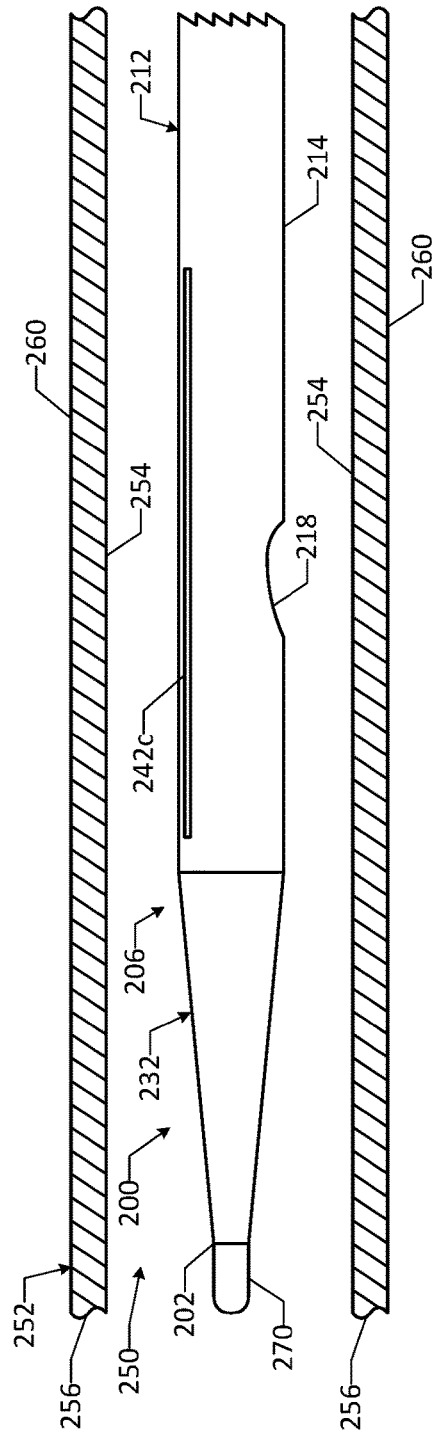
FIG. 2K is a side view of a portion of the vascular access device of FIG. 2A positioned within a natural lumen of a vessel, showing the deployable wires of the vascular access device in a delivery configuration.

FIGS. 2K-2N illustrate an example method of using the vascular access device 200 to provide access for performing a cardiac interventional procedure on a patient. Initially, the vascular access device 200 may be percutaneously inserted into the patient through a vascular access site formed in an artery, such as a femoral artery. With the proximal end portion 208 of the device 200 outside of the patient, the physician may manipulate the proximal end portion 208 in order to advance the distal end portion 206 of the device 200 through the vasculature and position the distal end portion 206 at a desired location within a natural lumen 250 of a desired vessel 252, as shown in FIG. 2K. In some embodiments, as shown, the vascular access device 200 is advanced over a guidewire 270 to facilitate guiding the distal end portion 206 of the device 200 through the vasculature and positioning the distal end portion 206 at the desired location within vessel 252.

Figure 2L:
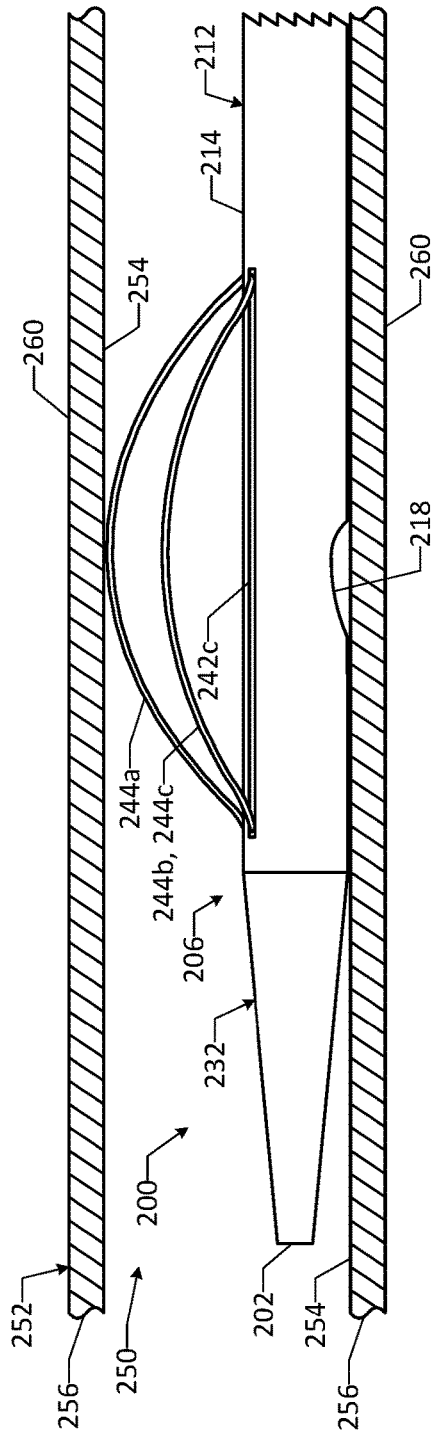
FIG. 2L is a side view of a portion of the vascular access device of FIG. 2A positioned within the natural lumen of the vessel, showing the deployable wires in the deployed configuration.

After the distal end portion 206 of the device 200 is positioned at the desired location within the natural lumen 250 of the vessel 252, the wires 244 may be deployed from the catheter 212, as shown in FIG. 2L. In other words, the wires 244 may be moved or allowed to move from their straight first configuration to their curved second configuration, as shown. In some embodiments, the wires 244 are moved from their straight first configuration to their curved second configuration by manipulating respective proximal ends of the wires 244 or intermediate components attached to the wires 244, positioned about the proximal end 204 of the vascular access device 200. In other embodiments, the wires 244 are allowed to move from their straight first configuration to their curved second configuration by removing or retracting a sheath positioned over the deployment openings 242 of the catheter 212. Still other components or mechanisms may be used to move the wires 244 or allow the wires 244 to move from their straight first configuration to their curved second configuration in other embodiments. When the wires 244 are in their curved second configuration, the wires 244 may at least partially engage a first part of an inner surface 254 of a wall 256 of the vessel 252 and may bias the catheter 212 toward a circumferentially opposite second part of the inner surface 254 of the vessel wall 256. As shown in FIG. 2L, the biasing force provided by the wires 244 may cause the external surface of the shaft 214 to engage the second part of the inner surface 254 of the vessel wall 256, such that a hemostatic connection is formed between a portion of the external surface of the shaft 214 which surrounds the access opening 218 and the inner surface 254 of the vessel wall 256. Furthermore, the biasing force provided by the wires 244 and the resulting engagement between the wires 244 and the first part of the inner surface 254 of the vessel wall 256 and between the external surface of the shaft 214 and the second part of the inner surface 254 of the vessel wall 256 may secure the position of the distal end portion 206 of the device 200 within the vessel lumen 250. After the hemostatic connection is formed between the external surface of the shaft 214 and the second part of the inner surface 254 of the vessel wall 256, the guidewire 270 may be retracted and removed from the guidewire lumen 220 and the primary lumen 216 of the catheter 212, as shown in FIG. 2L.

Figure 2M:
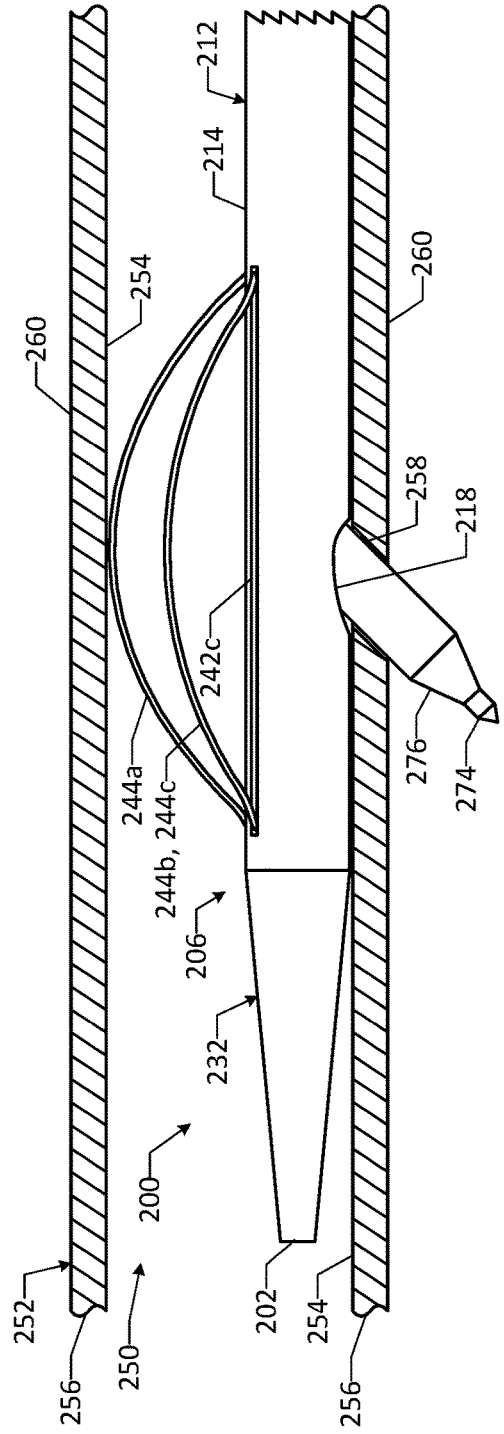
FIG. 2M is a side view of a portion of the vascular access device of FIG. 2A positioned within the natural lumen of the vessel, showing a guidewire and a dilator passed through the vascular access device and a wall of the vessel to form an aperture in the vessel wall.
Figure 2N:
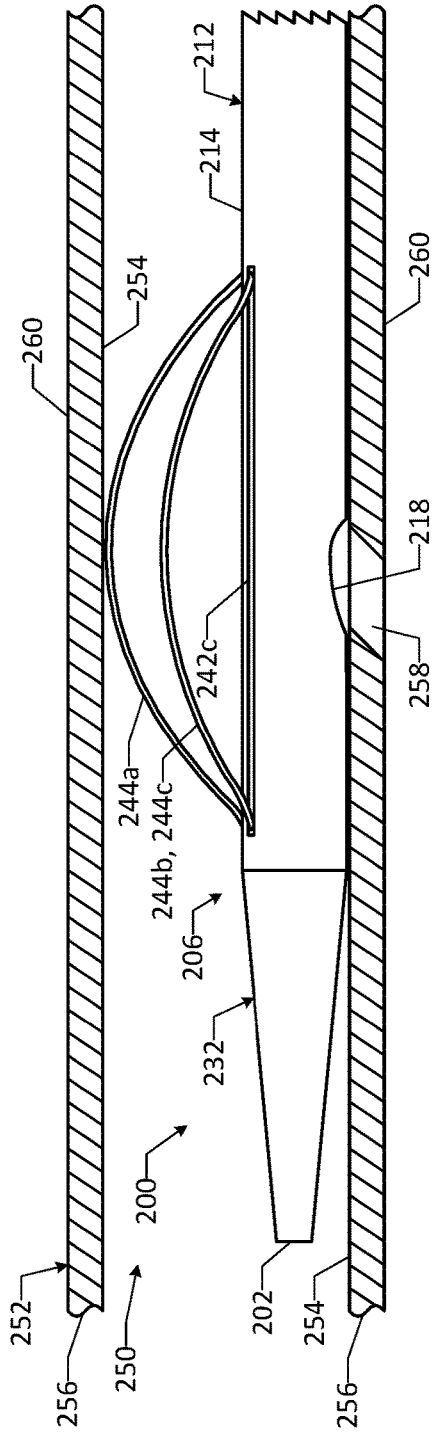
FIG. 2N is a side view of a portion of the vascular access device of FIG. 2A positioned within the natural lumen of the vessel, showing the aperture in the vessel wall and a hemostatic connection formed between the distal end portion and the vessel wall.

After the guidewire 270 is retracted and removed from the guidewire lumen 220 and the primary lumen 216 of the catheter 212, a guidewire 274 and/or a dilator 276 may be advanced through the primary lumen 216 and the access opening 218 of the catheter 112 and through the vessel wall 256, as shown in FIG. 2M. The guidewire 274 and/or the dilator 276 may form an aperture 258 in the vessel wall 256 extending from the inner surface 254 to an outer surface 260 of the vessel wall 256, while the hemostatic connection is maintained between the external surface of the shaft 214 and the second part of the inner surface 254 of the vessel wall 256. In this manner, the hemostatic connection may surround the aperture 258, thereby preventing or at least inhibiting blood from flowing out of the vessel lumen 250 through the aperture 258 and preventing or at least inhibiting body fluids or other materials from entering the vessel lumen 250 through the aperture 258. In some embodiments, the guidewire 274 is different than the guidewire 270. For example, the guidewire 274 may have a sharp distal tip, and the guidewire 270 may have a blunt or rounded distal tip. In other embodiments, the guidewire 274 may be the same as the guidewire 270 (i.e., the guidewire 270 may be used to guide the distal end portion 206 of the device 200 to the desired location in the vessel lumen 250 and to puncture the vessel wall 256 to form the aperture 258).

After the aperture 258 is formed in the vessel wall 256, the guidewire 274 and/or the dilator 276 may be retracted and removed from the primary lumen 216 of the catheter 212, while the hemostatic connection is maintained between the external surface of the shaft 214 and the second part of the inner surface 254 of the vessel wall 256, as shown in FIG. 1N. After removal of the guidewire 274 and/or the dilator 276 from the primary lumen 216, a cardiac interventional procedure may be performed through the vascular access device 200 and through the aperture 258, while the hemostatic connection is maintained between the external surface of the shaft 214 and the second part of the inner surface 254 of the vessel wall 256. In particular, one or more operative instruments or devices may be passed through the primary lumen 216 and the access opening 218 of the catheter 212 and the aperture 258 in the vessel wall 256 and into the thoracic cavity of the patient to perform a desired cardiac procedure on the desired vasculature. Upon completion of the cardiac procedure, the aperture 258 in the vessel wall 256 may be closed, and the vascular access device 200 may be removed from the patient.

In some embodiments, the vascular access device 200 may be used in combination with other devices to perform a desired cardiac procedure. For example, the vascular access device 200 may be used in combination with one of the puncturable balloon catheter devices described in U.S. Provisional Patent Application Ser. No. 62/331,229 to Crisco to perform a desired cardiac procedure, such as a coronary bypass procedure, as described therein. In such uses, the vascular access device 200 may be used inside of the vessel 252 in the manner described above, and the puncturable balloon catheter device may be used outside of the vessel 252 in the extravascular space, in the soft tissue of a limb of other anatomical locations including the chest and the pericardium, for the purpose of creating space for delivery of catheters, wires, delivery systems, and bypass conduits for the purposes of revascularization. Moreover, the vascular access device 200 may be used instead of the vascular access devices described in U.S. Provisional Patent Application Ser. No. 62/331,229 to Crisco to perform any of the cardiac procedures described therein.

FIGS. 2O-2R illustrate the vascular access device 200 and a sheath 246 that may be used with the device 200 or as a part of the device 200. The sheath 246 may have an elongated tubular shape and a circular axial cross-sectional shape, as shown, although other shapes of the sheath 246 may be used. As shown, the sheath 246 may be movably positioned over the catheter 212. In particular, the sheath 246 may be configured to translate axially relative to the catheter 212 between a first position (which also may be referred to as an "advanced position"), as shown in FIG. 2O, and a second position (which also may be referred to as a "retracted position"), as shown in FIG. 2P. When the sheath 246 is in the first position, the sheath 246 may be positioned over and cover the deployment openings 242 and the access opening 218 of the catheter 212. In this manner, the sheath 246 may prevent the wires 244 from assuming their curved second configuration and extending outward beyond the external surface of the shaft 214 when the sheath 246 is in the first position. When the sheath 246 is in the second position, the sheath 246 may be spaced apart from and not cover the deployment openings 242 and the access opening 218 of the catheter 212. In this manner, the wires 244 may be allowed to assume their curved second configuration and extend outward beyond the external surface of the shaft 214 when the sheath 246 is in the second position.

FIGS. 2S-2V illustrate the vascular access device 200 having a different configuration of the access opening 218, the guidewire lumen 220, and the lumen transition portion 222 as compared to the embodiment illustrated in FIGS. 2A-2J. In particular, as shown in FIGS. 2U and 2V, the acute angle between the longitudinal axis of the second portion 220b of the guidewire lumen 220 and the longitudinal axis $A_L$ of the device 200 may be greater such that the second portion 220b extends proximally to an opening 248 (which also may be referred to as a "guidewire opening" or a "guidewire entry opening"). As shown, the opening 248 may be defined at least partially in the side wall of the shaft 214 and at least partially in the lumen transition portion 222, and the opening 248 may partially overlap the access opening 218 of the catheter 212. As shown in FIGS. 2U and 2V, the access opening 218 may include a first portion 218a and a second portion 218b positioned proximally relative to the first portion 218a. The opening 248 and the first portion 218a of the access opening 218 may partially overlap one another, as shown. The second portion 218b of the access opening 218 may be shaped as a contoured notch or cutout that is in communication with the first portion 218a of the access opening 218, as shown. During use of the illustrated embodiment of the vascular access device 200, the guidewire 270 may pass through the opening 248, through the guidewire lumen 220, and out of the distal end 202 of the device 200, and the second portion 218b of the access opening 218 may accommodate the portion of the guidewire 270 that extends proximally out of and alongside the catheter 212. In this manner, according to the illustrated embodiment, the guidewire 270 is not passed through the primary lumen 216 of the catheter 212.

FIGS. 3A-3F illustrate a vascular access device 300 (which also may be referred to as an "endovascular access device") configured to provide access for performing cardiac interventional procedures on patients in need thereof, in accordance with one or more embodiments of the disclosure. As described in detail below, the vascular access device 300 is configured to be percutaneously inserted through the natural lumen of a vessel of a patient, to form a hemostatic connection between the device 300 and a surface of a wall of the vessel, and to facilitate formation of an aperture through the vessel wall to provide access to desired vasculature in a thoracic region of the patient. The vascular access device 300 also may be configured to allow operative instruments or other devices to be passed through the device 300 to perform a desired cardiac procedure on the patient, to allow a physician to assess the integrity of the hemostatic connection and the aperture formed through the vessel wall before, during, or after performing the desired cardiac procedure, and to allow sufficient blood flow to pass through the natural lumen of the vessel while the device 300 is positioned therein.

As shown in FIGS. 3A and 3B, the vascular access device 300 has an elongated shape including a distal end 302 (which also may be referred to as a "leading end") and a proximal end 304 (which also may be referred to as a "trailing end") positioned along a longitudinal axis $A_L$ of the device 300. The vascular access device 300 includes a distal end portion 306 extending from the distal end 302 toward the proximal end 304 along the longitudinal axis $A_L$, a proximal end portion 308 extending from the proximal end 304 toward the distal end 302 along the longitudinal axis $A_L$, and an intermediate portion 310 extending axially from the distal end portion 306 to the proximal end portion 308. It will be appreciated that part of the intermediate portion 310 of the vascular access device 300 is removed from view in FIGS. 3A and 3B for purposes of illustrating the device 300. When the vascular access device 300 is used to provide access for performing a cardiac procedure on a patient, the distal end portion 306 and at least part of the intermediate portion 310 may be percutaneously inserted through the natural lumen of a vessel, while the proximal end portion 308 remains at least partially outside of the patient's body. In this manner, the proximal end portion 308 may be manipulated by a physician outside of the patient's body in order to position the distal end portion 306 at a desired location within the vessel lumen and form a hemostatic connection between the distal end portion 306 and the vessel wall, as described below.

The vascular access device 300 includes a catheter 312, which may extend axially along the longitudinal axis $A_L$ of the device 300. The catheter 312 may include a flexible shaft 314 (which also may be referred to as a "tube") configured to traverse the vessel lumen in which the vascular access device 300 is inserted. As shown, the shaft 314 may have an elongated tubular shape and a circular axial cross-sectional shape, although other shapes of the shaft 314 may be used. In some embodiments, as shown, a longitudinal axis of the catheter 312 is coaxial with the longitudinal axis $A_L$ of the device 300. The catheter 312 may include a primary lumen 316 (which also may be referred to as a "working lumen" or an "access lumen") extending therethrough from the proximal end to the distal end of the catheter 312, as shown. As described below, the primary lumen 316 may be used to facilitate insertion and positioning of the vascular access device 300 within the vessel lumen via a guidewire, to facilitate formation of an aperture through the vessel wall, and to pass operative instruments or other devices through the device 300 and the aperture to perform a desired cardiac procedure on the patient. As shown, the primary lumen 316 may have a cylindrical shape and a circular axial cross-sectional shape, although other shapes of the primary lumen 316 may be used. In some embodiments, as shown, the longitudinal axis of the primary lumen 316 is coaxial with the longitudinal axis of the catheter 312 and the longitudinal axis $A_L$ of the device 300. In this manner, a wall thickness of the catheter 312 may be constant along the circumference of the catheter 312, as shown. In some embodiments, the catheter 312 is formed of a biocompatible polymer, although other suitable materials may be used in other embodiments. For example, the catheter 312 may be formed of a polyether block amide (PEBA), such as PEBAX®, a thermoplastic urethane (TPU), such as PELLETHANE®, or a nylon. In some embodiments, the catheter 312 includes a liner and/or a reinforcement structure arranged in a manner similar to the corresponding features of the catheters described above.

The shaft 314 of the catheter 312 may include a distal tip portion 322 (which also may be referred to as a "dilator tip portion") positioned about the distal end of the catheter 312. As shown, the external surface of the distal tip portion 322 may be curved or tapered such that the external surface curves or tapers radially inward in a direction from the proximal end to the distal end of the distal tip portion 322. In this manner, the distal tip portion 322 may facilitate guiding of the distal end portion 306 of the vascular access device 300 through the natural lumen of a vessel in which the device 300 is inserted. As shown in FIG. 3B, the catheter 312 may include one or more marker bands 324 positioned within the side wall of the shaft 314 and radially spaced apart from the primary lumen 316 and the external surface of the shaft 314. The marker bands 324 may have a ring shape and a circular axial cross-sectional shape, although other shapes of the marker bands 324 may be used. The marker bands 324 may be positioned near but axially spaced apart from the distal end of the catheter 312. In some embodiments, as shown, one marker band 324 is positioned at or near the proximal end of the distal tip portion 322. According to the illustrated embodiment, the catheter 312 includes only one marker band 324. However, it will be appreciated that the catheter 312 may include any number of marker bands 324 in other embodiments. The marker bands 324 may be formed of a radiopaque material that is visible under medical imaging. In this manner, a physician may observe the marker bands 324 via medical imaging as the catheter 312 is advanced through the vasculature and positioned within the vessel lumen. In some embodiments, the marker bands 324 are formed of platinum, tungsten, gold, or tantalum, although other suitable radiopaque materials may be used in other embodiments. In some embodiments, as an alternative to marker bands, one or more radiopaque additives may be compounded with a polymer to form the catheter 312, such that one or more portions of the catheter 312 is visible under medical imaging.

As shown, the vascular access device 300 also includes a dilator 332 (which also may be referred to as a "steerable dilator"), which may extend axially along the longitudinal axis $A_L$ of the device 300. The dilator 332 may include a flexible shaft 334 (which also may be referred to as a "tube") configured to traverse the vessel lumen in which the vascular access device 300 is inserted. As shown, the shaft 334 may have an elongated tubular shape and a circular axial cross-sectional shape, although other shapes of the shaft 334 may be used. In some embodiments, as shown, a longitudinal axis of the dilator 332 is coaxial with the longitudinal axis of the catheter 312 and the longitudinal axis $A_L$ of the device 300. The dilator 332 may include a primary lumen 336 (which also may be referred to as a "guidewire lumen" or a "guiding lumen") extending therethrough from the proximal end to the distal end of the dilator 332, as shown. As described below, the primary lumen 336 may be used to facilitate insertion and positioning of the vascular access device 300 within the vessel lumen via a guidewire, and to facilitate formation of an aperture through the vessel wall. As shown, the primary lumen 336 may have a cylindrical shape and a circular axial cross-sectional shape, although other shapes of the primary lumen 336 may be used. In some embodiments, as shown, the longitudinal axis of the primary lumen 336 is coaxial with the longitudinal axis of the dilator 332, the longitudinal axis of the catheter 312, and the longitudinal axis $A_L$ of the device 300. In this manner, a wall thickness of the dilator 332 may be constant along the circumference of the dilator 332, as shown. In some embodiments, the dilator 332 is formed of a biocompatible polymer, although other suitable materials may be used in other embodiments. For example, the dilator 332 may be formed of a polyimide (PI), a polytetrafluoroethylene (PTFE), a perfluoroalkoxy alkane (PFA), a fluorinated ethylene propylene (FEP), another fluoropolymer, or a polyethylene (PE), such as a high-density polyethylene (HDPE), a low-density polyethylene (LDPE), or a medium-density polyethylene (MIDPE). In some embodiments, the dilator 332 includes a liner and/or a reinforcement structure arranged in a manner similar to the corresponding features of the catheters described above.

The shaft 334 of the dilator 332 may include a distal tip portion 342 (which also may be referred to as a "dilator tip portion") positioned about the distal end of the dilator 332. As shown, the external surface of the distal tip portion 342 may be curved or tapered such that the external surface curves or tapers radially inward in a direction from the proximal end to the distal end of the distal tip portion 342. In this manner, the distal tip portion 342 may facilitate guiding of the distal end portion 306 of the vascular access device 300 through the natural lumen of a vessel in which the device 300 is inserted. As shown in FIG. 3B, the dilator 332 may include one or more marker bands 344 positioned within the side wall of the shaft 334 and radially spaced apart from the primary lumen 336 and the external surface of the shaft 334. The marker bands 344 may have a ring shape and a circular axial cross-sectional shape, although other shapes of the marker bands 344 may be used. The marker bands 344 may be positioned near but axially spaced apart from the distal end of the dilator 332. In some embodiments, as shown, one marker band 344 is positioned within the distal tip portion 342 and spaced apart from the proximal end and the distal end of the distal tip portion 342. According to the illustrated embodiment, the dilator 332 includes only one marker band 344. However, it will be appreciated that the dilator 332 may include any number of marker bands 344 in other embodiments. The marker bands 344 may be formed of a radiopaque material that is visible under medical imaging. In this manner, a physician may observe the marker bands 344 via medical imaging as the dilator 332 is advanced through the vasculature and positioned within the vessel lumen. In some embodiments, the marker bands 344 are formed of platinum, tungsten, gold, or tantalum, although other suitable radiopaque materials may be used in other embodiments. In some embodiments, as an alternative to marker bands, one or more radiopaque additives may be compounded with a polymer to form the dilator 332, such that one or more portions of the dilator 332 is visible under medical imaging.

As shown, the dilator 332 may include a wire 346 (which also may be referred to as a "pull wire" or a "steering wire") positioned at least partially within the side wall of the shaft 334. In particular, the wire 346 may be fixedly secured within a wire lumen 348 defined in the side wall of the shaft 334. As shown, the wire lumen 348 may be radially spaced apart from the primary lumen 336 and the external surface of the shaft 334. The wire lumen 348 may extend axially along the shaft 334 and parallel to the longitudinal axis of the dilator 332, and may have an open proximal end and a closed distal end. As shown in FIG. 3B, the open proximal end of the wire lumen 348 may be positioned at the proximal end of the dilator 332, and the closed distal end of the wire lumen 348 may be axially spaced apart from the distal end of the dilator 332. In some embodiments, as shown, the closed distal end of the wire lumen 348 is positioned at or near the proximal end of the distal tip portion 342, although other positions, such as within the distal tip portion 342 may be used in other embodiments. The wire 346 may have an elongated shape, with the distal end of the wire 346 positioned at the closed distal end of the wire lumen 348 and the proximal end of the wire 346 positioned proximally from the open proximal end of the wire lumen 348. In this manner, a proximal end portion of the wire 346 may extend proximally away from the proximal end of the dilator 332, such that the physician may grasp and manipulate the wire 346, for example by pulling the wire 346, in order to steer the dilator 332 and the overall vascular access device 300 from outside of the patient.

Figure 3C:
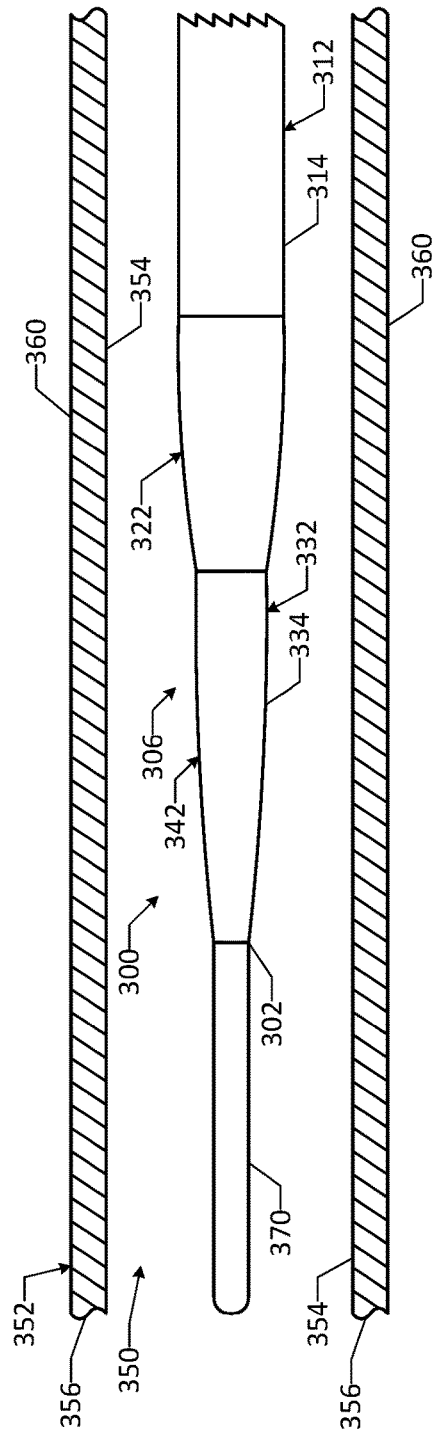
FIG. 3C is a side view of a portion of the vascular access device of FIG. 3A positioned within a natural lumen of a vessel, showing a distal end portion of the vascular access device in a straight configuration.

FIGS. 3C-3F illustrate an example method of using the vascular access device 300 to provide access for performing a cardiac interventional procedure on a patient. Initially, the vascular access device 300 may be percutaneously inserted into the patient through a vascular access site formed in an artery, such as a femoral artery. With the proximal end portion 308 of the device 300 outside of the patient, the physician may manipulate the proximal end portion 308 in order to advance the distal end portion 306 of the device 300 through the vasculature and position the distal end portion 306 at a desired location within a natural lumen 350 of a desired vessel 352, as shown in FIG. 3C. In some embodiments, as shown, the vascular access device 300 is advanced over a guidewire 370 to facilitate guiding the distal end portion 306 of the device 300 through the vasculature and positioning the distal end portion 306 at the desired location within vessel 352.

Figure 3D:
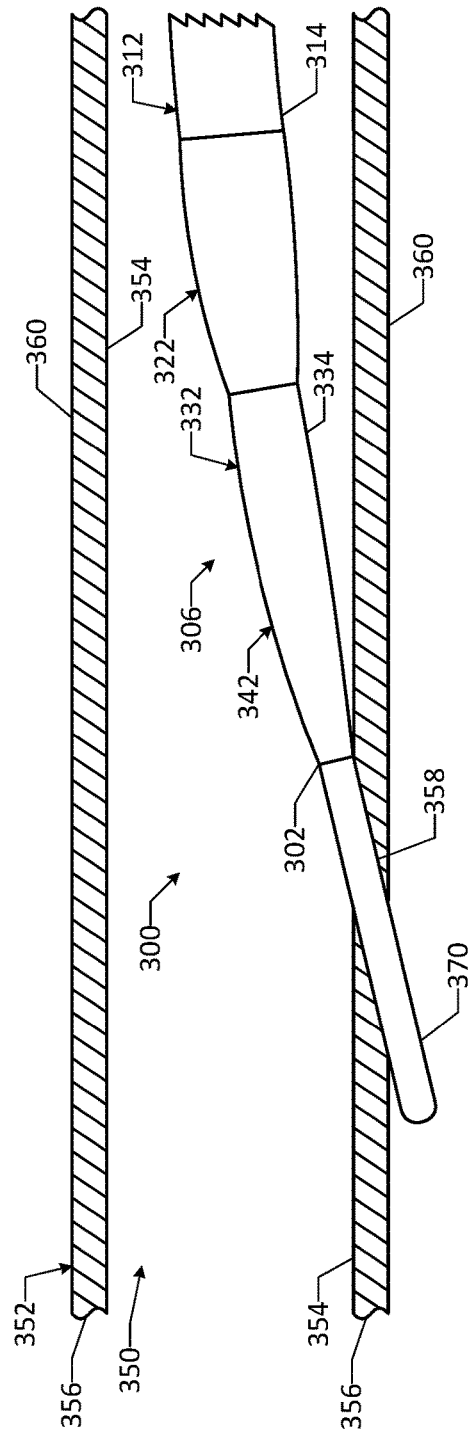
FIG. 3D is a side view of a portion of the vascular access device of FIG. 3A positioned within the natural lumen of the vessel, showing the distal end portion in a curved configuration and a guidewire of the vascular access device passed through a wall of the vessel to form an aperture in the vessel wall.

After the distal end portion 306 of the device 300 is positioned at the desired location within the natural lumen 350 of the vessel 352, the wire 346 may be manipulated by the physician, such as by pulling the wire 346 proximally relative to the proximal end portion 308 of the device 300 in order to steer the distal end portion 306. Such pulling of the wire 346 may cause the distal end portion 306 of the device 300 and a distal end portion of the guidewire 370 to curve or bend, as shown in FIG. 3D. With the guidewire 370 and the distal end portion 306 of the device 300 in the curved or bent configuration and in a desired orientation, the guidewire 370 may be advanced through a wall 356 of the vessel 352. In this manner, the guidewire 370 may form an aperture 358 in the vessel wall 356 extending from an inner surface 354 to an outer surface 360 of the vessel wall 356, as shown in FIG. 3D. The distal tip portion 342 of the dilator 332 and the distal tip portion 322 of the catheter 312 then may be advanced through the aperture 358 in the vessel wall 356, as shown in FIG. 3E. In this manner, the dilator 332 and the catheter 312 may dilate the aperture 358, and a hemostatic connection may be formed between the external surface of the catheter 312 and the circumferential inner surface of the aperture 358.

After the hemostatic connection is formed between the catheter 312 and the vessel wall 356, the guidewire 370 may be retracted and removed from the device 300, as shown in FIG. 3F. The dilator 332 also may be retracted and removed from the catheter 312 or may be left in place. After removal of the guidewire 373, a cardiac interventional procedure may be performed through the vascular access device 300 and through the aperture 358, while the hemostatic connection is maintained between the external surface of the catheter 312 and the inner surface of the aperture 358 in the vessel wall 356. In particular, one or more operative instruments or devices may be passed through the primary lumen 316 of the catheter 312 and/or the primary lumen 336 of the dilator 332, through the aperture 358 in the vessel wall 356, and into the thoracic cavity of the patient to perform a desired cardiac procedure on the desired vasculature. Upon completion of the cardiac procedure, the aperture 358 in the vessel wall 356 may be closed, and the vascular access device 300 may be removed from the patient.

In some embodiments, the vascular access device 300 may be used in combination with other devices to perform a desired cardiac procedure. For example, the vascular access device 300 may be used in combination with one of the puncturable balloon catheter devices described in U.S. Provisional Patent Application Ser. No. 62/331,229 to Crisco to perform a desired cardiac procedure, such as a coronary bypass procedure, as described therein. In such uses, the vascular access device 300 may be used inside of the vessel 352 in the manner described above, and the puncturable balloon catheter device may be used outside of the vessel 352 in the extravascular space, in the soft tissue of a limb of other anatomical locations including the chest and the pericardium, for the purpose of creating space for delivery of catheters, wires, delivery systems, and bypass conduits for the purposes of revascularization. Moreover, the vascular access device 300 may be used instead of the vascular access devices described in U.S. Provisional Patent Application Ser. No. 62/331,229 to Crisco to perform any of the cardiac procedures described therein.

FIGS. 4A-4G illustrate a vascular access device 400 (which also may be referred to as an "endovascular access device") configured to provide access for performing cardiac interventional procedures on patients in need thereof, in accordance with one or more embodiments of the disclosure. As described in detail below, the vascular access device 400 is configured to be percutaneously inserted through the natural lumen of a vessel of a patient, to form a hemostatic connection between the device 400 and a surface of a wall of the vessel, and to facilitate formation of an aperture through the vessel wall to provide access to desired vasculature in a thoracic region of the patient. The vascular access device 400 also may be configured to allow operative instruments or other devices to be passed through the device 400 to perform a desired cardiac procedure on the patient, to allow a physician to assess the integrity of the hemostatic connection and the aperture formed through the vessel wall before, during, or after performing the desired cardiac procedure, and to allow sufficient blood flow to pass through the natural lumen of the vessel while the device 400 is positioned therein.

As shown in FIGS. 4A and 4B, the vascular access device 400 has an elongated shape including a distal end 402 (which also may be referred to as a "leading end") and a proximal end 404 (which also may be referred to as a "trailing end") positioned along a longitudinal axis $A_L$ of the device 400. The vascular access device 400 includes a distal end portion 406 extending from the distal end 402 toward the proximal end 404 along the longitudinal axis $A_L$, a proximal end portion 408 extending from the proximal end 404 toward the distal end 402 along the longitudinal axis $A_L$, and an intermediate portion 410 extending axially from the distal end portion 406 to the proximal end portion 408. It will be appreciated that part of the intermediate portion 410 of the vascular access device 400 is removed from view in FIGS. 4A and 4B for purposes of illustrating the device 400. When the vascular access device 400 is used to provide access for performing a cardiac procedure on a patient, the distal end portion 406 and at least part of the intermediate portion 410 may be percutaneously inserted through the natural lumen of a vessel, while the proximal end portion 408 remains at least partially outside of the patient's body. In this manner, the proximal end portion 408 may be manipulated by a physician outside of the patient's body in order to position the distal end portion 406 at a desired location within the vessel lumen and form a hemostatic connection between the distal end portion 406 and the vessel wall, as described below.

The vascular access device 400 includes a catheter 412 (which also may be referred to as a "steerable catheter"), which may extend axially along the longitudinal axis $A_L$ of the device 400. The catheter 412 may include a flexible shaft 414 (which also may be referred to as a "tube") configured to traverse the vessel lumen in which the vascular access device 400 is inserted. As shown, the shaft 414 may have an elongated tubular shape and a circular axial cross-sectional shape, although other shapes of the shaft 414 may be used. In some embodiments, as shown, a longitudinal axis of the catheter 412 is coaxial with the longitudinal axis $A_L$ of the device 400. The catheter 412 may include a primary lumen 416 (which also may be referred to as a "working lumen" or an "access lumen") extending therethrough from the proximal end to the distal end of the catheter 412, as shown. As described below, the primary lumen 416 may be used to facilitate insertion and positioning of the vascular access device 400 within the vessel lumen via a guidewire, to facilitate formation of an aperture through the vessel wall, and to pass operative instruments or other devices through the device 400 and the aperture to perform a desired cardiac procedure on the patient. As shown, the primary lumen 416 may have a cylindrical shape and a circular axial cross-sectional shape, although other shapes of the primary lumen 416 may be used. In some embodiments, as shown, the longitudinal axis of the primary lumen 416 is coaxial with the longitudinal axis of the catheter 412 and the longitudinal axis $A_L$ of the device 400. In this manner, a wall thickness of the catheter 412 may be constant along the circumference of the catheter 412, as shown. In some embodiments, the catheter 412 is formed of a biocompatible polymer, although other suitable materials may be used in other embodiments. For example, the catheter 412 may be formed of a polyether block amide (PEBA), such as PEBAX®, a thermoplastic urethane (TPU), such as PELLETHANE®, or a nylon. In some embodiments, the catheter 412 includes a liner and/or a reinforcement structure arranged in a manner similar to the corresponding features of the catheters described above.

The shaft 414 of the catheter 412 may include a distal tip portion 422 (which also may be referred to as a "dilator tip portion") positioned about the distal end of the catheter 412. As shown, the external surface of the distal tip portion 422 may be curved or tapered such that the external surface curves or tapers radially inward in a direction from the proximal end to the distal end of the distal tip portion 422. In this manner, the distal tip portion 422 may facilitate guiding of the distal end portion 406 of the vascular access device 400 through the natural lumen of a vessel in which the device 400 is inserted. As shown in FIGS. 4B and 4C, the catheter 412 may include one or more marker bands 424 positioned within the side wall of the shaft 414 and radially spaced apart from the primary lumen 416 and the external surface of the shaft 414. The marker bands 424 may have a ring shape and a circular axial cross-sectional shape, although other shapes of the marker bands 424 may be used. The marker bands 424 may be positioned near but axially spaced apart from the distal end of the catheter 412. In some embodiments, as shown, one marker band 424 is positioned at or near the proximal end of the distal tip portion 422. According to the illustrated embodiment, the catheter 412 includes only one marker band 424. However, it will be appreciated that the catheter 412 may include any number of marker bands 424 in other embodiments. The marker bands 424 may be formed of a radiopaque material that is visible under medical imaging. In this manner, a physician may observe the marker bands 424 via medical imaging as the catheter 412 is advanced through the vasculature and positioned within the vessel lumen. In some embodiments, the marker bands 424 are formed of platinum, tungsten, gold, or tantalum, although other suitable radiopaque materials may be used in other embodiments. In some embodiments, as an alternative to marker bands, one or more radiopaque additives may be compounded with a polymer to form the catheter 412, such that one or more portions of the catheter 412 is visible under medical imaging.

As shown, the catheter 412 may include a wire 426 (which also may be referred to as a "pull wire" or a "steering wire") positioned at least partially within the side wall of the shaft 414. In particular, the wire 426 may be fixedly secured within a wire lumen 428 defined in the side wall of the shaft 414. As shown, the wire lumen 428 may be radially spaced apart from the primary lumen 416 and the external surface of the shaft 414. The wire lumen 428 may extend axially along the shaft 414 and parallel to the longitudinal axis of the catheter 412, and may have an open proximal end and a closed distal end. As shown in FIG. 4B, the open proximal end of the wire lumen 428 may be positioned at the proximal end of the catheter 412, and the closed distal end of the wire lumen 428 may be axially spaced apart from the distal end of the catheter 412. In some embodiments, as shown, the closed distal end of the wire lumen 428 is positioned at or near the proximal end of the distal tip portion 422, although other positions, such as within the distal tip portion 422 may be used in other embodiments. The wire 426 may have an elongated shape, with the distal end of the wire 426 positioned at the closed distal end of the wire lumen 428 and the proximal end of the wire 426 positioned proximally from the open proximal end of the wire lumen 428. In this manner, a proximal end portion of the wire 426 may extend proximally away from the proximal end of the catheter 412, such that the physician may grasp and manipulate the wire 426, for example by pulling the wire 426, in order to steer the catheter 412 and the overall vascular access device 400 from outside of the patient.

As shown, the vascular access device 400 also includes a dilator 432, which may extend axially along the longitudinal axis $A_L$ of the device 400. The dilator 432 may include a flexible shaft 434 (which also may be referred to as a "tube") configured to traverse the vessel lumen in which the vascular access device 400 is inserted. As shown, the shaft 434 may have an elongated tubular shape and a circular axial cross-sectional shape, although other shapes of the shaft 434 may be used. In some embodiments, as shown, a longitudinal axis of the dilator 432 is coaxial with the longitudinal axis of the catheter 412 and the longitudinal axis $A_L$ of the device 400. The dilator 432 may include a primary lumen 436 (which also may be referred to as a "guidewire lumen" or a "guiding lumen") extending therethrough from the proximal end to the distal end of the dilator 432, as shown. As described below, the primary lumen 436 may be used to facilitate insertion and positioning of the vascular access device 400 within the vessel lumen via a guidewire, and to facilitate formation of an aperture through the vessel wall. As shown, the primary lumen 436 may have a cylindrical shape and a circular axial cross-sectional shape, although other shapes of the primary lumen 436 may be used. In some embodiments, as shown, the longitudinal axis of the primary lumen 436 is coaxial with the longitudinal axis of the dilator 432, the longitudinal axis of the catheter 412, and the longitudinal axis $A_L$ of the device 400. In this manner, a wall thickness of the dilator 432 may be constant along the circumference of the dilator 432, as shown. In some embodiments, the dilator 432 is formed of a biocompatible polymer, although other suitable materials may be used in other embodiments. For example, the dilator 432 may be formed of a polyimide (PI), a polytetrafluoroethylene (PTFE), a perfluoroalkoxy alkane (PFA), a fluorinated ethylene propylene (FEP), another fluoropolymer, or a polyethylene (PE), such as a high-density polyethylene (HDPE), a low-density polyethylene (LDPE), or a medium-density polyethylene (MDPE). In some embodiments, the dilator 432 includes a liner and/or a reinforcement structure arranged in a manner similar to the corresponding features of the catheters described above.

The shaft 434 of the dilator 432 may include a distal tip portion 442 (which also may be referred to as a "dilator tip portion") positioned about the distal end of the dilator 432. As shown, the external surface of the distal tip portion 442 may be curved or tapered such that the external surface curves or tapers radially inward in a direction from the proximal end to the distal end of the distal tip portion 442. In this manner, the distal tip portion 442 may facilitate guiding of the distal end portion 406 of the vascular access device 400 through the natural lumen of a vessel in which the device 400 is inserted. As shown in FIG. 4B, the dilator 432 may include one or more marker bands 444 positioned within the side wall of the shaft 434 and radially spaced apart from the primary lumen 436 and the external surface of the shaft 434. The marker bands 444 may have a ring shape and a circular axial cross-sectional shape, although other shapes of the marker bands 444 may be used. The marker bands 444 may be positioned near but axially spaced apart from the distal end of the dilator 432. In some embodiments, as shown, one marker band 444 is positioned within the distal tip portion 442 and spaced apart from the proximal end and the distal end of the distal tip portion 442. According to the illustrated embodiment, the dilator 432 includes only one marker band 444. However, it will be appreciated that the dilator 432 may include any number of marker bands 444 in other embodiments. The marker bands 444 may be formed of a radiopaque material that is visible under medical imaging. In this manner, a physician may observe the marker bands 444 via medical imaging as the dilator 432 is advanced through the vasculature and positioned within the vessel lumen. In some embodiments, the marker bands 444 are formed of platinum, tungsten, gold, or tantalum, although other suitable radiopaque materials may be used in other embodiments. In some embodiments, as an alternative to marker bands, one or more radiopaque additives may be compounded with a polymer to form the dilator 432, such that one or more portions of the dilator 432 is visible under medical imaging.

FIGS. 4D-4G illustrate an example method of using the vascular access device 400 to provide access for performing a cardiac interventional procedure on a patient. Initially, the vascular access device 400 may be percutaneously inserted into the patient through a vascular access site formed in an artery, such as a femoral artery. With the proximal end portion 408 of the device 400 outside of the patient, the physician may manipulate the proximal end portion 408 in order to advance the distal end portion 406 of the device 400 through the vasculature and position the distal end portion 406 at a desired location within a natural lumen 450 of a desired vessel 452, as shown in FIG. 4D. In some embodiments, as shown, the vascular access device 400 is advanced over a guidewire 470 to facilitate guiding the distal end portion 406 of the device 400 through the vasculature and positioning the distal end portion 406 at the desired location within vessel 452.

After the distal end portion 406 of the device 400 is positioned at the desired location within the natural lumen 450 of the vessel 452, the wire 426 may be manipulated by the physician, such as by pulling the wire 426 proximally relative to the proximal end portion 408 of the device 400 in order to steer the distal end portion 406. Such pulling of the wire 426 may cause the distal end portion 406 of the device 400 and a distal end portion of the guidewire 470 to curve or bend, as shown in FIG. 4E. With the guidewire 470 and the distal end portion 406 of the device 400 in the curved or bent configuration and in a desired orientation, the guidewire 470 may be advanced through a wall 456 of the vessel 452. In this manner, the guidewire 470 may form an aperture 458 in the vessel wall 456 extending from an inner surface 454 to an outer surface 460 of the vessel wall 456, as shown in FIG. 4E. The distal tip portion 442 of the dilator 432 and the distal tip portion 422 of the catheter 412 then may be advanced through the aperture 458 in the vessel wall 456, as shown in FIG. 4F. In this manner, the dilator 432 and the catheter 412 may dilate the aperture 458, and a hemostatic connection may be formed between the external surface of the catheter 412 and the circumferential inner surface of the aperture 458.

After the hemostatic connection is formed between the catheter 412 and the vessel wall 456, the guidewire 470 may be retracted and removed from the device 400, as shown in FIG. 4G. The dilator 432 also may be retracted and removed from the catheter 412 or may be left in place. After removal of the guidewire 470, a cardiac interventional procedure may be performed through the vascular access device 400 and through the aperture 458, while the hemostatic connection is maintained between the external surface of the catheter 412 and the inner surface of the aperture 458 in the vessel wall 456. In particular, one or more operative instruments or devices may be passed through the primary lumen 416 of the catheter 412 and/or the primary lumen 436 of the dilator 432, through the aperture 458 in the vessel wall 456, and into the thoracic cavity of the patient to perform a desired cardiac procedure on the desired vasculature. Upon completion of the cardiac procedure, the aperture 458 in the vessel wall 456 may be closed, and the vascular access device 400 may be removed from the patient.

In some embodiments, the vascular access device 400 may be used in combination with other devices to perform a desired cardiac procedure. For example, the vascular access device 400 may be used in combination with one of the puncturable balloon catheter devices described in U.S. Provisional Patent Application Ser. No. 62/331,229 to Crisco to perform a desired cardiac procedure, such as a coronary bypass procedure, as described therein. In such uses, the vascular access device 400 may be used inside of the vessel 452 in the manner described above, and the puncturable balloon catheter device may be used outside of the vessel 452 in the extravascular space, in the soft tissue of a limb of other anatomical locations including the chest and the pericardium, for the purpose of creating space for delivery of catheters, wires, delivery systems, and bypass conduits for the purposes of revascularization. Moreover, the vascular access device 400 may be used instead of the vascular access devices described in U.S. Provisional Patent Application Ser. No. 62/331,229 to Crisco to perform any of the cardiac procedures described therein.

FIGS. 5A-5D illustrate a vascular access device 500 (which also may be referred to as an "endovascular access device") configured to provide access for performing cardiac interventional procedures on patients in need thereof, in accordance with one or more embodiments of the disclosure. As described in detail below, the vascular access device 500 is configured to be percutaneously inserted through the natural lumen of a vessel of a patient, to form a hemostatic connection between the device 500 and a surface of a wall of the vessel, and to facilitate formation of an aperture through the vessel wall to provide access to desired vasculature in a thoracic region of the patient. The vascular access device 500 also may be configured to allow operative instruments or other devices to be passed through the device 500 to perform a desired cardiac procedure on the patient, to allow a physician to assess the integrity of the hemostatic connection and the aperture formed through the vessel wall before, during, or after performing the desired cardiac procedure, and to allow sufficient blood flow to pass through the natural lumen of the vessel while the device 500 is positioned therein.

As shown in FIG. 5A, the vascular access device 500 has an elongated shape including a distal end 502 (which also may be referred to as a "leading end") and a proximal end 504 (which also may be referred to as a "trailing end") positioned along a longitudinal axis $A_L$ of the device 500. The vascular access device 500 includes a distal end portion 506 extending from the distal end 502 toward the proximal end 504 along the longitudinal axis $A_L$, a proximal end portion 508 extending from the proximal end 504 toward the distal end 502 along the longitudinal axis $A_L$, and an intermediate portion 510 extending axially from the distal end portion 506 to the proximal end portion 508. It will be appreciated that part of the intermediate portion 510 of the vascular access device 500 is removed from view in FIG. 5A for purposes of illustrating the device 500. When the vascular access device 500 is used to provide access for performing a cardiac procedure on a patient, the distal end portion 506 and at least part of the intermediate portion 510 may be percutaneously inserted through the natural lumen of a vessel, while the proximal end portion 508 remains at least partially outside of the patient's body. In this manner, the proximal end portion 508 may be manipulated by a physician outside of the patient's body in order to position the distal end portion 506 at a desired location within the vessel lumen and form a hemostatic connection between the distal end portion 506 and the vessel wall, as described below.

The vascular access device 500 includes a catheter 512 (which also may be referred to as a "steerable catheter"), which may extend axially along the longitudinal axis $A_L$ of the device 500. The catheter 512 may include a flexible shaft 514 (which also may be referred to as a "tube") configured to traverse the vessel lumen in which the vascular access device 500 is inserted. As shown, the shaft 514 may have an elongated tubular shape and a circular axial cross-sectional shape, although other shapes of the shaft 514 may be used. In some embodiments, as shown, a longitudinal axis of the catheter 512 is coaxial with the longitudinal axis $A_L$ of the device 500. The catheter 512 may include a primary lumen (which also may be referred to as a "working lumen" or an "access lumen") extending therethrough from the proximal end to the distal end of the catheter 512. As described below, the primary lumen may be used to facilitate insertion and positioning of the vascular access device 500 within the vessel lumen via a guidewire, to facilitate formation of an aperture through the vessel wall, and to pass operative instruments or other devices through the device 500 and the aperture to perform a desired cardiac procedure on the patient. The primary lumen may have a cylindrical shape and a circular axial cross-sectional shape, although other shapes of the primary lumen may be used. In some embodiments, as shown, the longitudinal axis of the primary lumen is coaxial with the longitudinal axis of the catheter 512 and the longitudinal axis $A_L$ of the device 500. In this manner, a wall thickness of the catheter 512 may be constant along the circumference of the catheter 512, as shown. In some embodiments, the catheter 512 is formed of a biocompatible polymer, although other suitable materials may be used in other embodiments. For example, the catheter 512 may be formed of a polyether block amide (PEBA), such as PEBAX®, a thermoplastic urethane (TPU), such as PELLETHANE®, or a nylon. In some embodiments, the catheter 512 includes a liner and/or a reinforcement structure arranged in a manner similar to the corresponding features of the catheters described above.

The shaft 514 of the catheter 512 may include a distal tip portion 522 (which also may be referred to as a "dilator tip portion") positioned about the distal end of the catheter 512. As shown, the external surface of the distal tip portion 522 may be tapered such that the external surface tapers radially inward in a direction from the proximal end to the distal end of the distal tip portion 522. In this manner, the distal tip portion 522 may facilitate guiding of the distal end portion 506 of the vascular access device 500 through the natural lumen of a vessel in which the device 500 is inserted. As shown, the catheter 512 may include a number of coated regions 524 positioned on the external surface of the shaft 514. In particular, the catheter 512 may include a first coated region 524a positioned at or near the proximal end of the distal tip portion 522, and a second coated region 524b that is axially spaced apart from the first coated region 524a, as shown. The coated regions 524 may include a hydrophilic coating having absorption characteristics that allow the coating to expand beyond its original state. For example, the hydrophilic coating may be configured to expand up to 180% of its original state. As described below, the coated regions 524 may assist in securing the catheter 512 with respect to the vessel wall and forming a hemostatic connection between the catheter 512 and the vessel wall. When the coating is expanded, the coating may still be sufficiently compliant such that the catheter 512 may be removed from the vessel wall when desired. In some embodiments, the coating of the coated regions 524 is formed of one or more hydrophilic materials, although other suitable materials may be used in other embodiments.

As shown, the vascular access device 500 also includes a dilator 532, which may extend axially along the longitudinal axis $A_L$ of the device 500. The dilator 532 may include a flexible shaft 534 (which also may be referred to as a "tube") configured to traverse the vessel lumen in which the vascular access device 500 is inserted. As shown, the shaft 534 may have an elongated tubular shape and a circular axial cross-sectional shape, although other shapes of the shaft 534 may be used. In some embodiments, as shown, a longitudinal axis of the dilator 532 is coaxial with the longitudinal axis of the catheter 512 and the longitudinal axis $A_L$ of the device 500. The dilator 532 may include a primary lumen (which also may be referred to as a "guidewire lumen" or a "guiding lumen") extending therethrough from the proximal end to the distal end of the dilator 532. As described below, the primary lumen may be used to facilitate insertion and positioning of the vascular access device 500 within the vessel lumen via a guidewire, and to facilitate formation of an aperture through the vessel wall. The primary lumen may have a cylindrical shape and a circular axial cross-sectional shape, although other shapes of the primary lumen may be used. In some embodiments, the longitudinal axis of the primary lumen is coaxial with the longitudinal axis of the dilator 532, the longitudinal axis of the catheter 512, and the longitudinal axis $A_L$ of the device 500. In this manner, a wall thickness of the dilator 532 may be constant along the circumference of the dilator 532, as shown. In some embodiments, the dilator 532 is formed of a biocompatible polymer, although other suitable materials may be used in other embodiments. For example, the dilator 532 may be formed of a polyimide (PI), a polytetrafluoroethylene (PTFE), a perfluoroalkoxy alkane (PFA), a fluorinated ethylene propylene (FEP), another fluoropolymer, or a polyethylene (PE), such as a high-density polyethylene (HDPE), a low-density polyethylene (LDPE), or a medium-density polyethylene (MDPE). In some embodiments, the dilator 532 includes a liner and/or a reinforcement structure arranged in a manner similar to the corresponding features of the catheters described above.

The shaft 534 of the dilator 532 may include a distal tip portion 542 (which also may be referred to as a "dilator tip portion") positioned about the distal end of the dilator 532. As shown, the external surface of the distal tip portion 542 may be tapered such that the external surface tapers radially inward in a direction from the proximal end to the distal end of the distal tip portion 542. In this manner, the distal tip portion 542 may facilitate guiding of the distal end portion 506 of the vascular access device 500 through the natural lumen of a vessel in which the device 500 is inserted.

FIGS. 5B-5B illustrate an example method of using the vascular access device 500 to provide access for performing a cardiac interventional procedure on a patient. Initially, the vascular access device 500 may be percutaneously inserted into the patient through a vascular access site formed in an artery, such as a femoral artery. With the proximal end portion 508 of the device 500 outside of the patient, the physician may manipulate the proximal end portion 508 in order to advance the distal end portion 506 of the device 500 through the vasculature and position the distal end portion 506 at a desired location within a natural lumen of a desired vessel 552. In some embodiments, as shown, the vascular access device 500 is advanced over a guidewire 570 to facilitate guiding the distal end portion 506 of the device 500 through the vasculature and positioning the distal end portion 506 at the desired location within vessel 552.

After the distal end portion 506 of the device 500 is positioned at the desired location within the natural lumen of the vessel 552, the guidewire 570 may be advanced through a wall 556 of the vessel 552, as shown in FIG. 5B. In this manner, the guidewire 570 may form an aperture 558 in the vessel wall 556 extending from an inner surface 554 to an outer surface 560 of the vessel wall 556, as shown. The distal tip portion 542 of the dilator 532 and the distal tip portion 522 of the catheter 512 then may be advanced through the aperture 558 in the vessel wall 556, as shown in FIG. 5C. In this manner, the dilator 532 and the catheter 512 may dilate the aperture 558, and a hemostatic connection may be formed between the external surface of the catheter 512 and the circumferential inner surface of the aperture 558. The catheter 512 may be positioned with respect to the vessel wall 556 such that the vessel wall 556 is positioned between the first coated region 524a and the second coated region 524b, as shown in FIG. 5C. While the catheter 512 is maintained in this position relative to the vessel wall 556, the coating of the coated regions 524 may expand, as shown in FIG. 5D, such the coated regions 524 form a pair of rings that respectively engage the inner surface 554 and the outer surface 560 of the vessel wall 556. In this manner, the coated regions 524 may maintain the secure positioning of the catheter 512 relative to the vessel wall 556 and also may assist in forming and maintaining the hemostatic connection between the catheter 512 and the vessel wall 556.

After the hemostatic connection is formed between the catheter 512 and the vessel wall 556, the guidewire 570 may be retracted and removed from the device 500. The dilator 532 also may be retracted and removed from the catheter 512 or may be left in place. After removal of the guidewire 570, a cardiac interventional procedure may be performed through the vascular access device 500 and through the aperture 558, while the hemostatic connection is maintained between the external surface of the catheter 512 and the inner surface of the aperture 558 in the vessel wall 556. In particular, one or more operative instruments or devices may be passed through the primary lumen of the catheter 512 and/or the primary lumen of the dilator 532, through the aperture 558 in the vessel wall 556, and into the thoracic cavity of the patient to perform a desired cardiac procedure on the desired vasculature. Upon completion of the cardiac procedure, the aperture 558 in the vessel wall 556 may be closed, and the vascular access device 500 may be removed from the patient.

In some embodiments, the vascular access device 500 may be used in combination with other devices to perform a desired cardiac procedure. For example, the vascular access device 500 may be used in combination with one of the puncturable balloon catheter devices described in U.S. Provisional Patent Application Ser. No. 62/331,229 to Crisco to perform a desired cardiac procedure, such as a coronary bypass procedure, as described therein. In such uses, the vascular access device 500 may be used inside of the vessel 552 in the manner described above, and the puncturable balloon catheter device may be used outside of the vessel 552 in the extravascular space, in the soft tissue of a limb of other anatomical locations including the chest and the pericardium, for the purpose of creating space for delivery of catheters, wires, delivery systems, and bypass conduits for the purposes of revascularization. Moreover, the vascular access device 500 may be used instead of the vascular access devices described in U.S. Provisional Patent Application Ser. No. 62/331,229 to Crisco to perform any of the cardiac procedures described therein.

Figure 5E:
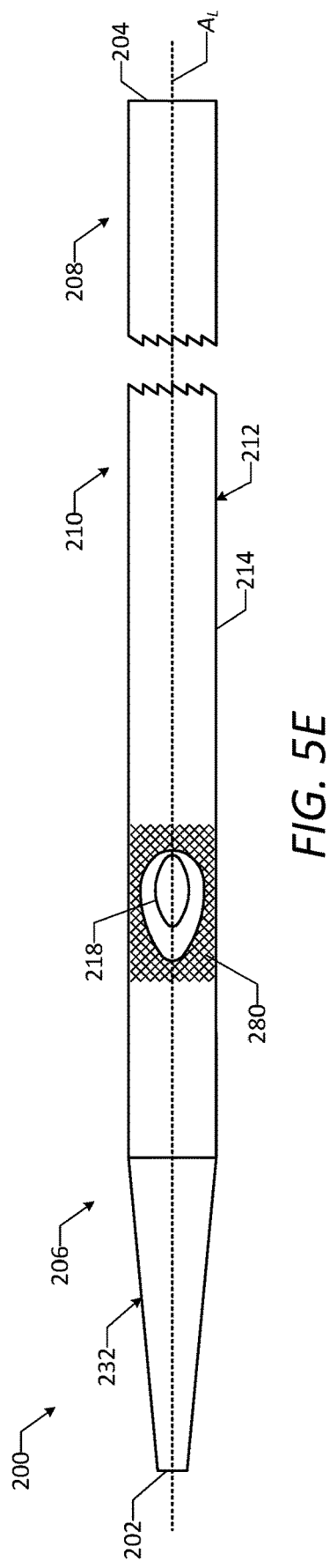
FIG. 5E is a bottom view of the vascular access device of FIG. 2A, showing a coated region of a catheter of the vascular access device.
Figure 5F:
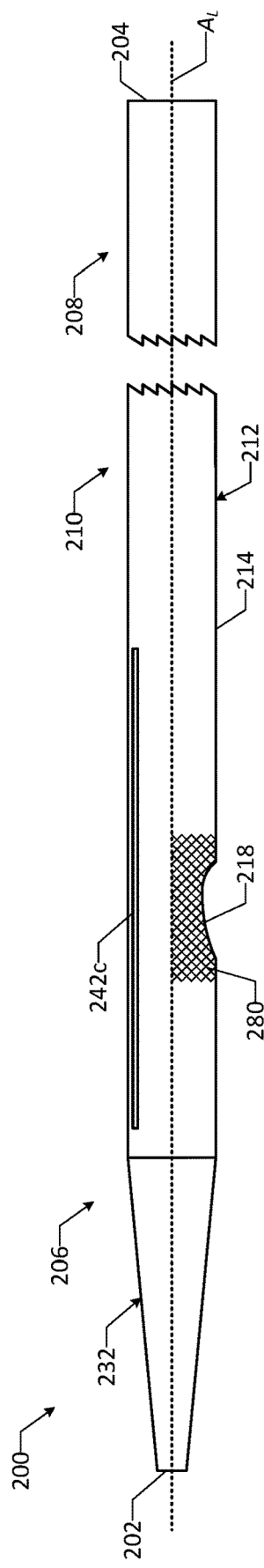
FIG. 5F is a side view of the vascular access device of FIG. 2A, showing the coated region of the catheter.

FIGS. 5E and 5F illustrate an embodiment of the vessel access device 200 described above with a coated region 280 positioned on the external surface of the shaft 214 of the catheter 212. In particular, the coated region 280 may be positioned about the access opening 218 of the catheter 212 along a bottom half of the external surface of the shaft 214 and may surround the access opening 218. FIGS. 5G and 511 illustrate another embodiment of the vessel access device 200 described above with a coated region 280 positioned on the external surface of the shaft 214 of the catheter 212. In particular, the coated region 280 may be positioned about the access opening 218 of the catheter 212 along a bottom half of the external surface of the shaft 214 and may surround the access opening 218. The coated region 280 may include a hydrophilic coating having absorption characteristics that allow the coating to expand beyond its original state. For example, the hydrophilic coating may be configured to expand up to 180% of its original state. In this manner, the coated region 280 may assist in securing the catheter 212 with respect to the vessel wall and forming a hemostatic connection between the catheter 212 and the vessel wall. In some embodiments, the coating of the coated region 280 is formed of one or more hydrophilic materials, although other suitable materials may be used in other embodiments.

FIGS. 6A-6H illustrate a vascular access device 600 (which also may be referred to as an "endovascular access device") configured to provide access for performing cardiac interventional procedures on patients in need thereof, in accordance with one or more embodiments of the disclosure. As described in detail below, the vascular access device 600 is configured to be percutaneously inserted through the natural lumen of a vessel of a patient, to form a hemostatic connection between the device 600 and an inner surface of a wall of the vessel, and to facilitate formation of an aperture through the vessel wall to provide access to desired vasculature in a thoracic region of the patient. The vascular access device 600 also may be configured to allow operative instruments or other devices to be passed through the device 600 to perform a desired cardiac procedure on the patient, to allow a physician to assess the integrity of the hemostatic connection and the aperture formed through the vessel wall before, during, or after performing the desired cardiac procedure, and to allow sufficient blood flow to pass through the natural lumen of the vessel while the device 600 is positioned therein.

As shown in FIGS. 6A-6E, the vascular access device 600 has an elongated shape including a distal end 602 (which also may be referred to as a "leading end") and a proximal end 604 (which also may be referred to as a "trailing end") positioned along a longitudinal axis $A_L$ of the device 600. The vascular access device 600 includes an outer tube 606 and an inner guide member 608, as shown. The outer tube 606 may extend axially along the longitudinal axis $A_L$ of the device 600 and may have an elongated tubular shape and a circular axial cross-sectional shape, although other shapes of the outer tube 606 may be used. The outer tube 606 may include a primary lumen 616 (which also may be referred to as a "blood flow lumen") extending therethrough from the proximal end to the distal end of the device 606. As described below, the primary lumen 616 may allow blood to flow therethrough when the vascular access device 600 is positioned within the natural lumen of a vessel. The outer tube 606 also may include an access opening 618 defined in the external surface of the outer tube 606, as shown. The outer tube 606 may be formed a resiliently flexible material, such that the outer tube 606 may conform to the shape of the vessel. In some embodiments, the outer tube 606 is formed of a biocompatible polymer, although other suitable materials may be used in other embodiments. For example, the outer tube 606 may be formed of a polyether block amide (PEBA), such as PEBAX®, a thermoplastic urethane (TPU), such as PELLETHANE®, or a nylon. In some embodiments, the outer tube 606 includes a liner and/or a reinforcement structure arranged in a manner similar to the corresponding features of the catheters described above.

The inner guide member 608 may be positioned within the outer tube 606 and fixedly secured to the internal surface of the outer tube 606. In some embodiments, as shown, the outer tube 606 and the inner guide member 608 may be integrally formed with one another. The inner guide member 608 may be curved and contoured as shown in FIGS. 6C-6E, such that a guide lumen 620 is defined between the inner guide member 608 and the outer tube 606. As shown, the guide lumen 620 may be in fluid communication with the access opening 618 and an entry opening 622 defined in the proximal end 604 of the device 600. In this manner, operative instruments or other devices may be passed through the device 600 via the entry opening 622, the guide lumen 620, and the access opening 618. In some embodiments, the inner guide member 608 is formed of a biocompatible polymer, although other suitable materials may be used in other embodiments. For example, the inner guide member 608 may be formed of a polyether block amide (PEBA), such as PEBAX®, a thermoplastic urethane (TPU), such as PELLETHANE®, or a nylon. In some embodiments, the inner guide member 608 includes a liner and/or a reinforcement structure arranged in a manner similar to the corresponding features of the catheters described above.

Figure 6F:
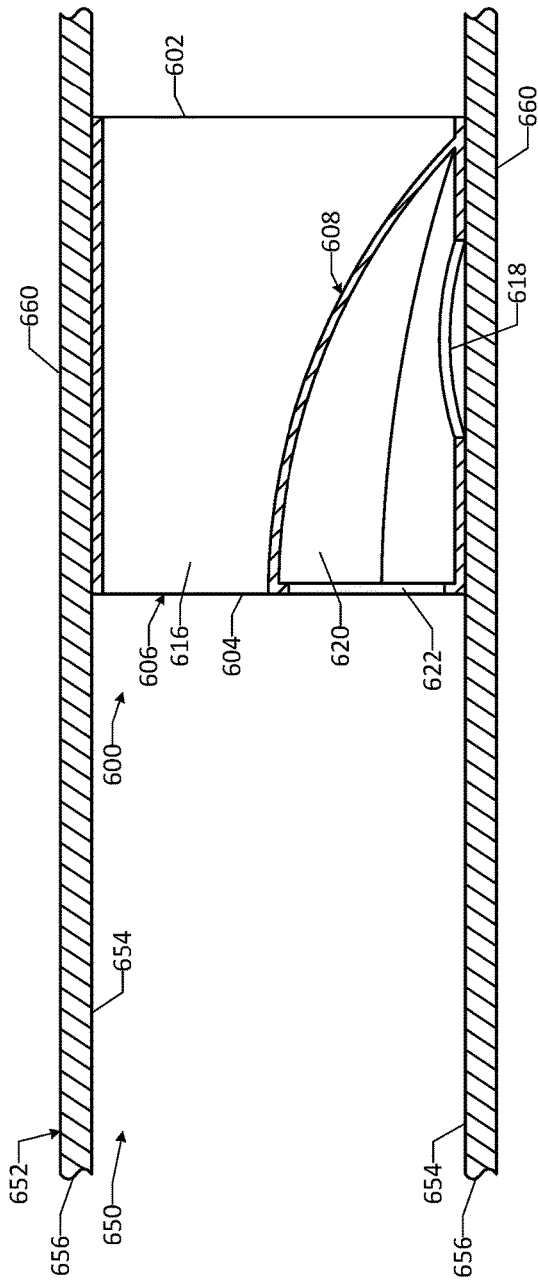
FIG. 6F is a cross-sectional side view of the vascular access device of FIG. 6A positioned within a natural lumen of a vessel.
Figure 6G:
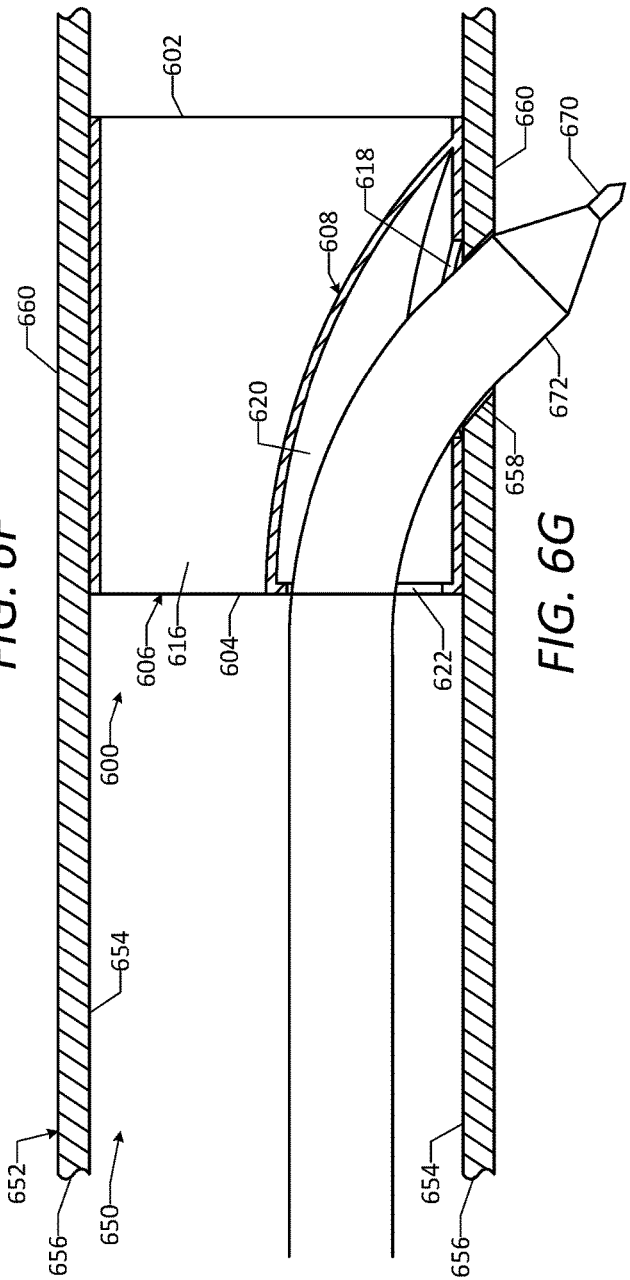
FIG. 6G is a cross-sectional side view of the vascular access device of FIG. 6A positioned within the natural lumen of the vessel, showing a guidewire and a dilator passed through the vascular access device and a wall of the vessel to form an aperture in the vessel wall.
Figure 6H:
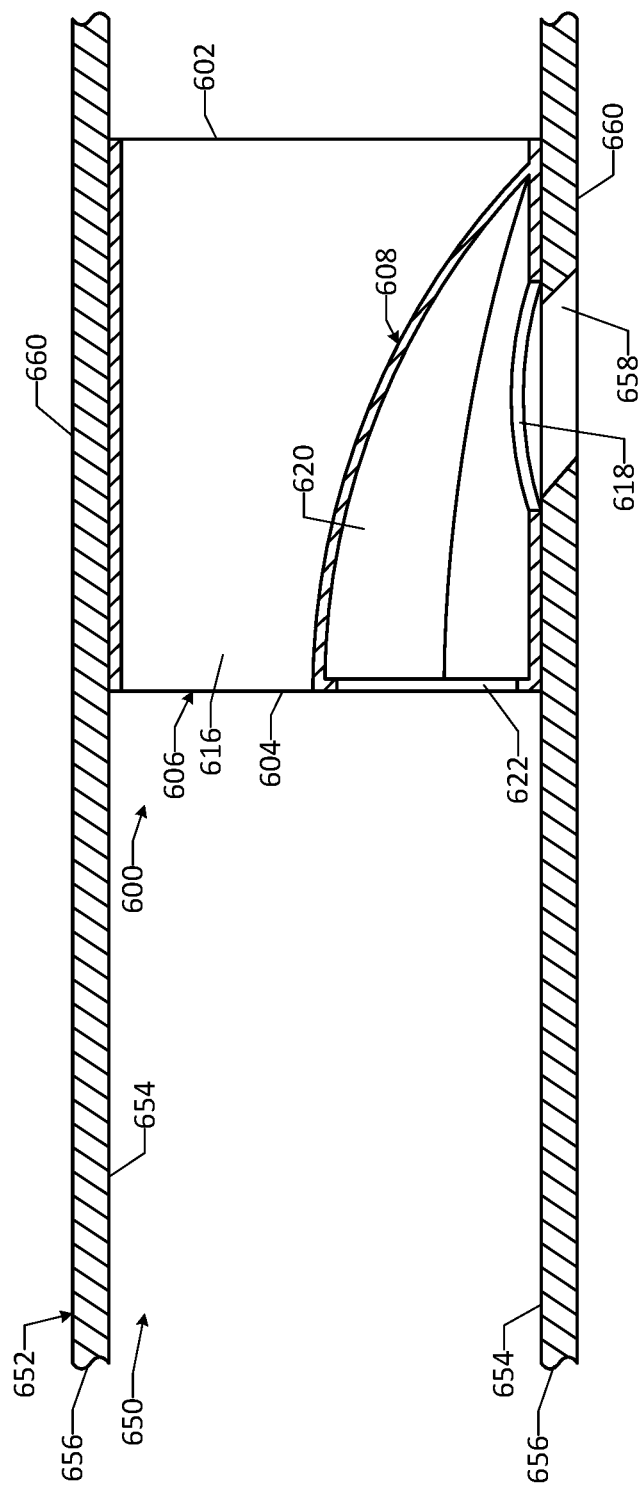
FIG. 6H is a cross-sectional side view of the vascular access device of FIG. 6A positioned within the natural lumen of the vessel, showing the aperture in the vessel wall and a hemostatic connection formed between the vascular access device and the vessel wall.

FIGS. 6F-6H illustrate an example method of using the vascular access device 600 to provide access for performing a cardiac interventional procedure on a patient. Initially, the vascular access device 600 may be percutaneously inserted into the patient through a vascular access site formed in an artery, such as a femoral artery. A catheter or other delivery device may be used to advance the device 600 through the vasculature and position the device 600 at a desired location within a natural lumen 650 of a desired vessel 652. In some embodiments the vascular access device 600 is advanced over a guidewire to facilitate guiding the device 600 through the vasculature and positioning the device 600 at the desired location within vessel 652. When the device 600 is positioned at the desired location within the natural lumen 650 of the vessel 652, a hemostatic connection may be formed between the external surface of the outer tube 606 and an inner surface 654 of a wall 656 of the vessel 652, as shown in FIG. 6F. In particular, the hemostatic connection may be formed between the portion of the external surface of the outer tube 606 that surrounds the access opening 618.

After the hemostatic connection is formed between the external surface of the outer tube 606 and the inner surface 654 of the vessel wall 656, a guidewire 670 and/or a dilator 672 may be advanced through the entry opening 622, the guide lumen 620, and the access opening 618 of the device 600 and through the vessel wall 656, as shown in FIG. 6G. In this manner, the guidewire 670 may form an aperture 658 in the vessel wall 656 extending from the inner surface 654 to an outer surface 660 of the vessel wall 656, as shown. After the aperture 658 is formed in the vessel wall 656, the guidewire 670 and/or the dilator 672 may be retracted and removed from the guide lumen 620 of the device 600, while the hemostatic connection is maintained between the external surface of the outer tube 606 and the inner surface 654 of the vessel wall 656, as shown in FIG. 6H. Before or after removal of the guidewire 670 and/or the dilator 672 from the guide lumen 620, a cardiac interventional procedure may be performed through the vascular access device 600 and through the aperture 658, while the hemostatic connection is maintained between the external surface of the outer tube 606 and the inner surface 654 of the vessel wall 656. In particular, one or more operative instruments or devices may be passed through the guide lumen 620 and the access opening 618 of the device 600 and the aperture 658 in the vessel wall 656 and into the thoracic cavity of the patient to perform a desired cardiac procedure on the desired vasculature. Upon completion of the cardiac procedure, the aperture 658 in the vessel wall 656 may be closed, and the vascular access device 600 may be removed from the patient.

In some embodiments, the vascular access device 600 may be used in combination with other devices to perform a desired cardiac procedure. For example, the vascular access device 600 may be used in combination with one of the puncturable balloon catheter devices described in U.S. Provisional Patent Application Ser. No. 62/331,229 to Crisco to perform a desired cardiac procedure, such as a coronary bypass procedure, as described therein. In such uses, the vascular access device 600 may be used inside of the vessel 652 in the manner described above, and the puncturable balloon catheter device may be used outside of the vessel 652 in the extravascular space, in the soft tissue of a limb of other anatomical locations including the chest and the pericardium, for the purpose of creating space for delivery of catheters, wires, delivery systems, and bypass conduits for the purposes of revascularization. Moreover, the vascular access device 600 may be used instead of the vascular access devices described in U.S. Provisional Patent Application Ser. No. 62/331,229 to Crisco to perform any of the cardiac procedures described therein.

Publications cited herein and the materials for which they are cited are specifically incorporated by reference. Modifications and variations of the devices, systems, and methods described herein will be obvious to those skilled in the art from the foregoing detailed description. Such modifications and variations are intended to come within the scope of the appended claims.

We claim:

1. A method of using a vascular access device to provide access for performing a cardiac procedure on a patient, the method comprising:
    percutaneously inserting a distal end portion of the vascular access device into a natural lumen of a vessel of the patient;
    deploying at least one deployable wire from a catheter of the vascular access device such that the at least one deployable wire engages an inner surface of a wall of the vessel and biases the catheter to engage the inner surface such that a hemostatic connection is formed between the catheter and the inner surface; and
    advancing at least one instrument through the catheter and through the wall to form an aperture in the wall, while maintaining the hemostatic connection between the catheter and the inner surface.

2. The method of claim 1, wherein percutaneously inserting the distal end portion of the vascular access device into the natural lumen of the vessel comprises:
    inserting the distal end portion through an access site formed in an artery of the patient; and
    maintaining a proximal end portion of the vascular access device outside of the patient.

3. The method of claim 1, wherein the distal end portion is configured to move between a straight configuration and a curved configuration, and wherein percutaneously inserting the distal end portion of the vascular access device into the natural lumen of the vessel comprises inserting the distal end portion into the natural lumen while the distal end portion is in the straight configuration.

4. The method of claim 3, further comprising, prior to deploying the at least one deployable wire from the catheter, moving the distal end portion or allowing the distal end portion to move from the straight configuration to the curved configuration.

5. The method of claim 4, wherein moving the distal end portion or allowing the distal end portion to move from the straight configuration to the curved configuration comprises:
    allowing at least one non-deployable wire of the device to bias the distal end portion toward the curved configuration; and
    engaging the inner surface of the wall with the catheter.

6. The method of claim 1, wherein the catheter comprises a distal tip portion positioned about a distal end of the vascular access device, and wherein the hemostatic connection is formed between the distal tip portion and the inner surface.

7. The method of claim 1, wherein the hemostatic connection surrounds the aperture in the wall of the vessel.

8. The method of claim 1, further comprising injecting at least one fluid comprising a contrast medium through at least one thru lumen of the catheter, and assessing the integrity of the hemostatic connection or the aperture in the wall of the vessel by observing the flow of the at least one fluid.

9. The method of claim 8, wherein the at least one thru lumen comprises:
    an internal thru lumen extending from the proximal end of the catheter to an internal surface of a distal tip portion of the catheter; and
    an external thru lumen extending from the proximal end of the catheter to an external surface of a distal tip portion of the catheter.

10. The method of claim 1, wherein the at least one instrument comprises a guidewire and a dilator, and wherein advancing the at least one instrument through the catheter and through the wall to form the aperture comprises puncturing the wall with the guidewire and dilating the aperture with the dilator.

11. The method of claim 1, wherein the catheter comprises an access opening defined in a side wall of the catheter, wherein the hemostatic connection is formed between a portion of an external surface of the catheter surrounding the access opening and the inner surface, and wherein an edge of the access opening surrounds the aperture in the wall of the vessel.

12. The method of claim 1, wherein the at least one deployable wire comprises a plurality of deployable wires.

\* \* \* \* \*